(12) United States Patent
Copland, III et al.

(10) Patent No.: US 11,833,144 B2
(45) Date of Patent: Dec. 5, 2023

(54) TREATING AUTOIMMUNE DISEASE

(71) Applicant: Mayo Foundation for Medical Education and Research, Rochester, MN (US)

(72) Inventors: John A. Copland, III, Ponte Vedra Beach, FL (US); Hu Zeng, Rochester, MN (US)

(73) Assignee: Mayo Foundation for Medical Education and Research, Rochester, MN (US)

(*) Notice: Subject to any disclaimer, the term of this patent is extended or adjusted under 35 U.S.C. 154(b) by 37 days.

(21) Appl. No.: 17/410,137

(22) Filed: Aug. 24, 2021

(65) Prior Publication Data

US 2022/0062259 A1 Mar. 3, 2022

Related U.S. Application Data

(60) Provisional application No. 63/070,505, filed on Aug. 26, 2020.

(51) Int. Cl.
*A61K 31/4545* (2006.01)
*A61P 37/06* (2006.01)
*A61K 31/496* (2006.01)

(52) U.S. Cl.
CPC ........ *A61K 31/4545* (2013.01); *A61K 31/496* (2013.01); *A61P 37/06* (2018.01)

(58) Field of Classification Search
None
See application file for complete search history.

(56) References Cited

U.S. PATENT DOCUMENTS 7,767,677 B2 * 8/2010 Kamboj ............... A61P 5/50
514/252.02

FOREIGN PATENT DOCUMENTS

WO WO 2016/022955 2/2016

OTHER PUBLICATIONS

Rathi et al., Expert Opinion on Therapeutic Patents, vol. 26, Issue 7, May (Year: 2016).*
Akkaya et al., "Second signals rescue B cells from activation-induced mitochondrial dysfunction and death," Nat. Immunology, Jul. 9, 2018 19(8):871-884.
ALJohani et al., "Insights into stearoyl-CoA desaturase-1 regulation of systemic metabolism," Trends Endocrinol. Metabolism. Dec. 2017, 28(12):831-842.
Alwarawrah et al., "Changes in Nutritional Status Impact Immune Cell Metabolism and Function," Front. Immunology, May 16, 2018, 9:1055, 14 pages.
Balmer et al., "Memory CD8(+) T Cells Require Increased Concentrations of Acetate Induced by Stress for Optimal Function," Immunity, Jun. 21, 2016, 44(6):1312-1324.
Boothby et al., "Metabolic Regulation of the Immune Humoral Response," Immunity, May 16, 2017, 46(5):743-755.
Caro-Maldonado et al., "Metabolic reprogramming is required for antibody production that is suppressed in anergic but exaggerated in chronically BAFF-exposed B cells," J. Immunology, Apr. 15, 2014, 192(8):3626-3636.
Carter et al., "The global burden of SLE: prevalence, health disparities and socioeconomic impact," Nat. Rev. Rheumatology, Oct. 2016, 12(10):605-620.
Cho et al., "Glycolytic rate and lymphomagenesis depend on PARP14, an ADP ribosyltransferase of the B aggressive lymphoma (BAL) family," Proc. Natl. Acad. Sci. USA, Sep. 20, 2011, 108(38):15972-15977.
Crouch et al., "Frontline science: a reduction in DHA-derived mediators in male obesity contributes toward defects in select B cell subsets and circulating antibody," J. Leukoc. Biology, Aug. 2019, 106(2):241-257.
De Boer et al., "Transgenic mice with hematopoietic and lymphoid specific expression of Cre," Eur. J. Immunology, Feb. 2003, 33(2):314-325.

(Continued)

*Primary Examiner* — Zinna Northington Davis
(74) *Attorney, Agent, or Firm* — Fish & Richardson P.C.

(57) ABSTRACT

A method for treating a mammal having an autoimmune disease, wherein said method comprises administering a SCD1 polypeptide inhibitor to said mammal, wherein said SCD1 polypeptide inhibitor is a compound having Formula (II):

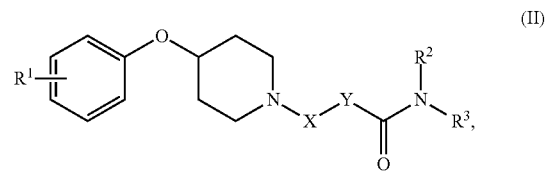

(II)

or a pharmaceutically acceptable salt thereof;
wherein:
R$^1$ is halo;
X is —(C═O)NR$^4$—;
Y is

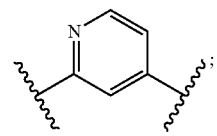

and
R2, R3, and R4 are each independently H or an unsubstituted alkyl.

18 Claims, 38 Drawing Sheets
Specification includes a Sequence Listing.

(56) References Cited

OTHER PUBLICATIONS

Dobrzyn et al., "Stearoyl-CoA desaturase 1 deficiency increases fatty acid oxidation by activating AMP-activated protein kinase in liver," Proc. Natl. Acad. Sci. USA, Apr. 27, 2004, 101(17):6409-6414.
Dufort et al., "Cutting edge: IL-4-mediated protection of primary B lymphocytes from apoptosis via Stat6-dependent regulation of glycolytic metabolism," J. Immunology, Oct. 15, 2007, 179(8):4953-4957.
Dufort et al., "Glucose-dependent de novo lipogenesis in B lymphocytes: a requirement for atp-citrate lyase in lipopolysaccharide-induced differentiation," J. Biol. Chemistry, Mar. 7, 2014, 289(10):7011-7024.
Fagarasan et al., "Adaptive immune regulation in the gut: T cell-dependent and T cell-independent IgA synthesis," Annu. Rev. Immunology, Mar. 1, 2010, 28:243-273.
Fritsche, "Fatty acids as modulators of the immune response," Annu. Rev. Nutrition, Aug. 21, 2006, 26:45-73.
Fritsche, "The science of fatty acids and inflammation," Adv. Nutrition, May 15, 2015, 6(3):293S-301S.
Gally et al., "FABP5 deficiency enhances susceptibility to H1N1 influenza A virus-induced lung inflammation," Am. J. Physiol. Lung Cell Mol. Physiology, Jul. 1, 2013, 305(1):L64-72.
GenBank Accession No. AB032261.1, "*Homo sapiens* Scd mRNA for stearoyl-CoA desaturase, complete cds," dated Apr. 4, 2000, 2 pages.
GenBank Accession No. AB208982.1, "*Homo sapiens* mRNA for stearoyl-CoA desaturase variant protein," dated Jul. 26, 2016, 2 pages.
GenBank Accession No. NC_000010.11, "*Homo sapiens* chromosome 10, GRCh38.p13 Primary Assembly," dated Jun. 14, 2019, 3 pages.
GenBank Accession No. NM_005063.5, "*Homo sapiens* stearoyl-CoA desaturase (SCD), mRNA," dated Jul. 31, 2019, 5 pages.
GenBank Accession No. XM_001723785.1, "Predicted: *Homo sapiens* similar to Putative uncharacterized protein PRO1933 (LOC100133188), mRNA," dated Feb. 29, 2008, 2 pages.
GenBank Accession No. XM_001725202.1, "Predicted: *Homo sapiens* similar to Putative uncharacterized protein PRO1933 (LOC100133188), mRNA," dated Feb. 29, 2008, 2 pages.
Gurzell et al., "DHA-enriched fish oil targets B cell lipid microdomains and enhances ex vivo and in vivo B cell function," J. Leukoc. Biology, Apr. 2013, 93(4):463-470.
Hertzel et al., "Lipid metabolism and adipokine levels in fatty acid-binding protein null and transgenic mice," Am. J. Physiol. Endocrinol. Metabolism, May 2006, 290(5):E814-823.
Hobeika et al., "Testing gene function early in the B cell lineage in mb1-cre mice," Proc. Natl. Acad. Sci. USA, Sep. 12, 2006, 103(37):13789-13794.
Hotamisligil et al., "Metabolic functions of FABPs—mechanisms and therapeutic implications," Nat. Rev. Endocrinology, Oct. 2015, 11(10):592-605.
Huang et al., "SCD1 negatively regulates autophagy-induced cell death in human hepatocellular carcinoma through inactivation of the AMPK signaling pathway," Cancer Letters, Mar. 28, 2015, 358(2):180-190.
Iwata et al., "Conditional Disruption of Raptor Reveals an Essential Role for mTORC1 in B Cell Development, Survival, and Metabolism," J. Immunology, Sep. 15, 2016, 197(6):2250-2260.
Jones et al., "mTOR has distinct functions in generating versus sustaining humoral immunity," J. Clin. Investigation, Nov. 1, 2016, 126(11):4250-4261.
Kaestner et al., "Differentiation-induced gene expression in 3T3-L1 preadipocytes. A second differentially expressed gene encoding stearoyl-CoA desaturase," J. Biol. Chemistry. Sep. 5, 1989, 264(25):14755-14761.
Kedia-Mehta et al., "Competition for nutrients and its role in controlling immune responses," Nat. Communications, May 9, 2019, 10(1):2123.
Kim et al., "mTOR: a pharmacologic target for autophagy regulation," J. Clin. Investigation, Jan. 2015, 125(1):25-32.
Kim et al., "TopHat2: accurate alignment of transcriptomes in the presence of insertions, deletions and gene fusions," Genome Biology, Apr. 25, 2013, 14(4):R36, 13 pages.
Kosaraju et al., "B Cell Activity Is Impaired in Human and Mouse Obesity and Is Responsive to an Essential Fatty Acid upon Murine Influenza Infection," J. Immunology, Jun. 15, 2017, 198(12):4738-4752.
Koutsari et al., "Measuring plasma fatty acid oxidation with intravenous bolus injection of 3H- and 14C-fatty acid," J. Lipid Research, Jan. 2013, 54(1):254-264.
Kunisawa et al., "Regulation of intestinal IgA responses by dietary palmitic acid and its metabolism," J. Immunology, Aug. 15, 2014, 193(4):1666-1671.
Kurmi et al., "Carnitine Palmitoyltransferase IA Has a Lysine Succinyltransferase Activity," Cell Reports, Feb. 6, 2018, 22(6):1365-1373.
Le et al., "Glucose-independent glutamine metabolism via TCA cycling for proliferation and survival in B cells," Cell Metabolism, Jan. 4, 2012, 15(1):110-121.
Lee et al., "Requirement for Rictor in homeostasis and function of mature B lymphoid cells," Blood, Oct. 3, 2013, 122(14):2369-2379.
Ma et al., "Serine Is an Essential Metabolite for Effector T Cell Expansion," Cell Metabolism, Feb. 7, 2017, 25(2):345-357.
Miyazaki et al., "A lipogenic diet in mice with a disruption of the stearoyl-CoA desaturase 1 gene reveals a stringent requirement of endogenous monounsaturated fatty acids for triglyceride synthesis," J. Lipid Research, Jul. 2001, 42(7):1018-1024.
Miyazaki et al., "Hepatic stearoyl-CoA desaturase-1 deficiency protects mice from carbohydrate-induced adiposity and hepatic steatosis," Cell Metabolism, Dec. 2007, 6(6):484-496.
Miyazaki et al., "Targeted disruption of stearoyl-CoA desaturase1 gene in mice causes atrophy of sebaceous and meibomian glands and depletion of wax esters in the eyelid," J. Nutrition, Sep. 2001, 131(9):2260-2268.
Mizushima et al., "The role of Atg proteins in autophagosome formation," Annu. Rev. Cell Dev. Biology, Nov. 2011, 27:107-132.
Ntambi et al., "Loss of stearoyl-CoA desaturase-1 function protects mice against adiposity," Proc. Natl. Acad. Sci. USA, Aug. 20, 2002, 99(17):11482-11486.
Ogasawara et al., "Stearoyl-CoA desaturase 1 activity is required for autophagosome formation," J. Biol. Chemistry, Aug. 22, 2014, 289(34):23938-23950.
O'Sullivan et al., "Memory CD8(+) T cells use cell-intrinsic lipolysis to support the metabolic programming necessary for development," Immunity, Jul. 17, 2014, 41(1):75-88.
Persson et al., "Rapid measurement of plasma free fatty acid concentration and isotopic enrichment using LC/MS," J. Lipid Research, Sep. 2010, 51(9):2761-2765.
Ramon et al., "Specialized proresolving mediators enhance human B cell differentiation to antibody-secreting cells," J. Immunology, Jul. 15, 2012, 189(2):1036-1042.
Rangel-Moreno et al., "B cells promote resistance to heterosubtypic strains of influenza via multiple mechanisms," J. Immunology, Jan. 1, 2008, 180(1):454-463.
Raybuck et al., "B Cell-Intrinsic mTORCI Promotes Germinal Center-Defining Transcription Factor Gene Expression, Somatic Hypermutation, and Memory B Cell Generation in Humoral Immunity," J. Immunology, Apr. 15, 2018, 200(8):2627-2639.
Rickert et al., "B lymphocyte-specific, Cre-mediated mutagenesis in mice," Nucleic Acids Research, Mar. 1, 1997, 25(6):1317-1318.
Robinson et al., "edgeR: a Bioconductor package for differential expression analysis of digital gene expression data," Bioinformatics, Jan. 2010, 26(1):139-140.
Roper et al., "Prostaglandin E2 promotes B lymphocyte Ig isotype switching to IgE," J. Immunology, Jan. 1, 1995, 154(1):162-170.
Roy et al., "Methionine Metabolism Shapes T Helper Cell Responses through Regulation of Epigenetic Reprogramming," Cell Metabolism, Feb. 4, 2020, 31(2):250-266.e9.

(56) References Cited

OTHER PUBLICATIONS

Rytter et al., "The immune system in children with malnutrition—a systematic review," PLOS One, Aug. 25, 2014, 9(8):e105017, 19 pages.

Shin et al., "Analysis of the free fatty acid metabolome in the plasma of patients with systemic lupus erythematosus and fever," Metabolomics, Apr. 2018, 14:14.

Siegemund et al., "hCD2-iCre and Vav-iCre mediated gene recombination patterns in murine hematopoietic cells," PLOS One, Apr. 17, 2015, 10(4):e0124661, 17 pages.

Son et al., "Inhibition of Stearoyl-CoA desaturases suppresses follicular help T and germinal center B cell responses," Eur. J. Immunology, Jul. 2020, 50(7):1067-1077.

Tan et al., "Critical role of SCD1 in autophagy regulation via lipogenesis and lipid rafts-coupled AKT-FOXO1 signaling pathway," Autophagy, Feb. 2014, 10(2):226-242.

Von Roemeling et al., "Accelerated bottom-up drug design platform enables the discovery of novel stearoyl-CoA desaturase 1 inhibitors for cancer therapy," Oncotarget, Oct. 6, 2017, 9(1):3-20.

Wang et al., "RSeQC: quality control of RNA-seq experiments," Bioinformatics, Aug. 15, 2012, 28(16):2184-2185.

Wang et al., "The transcription factor Myc controls metabolic reprogramming upon T lymphocyte activation," Immunity, Dec. 23, 2011, 35(6):871-882.

Waters et al., "Initial B Cell Activation Induces Metabolic Reprogramming and Mitochondrial Remodeling," iScience, Jul. 27, 2018, 5:99-109.

Wei et al., "Saturated fatty acids induce endoplasmic reticulum stress and apoptosis independently of ceramide in liver cells," Am. J. Physiol. Endocrinol. Metabolism, Aug. 2006, 291(2):E275-281.

Weisel et al., "Germinal center B cells selectively oxidize fatty acids for energy while conducting minimal glycolysis," Nat. Immunology, Mar. 2020, 21(3):331-342.

Zeng et al., "Discrete roles and bifurcation of PTEN signaling and mTORC1-mediated anabolic metabolism underlie IL-7-driven B lymphopoiesis," Sci. Advances, Jan. 31, 2018, 4(1):eaar5701.

Zeng et al., "mTORC1 and mTORC2 Kinase Signaling and Glucose Metabolism Drive Follicular Helper T Cell Differentiation," Immunity, Sep. 20, 2016, 45(3):540-554.

Zeng et al., "mTORC1 couples immune signals and metabolic programming to establish T(reg)-cell function," Nature, Jul. 25, 2013, 499(7459):485-490.

Zeng, "Metabolic regulation of lymphocytes in health and autoimmunity," Presented in Chile, Aug. 27, 2019, 41 pages.

Zhou et al., "Stearoyl-CoA Desaturase-Mediated Monounsaturated Fatty Acid Availability Supports Humoral Immunity," Cell Reports, Jan. 5, 2021, 34(1):108601.

\* cited by examiner

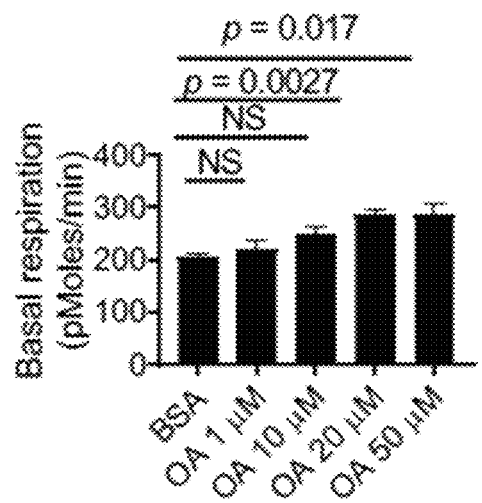
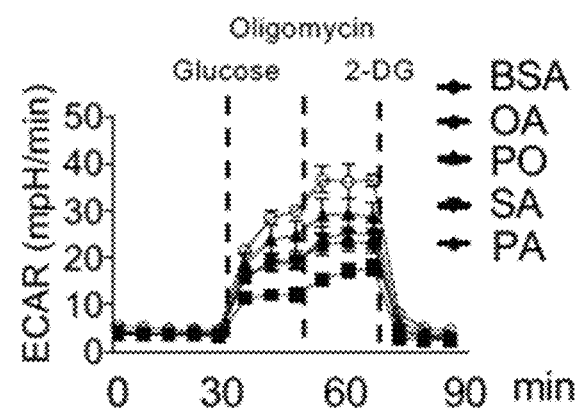
FIG. 3D  FIG. 3E
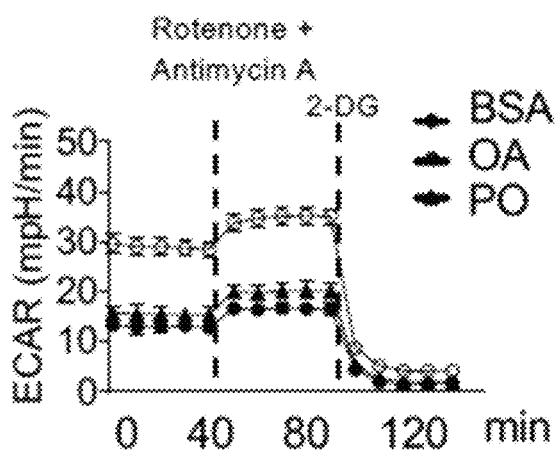
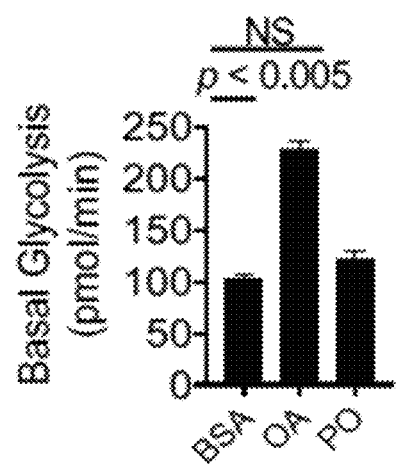
FIG. 3F

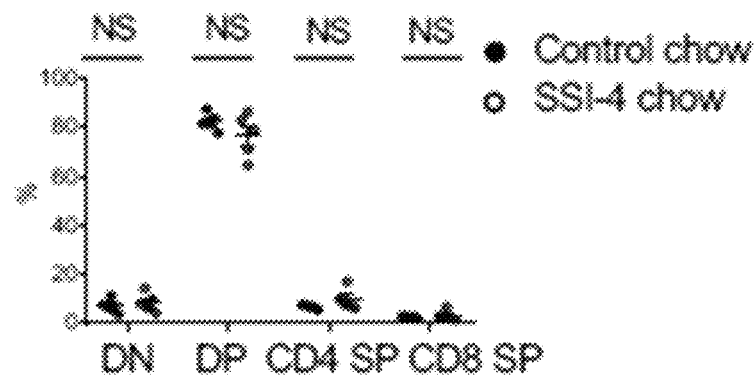
FIG. 12C
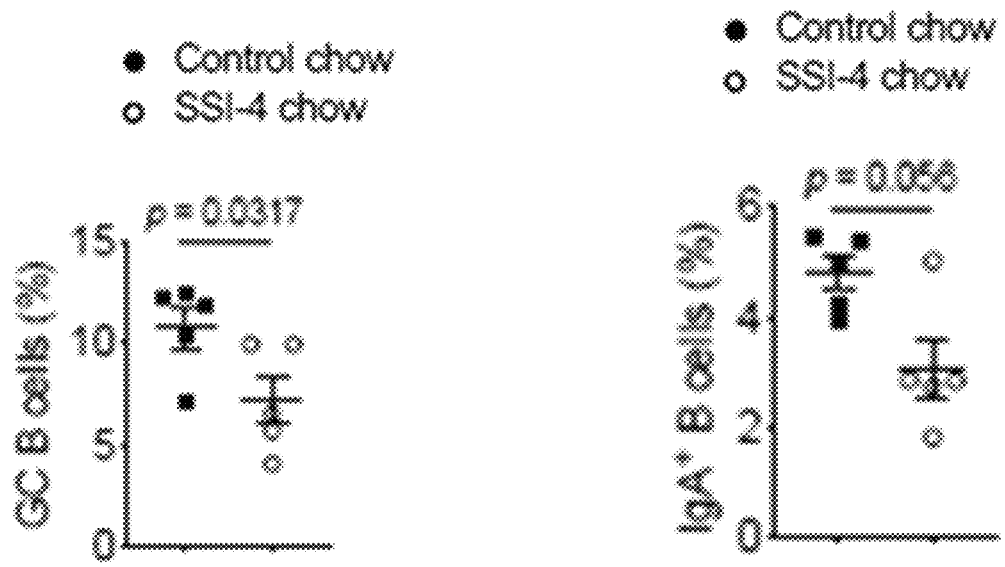
FIG. 12D
FIG. 12E

FIG. 14B
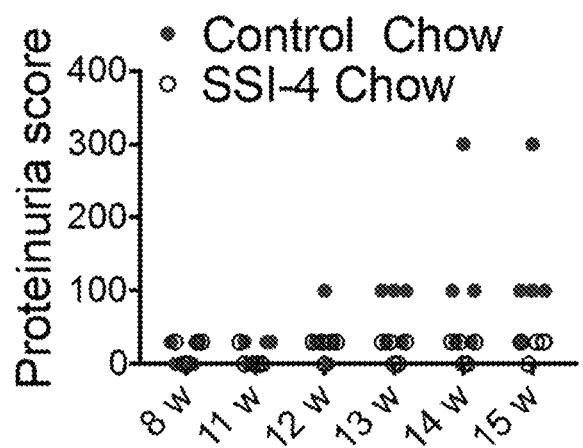
FIG. 14C
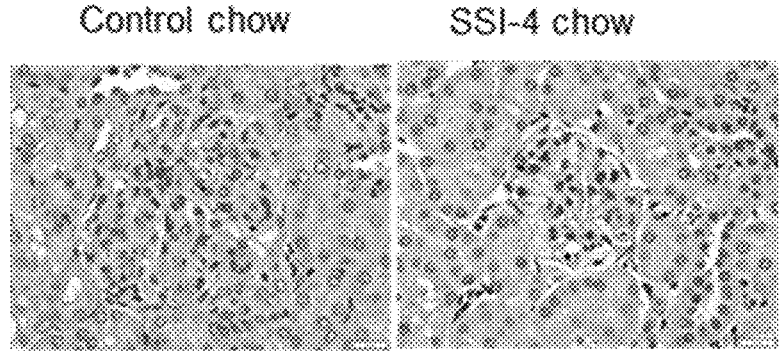
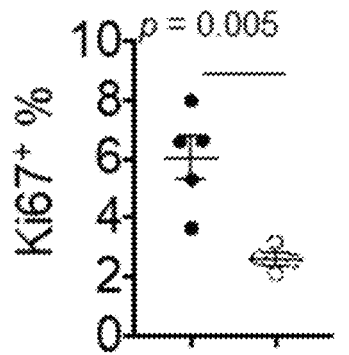
FIG. 14D
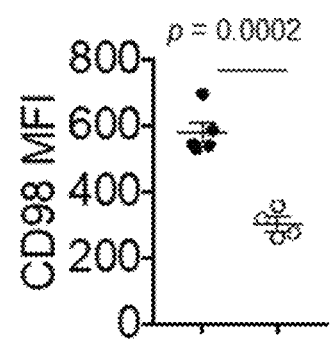
FIG. 14E

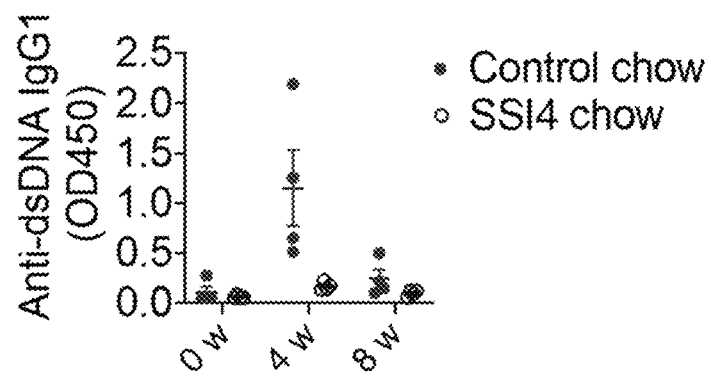
FIG. 14F
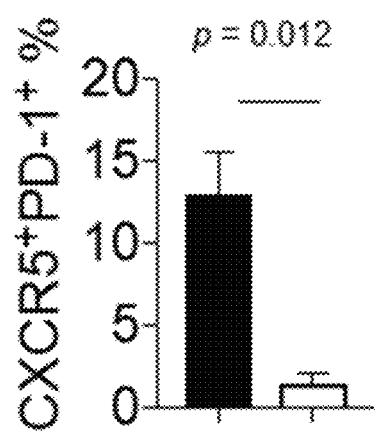 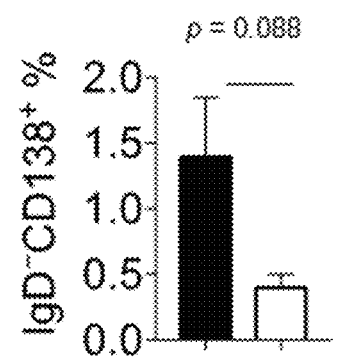
FIG. 14G  FIG. 14H

SEQUENCE LISTING

<160> NUMBER OF SEQ ID NOS: 20

<210> SEQ ID NO 1
<211> LENGTH: 22
<212> TYPE: DNA
<213> ORGANISM: Artificial
<220> FEATURE:
<223> OTHER INFORMATION: oligonucleotide primer

<400> SEQUENCE: 1
ttcttgcgat acactctggt gc                                              22

<210> SEQ ID NO 2
<211> LENGTH: 22
<212> TYPE: DNA
<213> ORGANISM: Artificial
<220> FEATURE:
<223> OTHER INFORMATION: oligonucleotide primer

<400> SEQUENCE: 2
cgggattgaa tgttcttgtc gt                                              22

```
<210> SEQ ID NO 3
<211> LENGTH: 20
<212> TYPE: DNA
<213> ORGANISM: Artificial
<220> FEATURE:
<223> OTHER INFORMATION: oligonucleotide primer

<400> SEQUENCE: 3
gcatttggga gccttgtacg                                                20

<210> SEQ ID NO 4
<211> LENGTH: 21
<212> TYPE: DNA
<213> ORGANISM: Artificial
<220> FEATURE:
<223> OTHER INFORMATION: oligonucleotide primer

<400> SEQUENCE: 4
agccgtgcct tgtatgttct g                                              21

<210> SEQ ID NO 5
<211> LENGTH: 21
<212> TYPE: DNA
<213> ORGANISM: Artificial
<220> FEATURE:
<223> OTHER INFORMATION: oligonucleotide primer

<400> SEQUENCE: 5
ggaggtggtg atagccggta t                                              21

<210> SEQ ID NO 6
<211> LENGTH: 21
<212> TYPE: DNA
<213> ORGANISM: Artificial
<220> FEATURE:
<223> OTHER INFORMATION: oligonucleotide primer

<400> SEQUENCE: 6
tgggtaatcc atagagccca g                                              21

<210> SEQ ID NO 7
<211> LENGTH: 21
<212> TYPE: DNA
<213> ORGANISM: Artificial
<220> FEATURE:
<223> OTHER INFORMATION: oligonucleotide primer

<400> SEQUENCE: 7
gtccccaggg atgaaccaat a                                              21

<210> SEQ ID NO 8
<211> LENGTH: 21
<212> TYPE: DNA
<213> ORGANISM: Artificial
<220> FEATURE:
<223> OTHER INFORMATION: oligonucleotide primer

<400> SEQUENCE: 8
gccatgctca accaaagtag c                                              21

<210> SEQ ID NO 9
<211> LENGTH: 21
<212> TYPE: DNA
<213> ORGANISM: Artificial
<220> FEATURE:
<223> OTHER INFORMATION: oligonucleotide primer
```

<400> SEQUENCE: 9
ctggaagcct ggtatgagga t						21

<210> SEQ ID NO 10
<211> LENGTH: 22
<212> TYPE: DNA
<213> ORGANISM: Artificial
<220> FEATURE:
<223> OTHER INFORMATION: oligonucleotide primer

<400> SEQUENCE: 10
cagggtcaag agtagtgaag gt					22

<210> SEQ ID NO 11
<211> LENGTH: 20
<212> TYPE: DNA
<213> ORGANISM: Artificial
<220> FEATURE:
<223> OTHER INFORMATION: oligonucleotide primer

<400> SEQUENCE: 11
gggttctgtc ttccactcca						20

<210> SEQ ID NO 12
<211> LENGTH: 19
<212> TYPE: DNA
<213> ORGANISM: Artificial
<220> FEATURE:
<223> OTHER INFORMATION: oligonucleotide primer

<400> SEQUENCE: 12
aagcagcaga gtcaggctt						19

<210> SEQ ID NO 13
<211> LENGTH: 19
<212> TYPE: DNA
<213> ORGANISM: Artificial
<220> FEATURE:
<223> OTHER INFORMATION: oligonucleotide primer

<400> SEQUENCE: 13
aggatgggga cttggttgc						19

<210> SEQ ID NO 14
<211> LENGTH: 21
<212> TYPE: DNA
<213> ORGANISM: Artificial
<220> FEATURE:
<223> OTHER INFORMATION: oligonucleotide primer

<400> SEQUENCE: 14
tcacagatca cattggggtg c						21

<210> SEQ ID NO 15
<211> LENGTH: 20
<212> TYPE: DNA
<213> ORGANISM: Artificial
<220> FEATURE:
<223> OTHER INFORMATION: oligonucleotide primer

<400> SEQUENCE: 15
agttctacac ctggctttgg						20

<210> SEQ ID NO 16
<211> LENGTH: 22

-continued

```
<212> TYPE: DNA
<213> ORGANISM: Artificial
<220> FEATURE:
<223> OTHER INFORMATION: oligonucleotide primer

<400> SEQUENCE: 16
gttggcaatg atcagaaaga gc                                              22

<210> SEQ ID NO 17
<211> LENGTH: 22
<212> TYPE: DNA
<213> ORGANISM: Artificial
<220> FEATURE:
<223> OTHER INFORMATION: oligonucleotide primer

<400> SEQUENCE: 17
gatatcccag agatgtttcg gc                                              22

<210> SEQ ID NO 18
<211> LENGTH: 22
<212> TYPE: DNA
<213> ORGANISM: Artificial
<220> FEATURE:
<223> OTHER INFORMATION: oligonucleotide primer

<400> SEQUENCE: 18
gtcagcatgt cagaaggcag ag                                              22

<210> SEQ ID NO 19
<211> LENGTH: 24
<212> TYPE: DNA
<213> ORGANISM: Artificial
<220> FEATURE:
<223> OTHER INFORMATION: oligonucleotide primer

<400> SEQUENCE: 19
agaacttgca ggagttctgg gaca                                            24

<210> SEQ ID NO 20
<211> LENGTH: 24
<212> TYPE: DNA
<213> ORGANISM: Artificial
<220> FEATURE:
<223> OTHER INFORMATION: oligonucleotide primer

<400> SEQUENCE: 20
tccgaagaag gaggcatcaa acct                                            24
```

TREATING AUTOIMMUNE DISEASE

CROSS-REFERENCE TO RELATED APPLICATIONS

This application claims the benefit of U.S. Patent Application Ser. No. 63/070,505, filed on Aug. 26, 2020. The disclosure of the prior application is considered part of (and is incorporated by reference in) the disclosure of this application.

SEQUENCE LISTING

This application contains a Sequence Listing that has been submitted electronically as an ASCII text file named Sequence_Listing.txt. The ASCII text file, created on Sep. 13, 2021, is 4 kilobytes in size. The material in the ASCII text file is hereby incorporated by reference in its entirety.

TECHNICAL FIELD

This document relates to methods and materials involved in treating mammals (e.g., humans) having an autoimmune disease (e.g., a systemic autoimmune disease such as lupus). For example, one or more stearoyl CoA desaturase 1 (SCD1) polypeptide inhibitors (e.g., a selective SCD1 inhibitor (SSI)) can be administered to a mammal having an autoimmune disease (e.g., a systemic autoimmune disease such as lupus) to treat the mammal.

BACKGROUND INFORMATION

Lupus is a chronic autoimmune disease that can cause inflammation and pain in any part of the body. It is estimated that at least 1.5 million Americans (and at least five million people worldwide) have some form of lupus (Roper, Lupus Awareness Survey for the Lupus Foundation of America [Executive Summary Report]. Washington, D.C. (2012)), and that the average annual direct health care costs of a person with lupus was $33,223 (Carter et al., *Nature Reviews Rheumatology*, 12(10), 605-620 (2016)).

SUMMARY

This document provides methods and materials for treating mammals (e.g., humans) having an autoimmune disease (e.g., a systemic autoimmune disease such as lupus). For example, one or more SCD1 polypeptide inhibitors (e.g., a SSI) can be administered to a mammal having an autoimmune disease (e.g., lupus) to treat the mammal. For example, this document provides methods and materials for administering one or more SCD1 polypeptide inhibitors (e.g., a SSI) to treat a mammal having an autoimmune disease under conditions wherein the severity of the autoimmune disease is reduced.

As demonstrated herein, murine and human B cells preferentially rely on oleic acid (OA) to maintain metabolic fitness and promote antibody production. SCD1, which catalyzes the generation of endogenous OA, contributes to B cell development and activation. Also as demonstrated herein, inhibition of SCD1 can be used to treat autoimmune disease (e.g., lupus). For example, administering the SCD1 inhibitor SSI-4 can ameliorate disease progression in lupus mouse models. Having the ability to reduce B cell development and activation through metabolic intervention as described herein (e.g., by inhibiting SCD1) provides a unique opportunity to treat autoimmune disease (e.g., lupus).

In general, one aspect of this document features methods for treating a mammal having an autoimmune disease. The methods can include, or consist essentially of, administering a SCD1 polypeptide inhibitor to a mammal having an autoimmune disease. The mammal can be a human. The autoimmune disease can be a systemic autoimmune disease. The autoimmune disease can be lupus (e.g., systemic lupus erythematosus (SLE), cutaneous lupus, drug-induced lupus, or neonatal lupus), rheumatoid arthritis, spondyloarthropathy, Sjogren's syndrome, polymyositis, dermatomyositis, scleroderma, or multiple sclerosis. The SCD1 polypeptide inhibitor can be a compound having Formula (II):

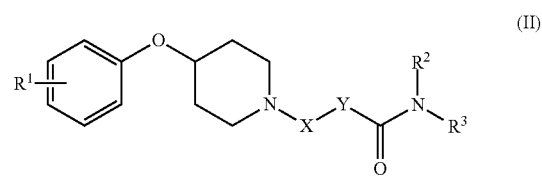

(II)

or a pharmaceutically acceptable salt thereof; where $R^1$ is halo; X is —(C=O)NR$^4$—; Y is

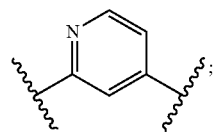 [SMILES: *c1ccnc(*)c1]

and $R^2$, $R^3$, and $R^4$ are each independently H or an unsubstituted $C_{1-6}$alkyl. The SCD1 polypeptide inhibitor can be a compound having Formula (IIa):

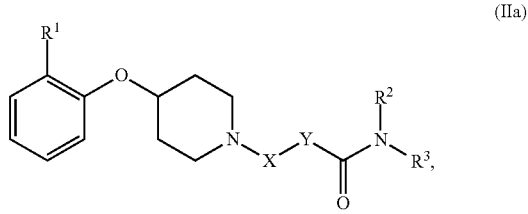

(IIa)

or a pharmaceutically acceptable salt thereof. The SCD1 polypeptide inhibitor can be 2-{[4-(2-Chlorophenoxy)piperidine-1-carbonyl]amino}-N-methylpyridine-4-carboxamide:

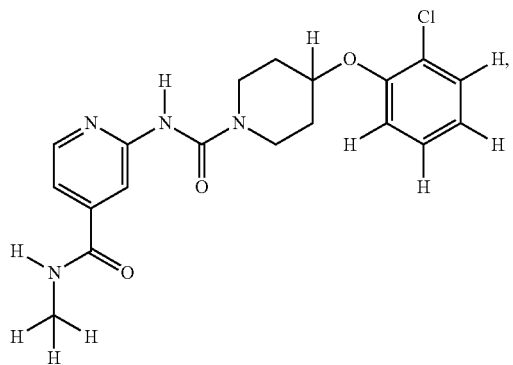

or a pharmaceutically acceptable salt thereof. The SCD1 polypeptide inhibitor can be a compound having Formula (I):

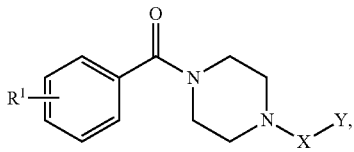
(I)

or a pharmaceutically acceptable salt thereof; where $R^1$ is an unsubstituted $C_{1-6}$alkyl or $C_{1-6}$ haloalkyl, X is

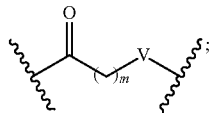;

Y is selected from:

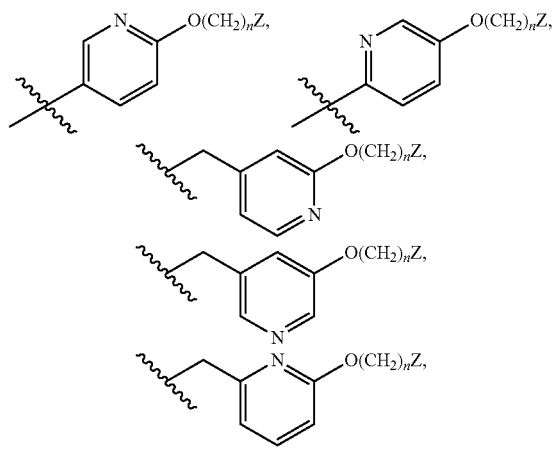

m is 0 or 1; n is 0, 1, or 2; V is $NR^4$ or O; $R^2$, $R^3$, and $R^4$ are each independently H or an unsubstituted $C_{1-6}$alkyl; and Z is an unsubstituted aryl. The SCD1 polypeptide inhibitor can be a compound having Formula (Ia):

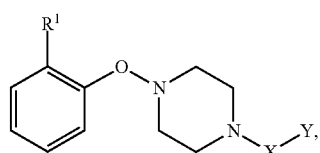
(Ia)

or a pharmaceutically acceptable salt thereof. The SCD1 polypeptide inhibitor can be 2-(benzyloxy)-5-{[hydroxy({4-[2-(trifluoromethyl)benzoyl]piperazin-1-yl})methyl]amino}-1,2-dihydropyridin-2-ylium-1-ide:

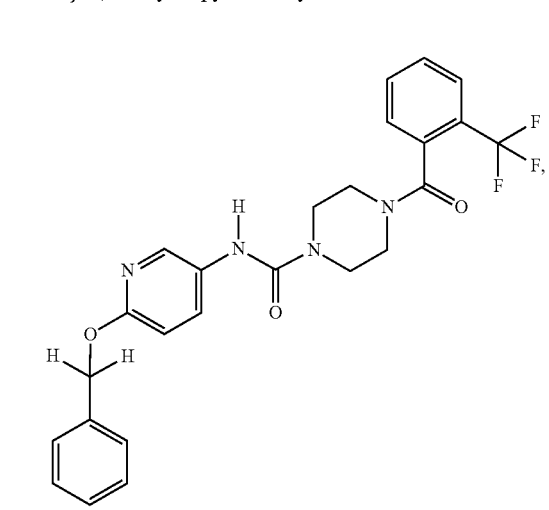

or a pharmaceutically acceptable salt thereof. The method also can include identifying the mammal as having the autoimmune disease.

In another aspect, this document features methods for treating an autoimmune disease. The methods can include, or consist essentially of, administering a SCD1 polypeptide inhibitor to a mammal identified as having an autoimmune disease. The mammal can be a human. The autoimmune disease can be a systemic autoimmune disease. The autoimmune disease can be lupus (e.g., SLE, cutaneous lupus, drug-induced lupus, or neonatal lupus), rheumatoid arthritis, spondyloarthropathy, Sjogren's syndrome, polymyositis, dermatomyositis, scleroderma, or multiple sclerosis. The SCD1 polypeptide inhibitor can be a compound having Formula (II):

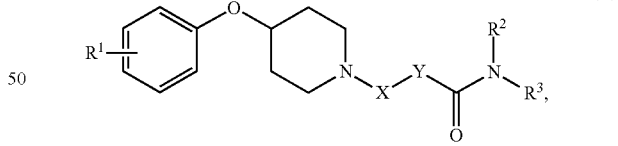
(II)

or a pharmaceutically acceptable salt thereof; where $R^1$ is halo; X is $—(C=O)NR^4—$; Y is

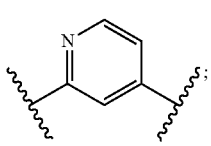;

and $R^2$, $R^3$, and $R^4$ are each independently H or an unsubstituted $C_{1-6}$alkyl. The SCD1 polypeptide inhibitor can be a compound having Formula (IIa):

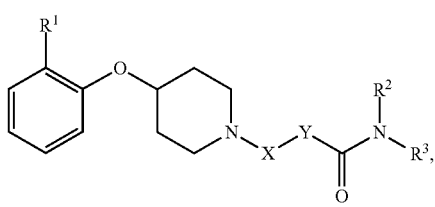

(IIa)

or a pharmaceutically acceptable salt thereof. The SCD1 polypeptide inhibitor can be 2-{[4-(2-Chlorophenoxy)piperidine-1-carbonyl]amino}-N-methylpyridine-4-carboxamide:

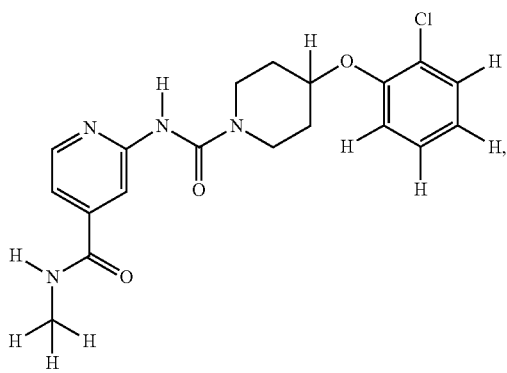

or a pharmaceutically acceptable salt thereof. The SCD1 polypeptide inhibitor can be a compound having Formula (I):

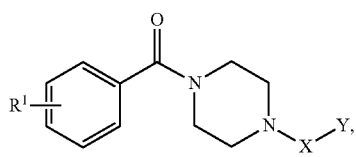

(I)

or a pharmaceutically acceptable salt thereof where $R^1$ is an unsubstituted $C_{1-6}$alkyl or $C_{1-6}$haloalkyl; X is

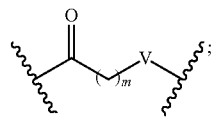

Y is selected from:

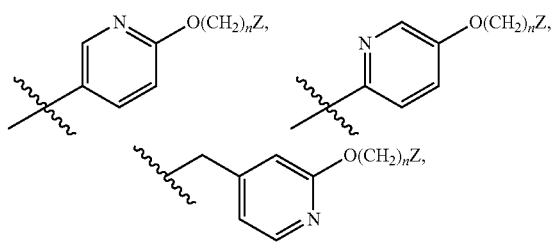

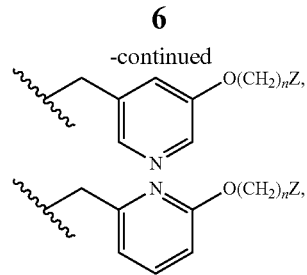

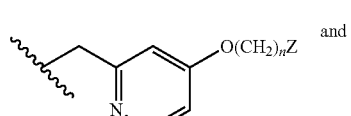 and 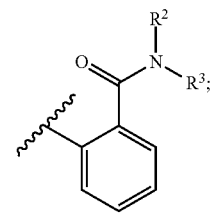

m is 0 or 1; n is 0, 1, or 2; V is $NR^4$ or O; $R^2$, $R^3$, and $R^4$ are each independently H or an unsubstituted $C_{1-6}$alkyl; and Z is an unsubstituted aryl. The SCD1 polypeptide inhibitor can be a compound having Formula (Ia):

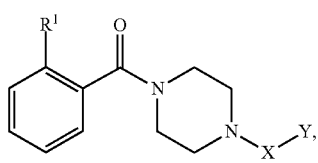

(Ia)

or a pharmaceutically acceptable salt thereof. The SCD1 polypeptide inhibitor can be 2-(benzyloxy)-5-{[hydroxy({4-[2-(trifluoromethyl)benzoyl]piperazin-1-yl})methyl]amino}-1,2-dihydropyridin-2-ylium-1-ide:

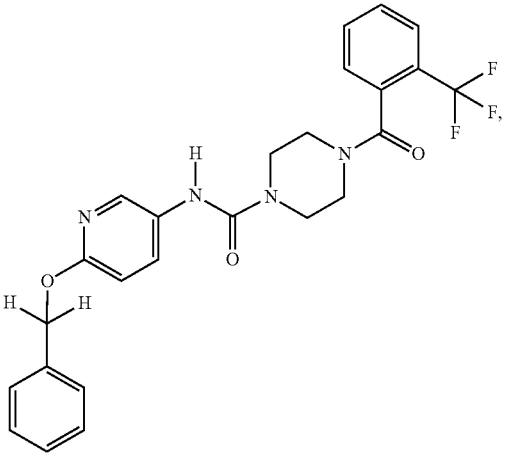 [SMILES: O=C(Nc1ccc(OCc2ccccc2)nc1)N1CCN(C(=O)c2ccccc2C(F)(F)F)CC1]

or a pharmaceutically acceptable salt thereof.

In another aspect, this document features methods for reducing a symptom of an autoimmune disease in a mammal. The methods can include, or consist essentially of, administering a SCD1 polypeptide inhibitor to a mammal having an autoimmune disease. The symptom can be fatigue, fever, joint pain, joint stiffness, joint swelling, butterfly-shaped rash, photosensitivity, Raynaud's phenomenon, shortness of breath, chest pain, dry eyes, headaches, confusion, memory loss, or any combination thereof. The mammal can be a human. The autoimmune disease can be a systemic autoimmune disease. The autoimmune disease can be lupus (e.g., SLE, cutaneous lupus, drug-induced lupus, or neonatal lupus), rheumatoid arthritis, spondyloarthropathy, Sjogren's syndrome, polymyositis, dermatomyositis, scleroderma, or multiple sclerosis. The SCD1 polypeptide inhibitor can be a compound having Formula (II):

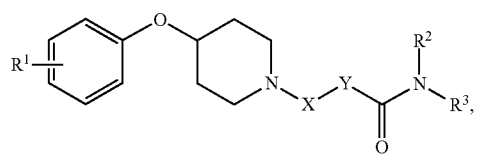
(II)

or a pharmaceutically acceptable salt thereof; where $R^1$ is halo; X is —(C=O)$NR^4$—; Y is

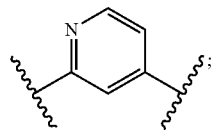 [SMILES: *c1ccnc(*)c1]

and $R^2$, $R^3$, and $R^4$ are each independently H or an unsubstituted $C_{1-6}$alkyl. The SCD1 polypeptide inhibitor can be a compound having Formula (IIa):

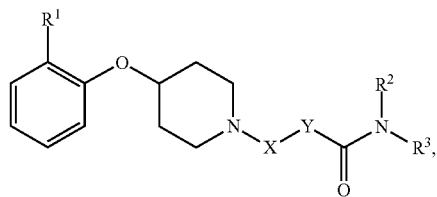
(IIa)

or a pharmaceutically acceptable salt thereof. The SCD1 polypeptide inhibitor can be 2-{[4-(2-Chlorophenoxy)piperidine-1-carbonyl]amino}-N-methylpyridine-4-carboxamide:

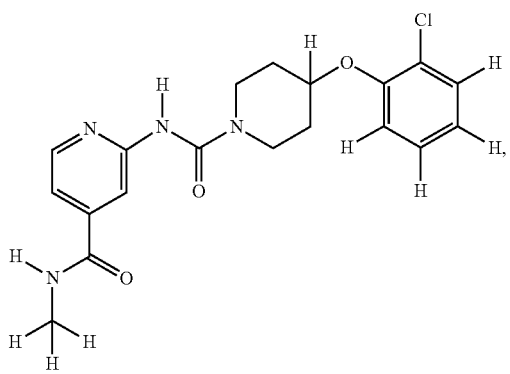

or a pharmaceutically acceptable salt thereof. The SCD1 polypeptide inhibitor can be a compound having Formula (I):

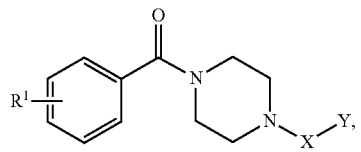
(I)

or a pharmaceutically acceptable salt thereof; where $R^1$ is an unsubstituted $C_{1-6}$alkyl or $C_{1-6}$ haloalkyl; X is

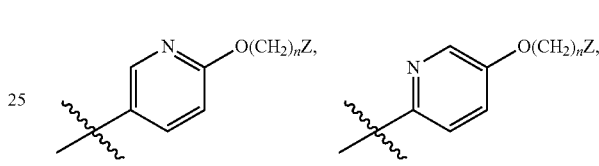

Y is selected from:

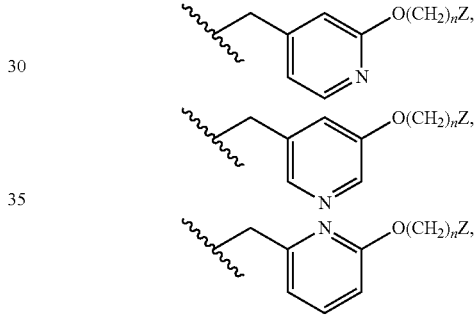

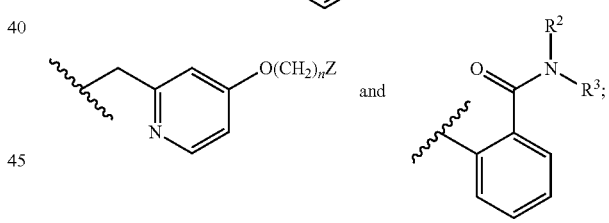
and m is 0 or 1; n is 0, 1, or 2; V is $NR^4$ or O; $R^2$, $R^3$, and $R^4$ are each independently H or an unsubstituted $C_{1-6}$alkyl; and Z is an unsubstituted aryl. The SCD1 polypeptide inhibitor can be a compound having Formula (Ia):

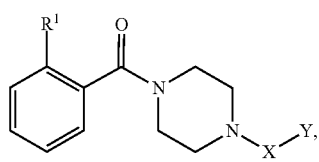
(Ia)

or a pharmaceutically acceptable salt thereof. The SCD1 polypeptide inhibitor can be 2-(benzyloxy)-5-{[hydroxy({4-[2-(trifluoromethyl)benzoyl]piperazin-1-yl})methyl]amino}-1,2-dihydropyridin-2-ylium-1-ide:

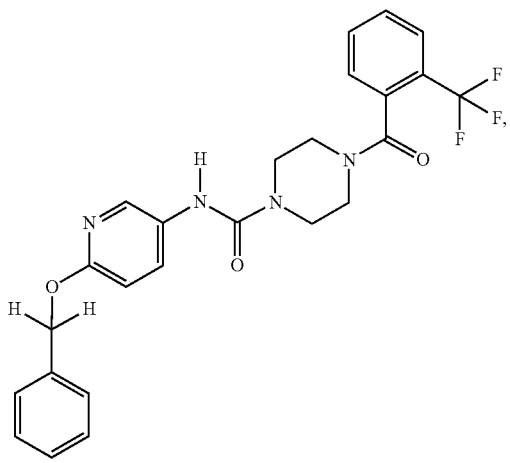 [SMILES: O=C(Nc1ccc(OCc2ccccc2)nc1)N1CCN(C(=O)c2ccccc2C(F)(F)F)CC1]

or a pharmaceutically acceptable salt thereof.

In another aspect, this document features methods for reducing biosynthesis of a fatty acid (e.g., to reduce a serum concentration of a fatty acid) in a mammal having an autoimmune disease. The methods can include, or consist essentially of, administering a SCD1 polypeptide inhibitor to a mammal having an autoimmune disease. The fatty acid can be palmitoleic acid (PO), oleic acid (OA), vaccenic acid, or any combination thereof. The mammal can be a human. The autoimmune disease can be a systemic autoimmune disease. The autoimmune disease can be lupus (e.g., SLE, cutaneous lupus, drug-induced lupus, or neonatal lupus), rheumatoid arthritis, spondyloarthropathy, Sjogren's syndrome, polymyositis, dermatomyositis, scleroderma, or multiple sclerosis. The SCD1 polypeptide inhibitor can be a compound having Formula (II):

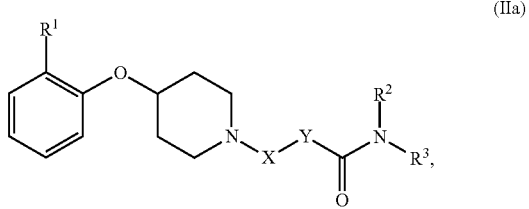

or a pharmaceutically acceptable salt thereof; where $R^1$ is halo; X is —(C═O)NR$^4$—; Y is

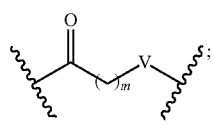

and $R^2$, $R^3$, and $R^4$ are each independently H or an unsubstituted $C_{1-6}$alkyl. The SCD1 polypeptide inhibitor can be a compound having Formula (IIa):

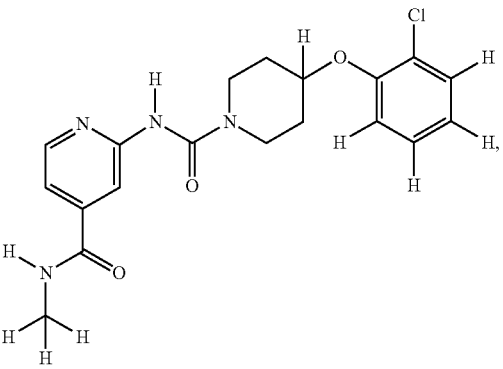

or a pharmaceutically acceptable salt thereof. The SCD1 polypeptide inhibitor can be 2-{[4-(2-Chlorophenoxy)piperidine-1-carbonyl]amino}-N-methylpyridine-4-carboxamide:

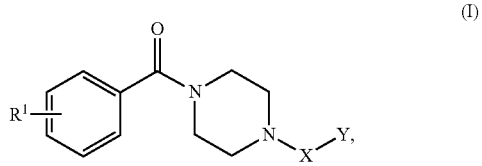

or a pharmaceutically acceptable salt thereof. The SCD1 polypeptide inhibitor can be a compound having Formula (I):

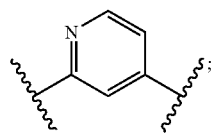 [SMILES: *c1ccnc(*)c1]

or a pharmaceutically acceptable salt thereof; where $R^1$ is an unsubstituted $C_{1-6}$alkyl or $C_{1-6}$haloalkyl; X is Y is selected from:

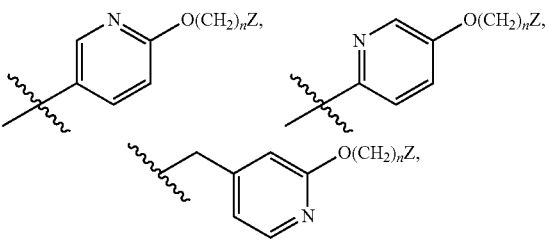

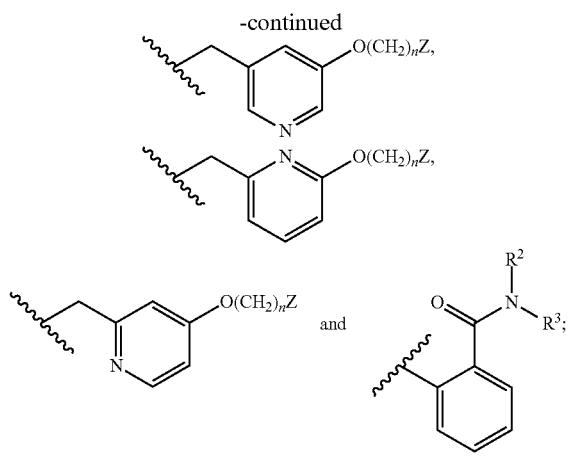

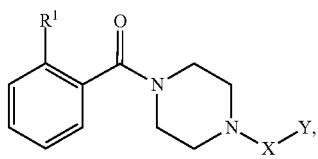

and m is 0 or 1; n is 0, 1, or 2; V is $NR^4$ or O; $R^2$, $R^3$, and $R^4$ are each independently H or an unsubstituted $C_{1-6}$alkyl; and Z is an unsubstituted aryl. The SCD1 polypeptide inhibitor can be a compound having Formula (Ia):

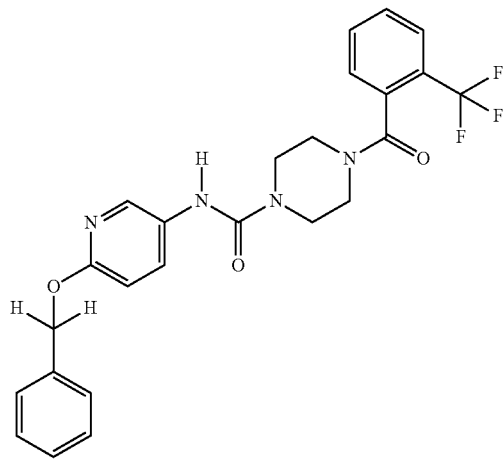 [SMILES: O=C(Nc1ccc(OCc2ccccc2)nc1)N1CCN(C(=O)c2ccccc2C(F)(F)F)CC1]

or a pharmaceutically acceptable salt thereof. The SCD1 polypeptide inhibitor can be 2-(benzyloxy)-5-{[hydroxy({4-[2-(trifluoromethyl)benzoyl]piperazin-1-yl})methyl]amino}-1,2-dihydropyridin-2-ylium-1-ide:

or a pharmaceutically acceptable salt thereof.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

(FIG. 1A) Heat map of gene expression related to fatty acid synthesis in murine fresh and activated B cells with LPS/IL-4. (FIG. 1B) mRNA expression of 4 Scd isoforms' expression in freshly isolated or activated B cells, extracted from RNAseq data. "ND", Not detected. (FIG. 1C) Immunoblot analysis of SCD2 in murine fresh and activated B cells by immunoblot. (FIG. 1D) Reverse transcription polymerase chain reaction (RT-PCR) analysis of ACACA, FASN, and SCD expression in human B cells at 0, 8 and 24 hours during activation with CpG/anti-CD40/IL-15/IL-10/IL-2. (FIG. 1E) RT-PCR analysis of Acaca, Fasn, Scd1, and Scd2 expression in murine B cells with or without rapamycin (10 nM) treatment at 8 and 24 hours. 1, fresh B cell; 2, B cells activated with LPS/IL-4 for 8 hours in vitro, 3, B cells activated with LPS/IL-4 plus rapamycin for 8 hours; 4, B cells activated with LPS/IL-4 for 24 hours; 5, B cell activated with LPS/IL-4 plus rapamycin treatment for 24 hours. (FIG. 1F) Composition of palmitoleic acid (PO), oleic acid (OA), palmitic acid (PA), stearic acid (SA), linoleic acid (LA), and arachidonic acid (AA) in fresh and activated B cells treated with vehicle or 100 nM SCD inhibitor SSI-4 for 48 hours was measured by LC-MS/MS. (FIG. 1G) Isotopomer distribution for $^{13}C$ labeled glucose in fatty acid synthesis metabolites OA, SA, vaccenic acid (VA), PO, PA and myristic acid (MA) in activated B cell treated with vehicle or SSI-4 inhibitor at 48 hours. (FIG. 1H) Comparison of $^{13}C$ labeled glucose incorporation in OA and PO in activated B cells isolated from either WT or $Cd2^{iCre}Scd1^{fl/fl}Scd2^{fl/fl}$ mice.

(FIG. 2A) Cell proliferation measured by dilution of Celltrace Violet (CTV) dye in LPS/IL-4 activated murine B cell treated with SCD inhibitors A939572 (1 MF438 (1 and SSI-4 (1 respectively. (FIG. 2B) Cell proliferation of murine B cells stimulated with LPS/IL-4/IL-5, anti-IgM/anti-CD40/IL-4, or CpG/IL-4/IL-5 in presence of vehicle, 100 nM SSI-4, or SSI-4 plus exogenous 100 μM OA, respectively for 3 days. (FIG. 2C) Murine B cells were stimulated with LPS/IL-4/IL-5 for 3 days in the presence of indicated inhibitor and/or fatty acids. Numbers of activated B cells were summarized, and were normalized to vehicle group. (FIG. 2D) Flow cytometry analysis of murine B cell proliferation and class switch to IgG1 activated with LPS/IL-4 in presence of vehicle, SCD inhibitor SSI-4, SSI-4 with exogenous OA (100 SSI-4 with exogenous PO (25 SSI-4 with exogenous SA (25 SSI-4 with exogenous PA (100 OA alone, and PO alone. Right, summary of IgG1$^+$ B cell percentages normalized against vehicle treated samples. (FIG. 2E) Cell proliferation and class switch to IgG1 in activated B cells isolated from WT or $Cd2^{iCre}Scd1^{fl/fl}Scd2^{fl/fl}$ mice detected by flow cytometry. Right, summary of IgG1$^+$ B cell percentage normalized to vehicle treated WT samples. (FIG. 2F) Human naive B cell proliferation was measured by thymidine incorporation after activation in the presence of vehicle, SCD inhibitor SSI-4

(10 nM), SSI-4 plus exogenous OA, and OA alone. (FIG. 2G) Flow cytometry analysis of CD27 expression on activated human B cells in the presence of vehicle, SSI-4, SSI-4 plus OA or OA alone. Numbers indicate the mean fluorescence intensity (MFI). p values were calculated with one-way ANOVA. NS, not significant. Data were representative of at least 3 (FIG. 2A-FIG. 2E) or 2 (FIG. 2F and FIG. 2G) independent experiments. Error bars represent SEM.

FIGS. 3A-3H. MUFA supports B cell metabolic fitness. (FIG. 3A) Flow cytometry of analysis of murine B cell proliferation and class switch to IgG1. Purified splenic B cells were activated with LPS/IL-4 in presence of vehicle (BSA), OA alone (100 etomoxir (40 µM) and OA plus etomoxir at 72 hours. Right, summary of IgG1$^+$ B cell percentage normalized to vehicle treated sample. (FIG. 3B) Oxygen consumption rate (OCR) was measured with a Seahorse XFe96 analyzer using CpG/IL-4/IL-5 activated murine B cells in the presence of BSA, OA, PO, SA and PA for 48 h. Right, summary of basal respiration. (FIG. 3C) Measurement of OCR in human B cells activated in the presence of BSA, OA and PO for 72 hours. Right, summary of basal respiration. (FIG. 3D) Basal respiration was calculated in activated murine B cells with BSA and titrated doses of exogenous OA (1, 10, 20 and 50 (FIG. 3E) Glycolytic capacity of activated murine B cells was measured in presence of BSA, OA, PO, SA and PA at 48 h using a Glycolysis Stress test. Right, summary of glycolytic capacity. (FIG. 3F) Extracellular acidification rate (ECAR) was measured in activated human B cells in the presence of BSA, OA and PO for 72 h. Right, summary of basal glycolysis rate. (FIG. 3G) Measurement of OCR and ECAR in the activated murine B cells in the presence of vehicle or SSI-4 for 48 hours. (FIG. 3H) Staining of TMRM in activated murine B cell in the presence of vehicle, SSI-4, SSI-4 plus OA and OA alone for 72 hours. Right, numbers indicate the MFI of TMRM. p values were calculated with one-way ANOVA. NS, not significant. Data were representative of 3 (FIG. 3A and FIG. 3H) or 2 (FIG. 3B, FIG. 3C, FIG. 3E, and FIG. 3G) independent experiments. Error bars represent SEM.

(FIG. 4A) Transmission electron microscope image of activated mouse B cell treated with vehicle or SSI-4. Arrows indicate autophagosome structures. Right, numbers of autophagosomes found in vehicle (n=8) or SSI-4 (n=11) treated B cells. Scale bars: 0.5 µm. (FIG. 4B) Immunoblot analysis of LC3-I/LC3-II, p-S6, p-S6K, and AID in activated murine B cells in presence of vehicle, SSI-4, SSI-4 plus OA and OA alone. (FIG. 4C) Immunoblot analysis of LC3-I/LC3-II, p-S6, and p-S6K in activated B cells from Cd2$^{iCre}$Scd1$^{+/+}$Scd2$^{+/+}$ and Cd2$^{iCre}$Scd1$^{fl/fl}$Scd2$^{fl/fl}$ mice with or without exogenous OA. (FIG. 4D) Flow cytometry analysis of GFP-LC-3 expression in activated B cells isolated from GFP-LC-3 reporter mouse treated with vehicle, and SSI-4. Numbers indicate the MFI of GFP. (FIG. 4E) Mice were fed with control chow and SSI-4 chow (30 mg/kg), followed by NP-OVA immunization for one week. MFI of p-S6 in splenic B cells was measured by flow cytometry. (FIG. 4F) Cell proliferation and class switch recombination in activated murine B cells treated with SSI-4 in the presence of 3-methyadenine (3-MA) (1 mM) and wortmannin (1 µM), or OA. p was calculated with Student's t-test. Data were representative of 2 (FIG. 4B and FIG. 4C) and 3 (FIG. 4F) independent experiments. Error bars represent SEM.

(FIG. 5A) Flow cytometry analysis of B cell precursors (B220$^{int}$CD19$^+$) and circulating mature B cells (B220$^{hi}$CD19$^+$) in bone marrow from mice fed with control chow or SSI-4 chow. Right, frequencies of B cell precursors and circulating mature B cells. (FIG. 5B) Flow cytometry of pre-B cell (B220$^+$CD25$^+$) in bone marrow from mice fed with control chow or SSI-4 chow. Right, frequencies of pre-B cells. (FIG. 5C-FIG. 5E) Mice were fed with control chow or SSI-4 chow for 2 weeks. The numbers of whole spleen (FIG. 5C), splenic B220$^+$ B cells (FIG. 5D), and CD4$^+$ T cells (FIG. 5E). (FIG. 5F) OA concentration in sera was detected by GC-MS before and after immunization. (FIG. 5G) OA concentration in sera was measured by GC-MS in mice immunized with NP-OVA and treated with control chow or SSI-4 chow. (FIG. 5H-FIG. 5J) Mice were divided into 4 groups. They were fed with control chow or SSI-4 chow, followed with or without NP-OVA immunization. Flow cytometry of germinal center (GC) (FIG. 5H), antigen specific NP$^+$ expression among GC B cells (FIG. 5I), B220$^{int}$CD138$^+$ expression (FIG. 5J), and expression of PD-1 and CXCR5 among CD4$^+$ T cell (FIG. 5K). Right, the frequencies of GC B cells (H), NP$^+$ GC B cells (FIG. 5I), B220$^{int}$CD138$^+$ plasmablasts (FIG. 5J) and PD-1$^+$CXCR5$^+$ Tfh cells (FIG. 5K). (FIG. 5L) Measurements of anti-NP immunoglobulins in serial diluted serum from unimmunized and immunized mice fed with control chow or SSI-4 chow, presented as absorbance at 450 nM (A450) in ELISA. p values were calculated with Student's t-test. NS, not significant. Data were representative of 2 (FIG. 5A-FIG. 5G) and 3 (FIG. 5H-FIG. 5L) independent experiments. Error bars represent SEM.

(FIG. 6A) The ratio of OA/SA and PA/PO in sera before and after influenza infection. (FIG. 6B) Body weight change in mice fed with control chow or SSI-4 chow for one week following influenza infection. (FIG. 6C) Flow cytometry analysis of GC B cells in mediastinal lymph nodes at day 11 following infection. Right, the frequencies of GC B cells. (FIG. 6D) The frequencies of Bcl6$^+$ expression among B cells in mediastinal lymph nodes. (FIG. 6E) The frequencies of B220$^{int}$CD138$^+$ plasmablasts. (FIG. 6F) Flow cytometry analysis of Tfh cells in mediastinal lymph nodes. Right, the frequencies of CXCR5Bcl6$^{hi}$ Tfh among CD4$^+$ T cells in mediastinal lymph nodes. (FIG. 6G) Influenza virus specific antibody IgG, IgG1, IgG2c and IgM in sera were measured by ELISA. p was calculated with Student's t-test and one-way ANOVA. Results were pooled from 2 (FIG. 6A-FIG. 6F) independent experiments. Error bars represent SEM.

(FIG. 7A) Flow cytometry analysis of B cell development in bone marrow from WT and Cd2$^{iCre}$Scd1$^{fl/fl}$Scd2$^{fl/fl}$ mice. Right, the frequencies of B220$^+$CD43$^+$ pro-B cells, B220$^{int}$CD43$^-$ pre-B/immature B cells and B220$^{hi}$CD43$^-$ circulating mature B cells. (FIG. 7B) WT and Cd19$^{Cre}$Scd1$^{fl/fl}$ Scd2$^{fl/fl}$ mice were immunized with NP-OVA. Flow cytometry analysis of GC B cells. Right, the frequencies of GC B cells. (FIG. 7C and FIG. 7D) B cells were purified from tamoxifen treated Cre$^{ER}$Scd1$^{+/+}$Scd2$^{+/+}$ and Cre$^{ER}$Scd1$^{fl/fl}$Scd2$^{fl/fl}$ mice. They were mixed with CD4 T cells purified from OT-II mice and WT C57BL/6 mice, and transferred into Rag1$^{-/-}$ mice. The recipient mice were immunized with NP-OVA. (FIG. 7C) Flow cytometry analysis of GC B cells in spleen. Right, the frequencies of GC B cells. (FIG. 7D)

Measurements of anti-NP immunoglobulins in sera at 2 and 4 weeks after first immunization, presented as absorbance at 450 nM (A450) in ELISA. p was calculated with Student's t test and one-way ANOVA. NS, not significant. Data were pooled from at least 3 (FIG. 7A) and represent 2 (FIG. 7C, FIG. 7D) independent experiments. Error bars represent SEM.

Figure 8A:
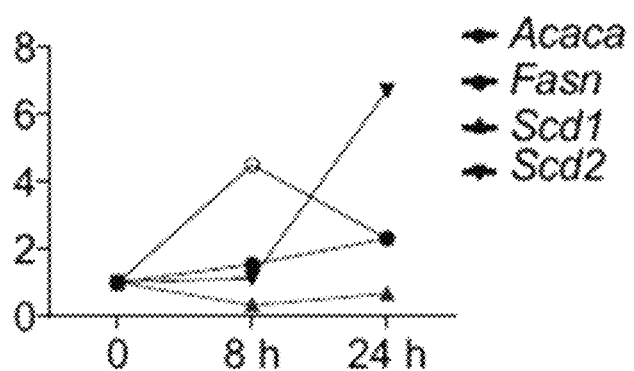
Figure 8B:
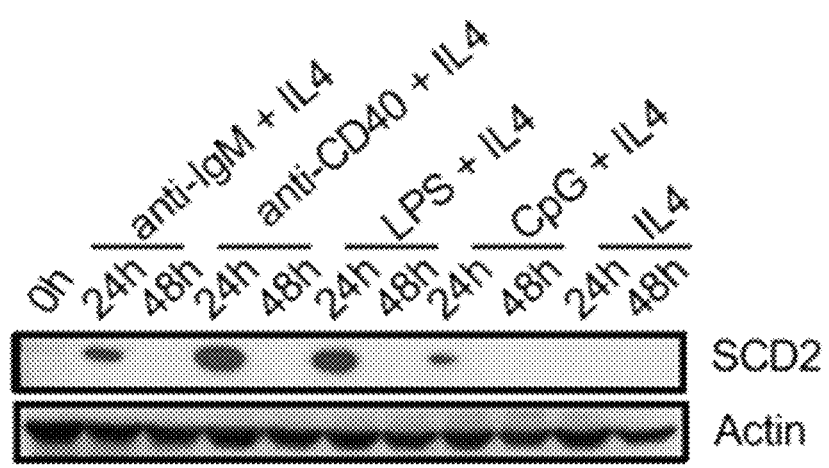
Figure 8C:
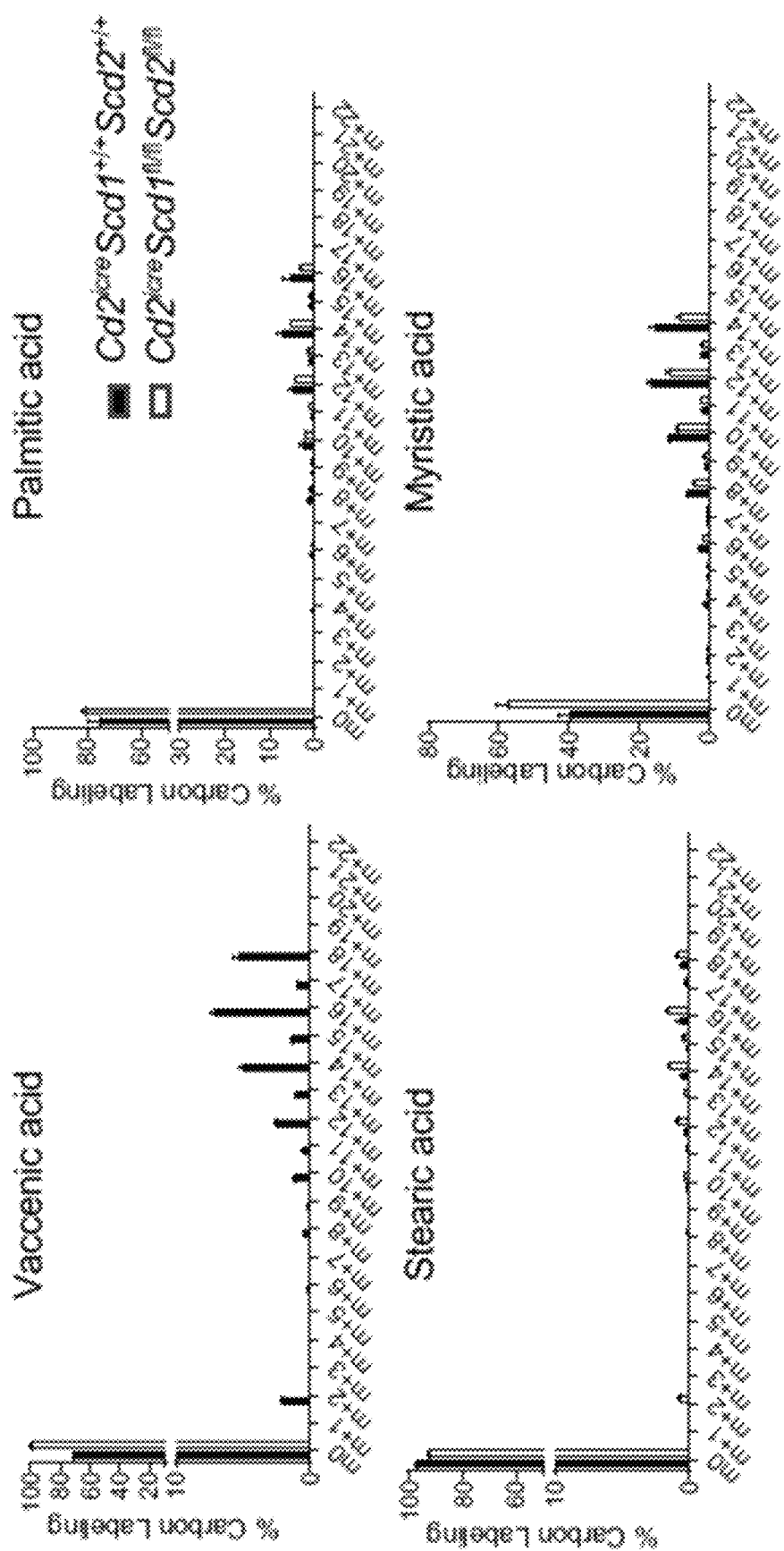

FIGS. 8A-8C. (FIG. 8A) Reverse transcription polymerase chain reaction (RT-PCR) analysis of Acaca, Fasn, Scd1 and Scd2 expression in murine B cells at 0, 8 and 24 hours with LPS/IL-4 activation. (FIG. 8B) Immunoblot analysis of SCD2 in fresh isolated murine B cells, and B cells activated with anti-IgM (10 μg/mL)/IL-4, anti-CD40 (10 μg/mL)/IL-4, LPS (10 μg/mL)/IL-4, CpG (2.5 μM)/IL-4, or IL-4 alone at 24 and 48 hours by immunoblot. (FIG. 8C) Incorporation of $^{13}$C labeled glucose into VA, PA, SA and MA were measured by LC-MS/MS in activated B cell isolated from WT or Cd2$^{iCre}$Scd1$^{fl/fl}$Scd2$^{fl/fl}$ mice.

Figure 9:
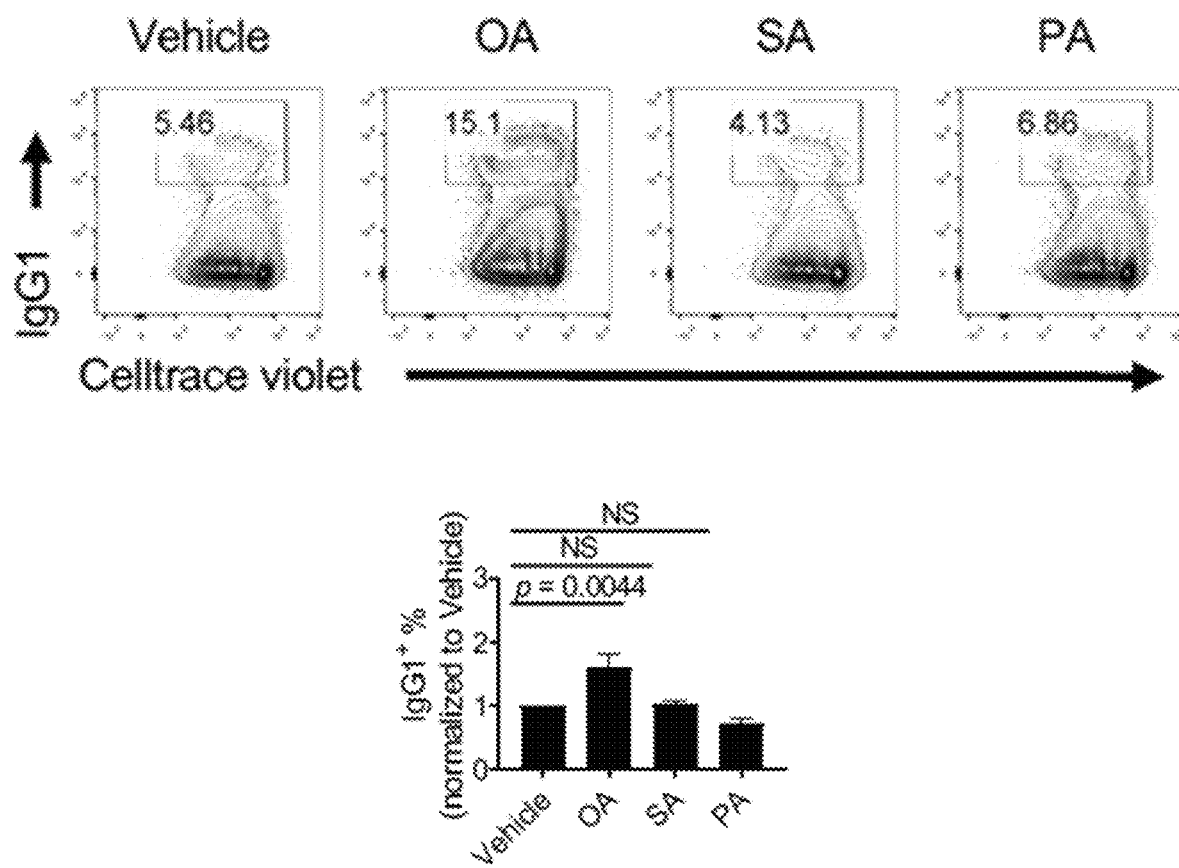

FIG. 9. Flow cytometry analysis of murine B cell proliferation and class switch in presence of OA, SA and PA. Right, the frequencies of IgG1$^+$ B cell activated with LPS/IL-4 in presence of OA, PA and SA. The percentages were normalized to vehicle (BSA) group. p value was calculated with one-way ANOVA. NS, not significant. Results were pooled from 3 independent experiments. Error bars represent SEM.

Figure 10A:
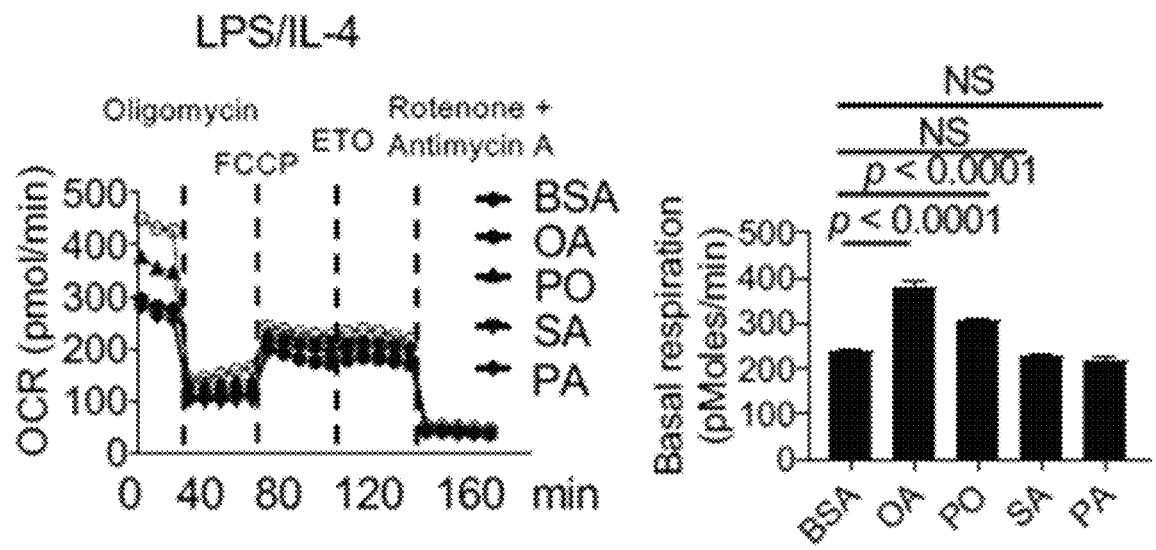
Figure 10B:
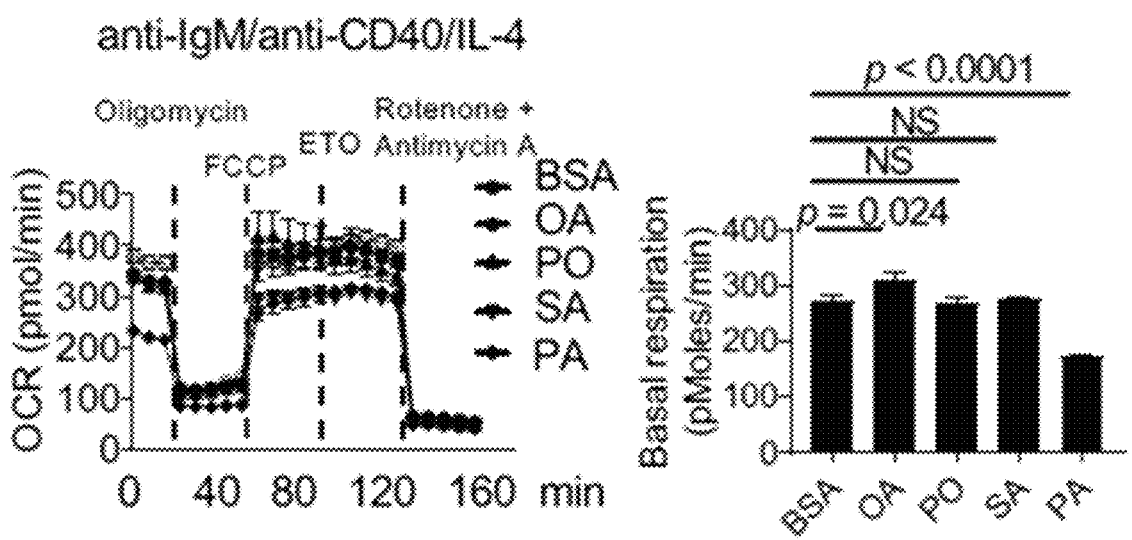

FIGS. 10A-10B. Oxygen consumption rate (OCR) was measured with a Seahorse XFe96 analyzer using LPS/IL-4 (FIG. 10A) and anti-IgM/anti-CD40/IL-4 (FIG. 10B) activated murine B cells in the presence of BSA, OA, PO, SA and PA for 48 h. Basal respiration of either stimulation was summarized. p value was calculated with one-way ANOVA. NS, not significant. Data were representative of 2 (FIG. 10A and FIG. 10B) independent experiments. Error bars represent SEM.

Figure 11A:
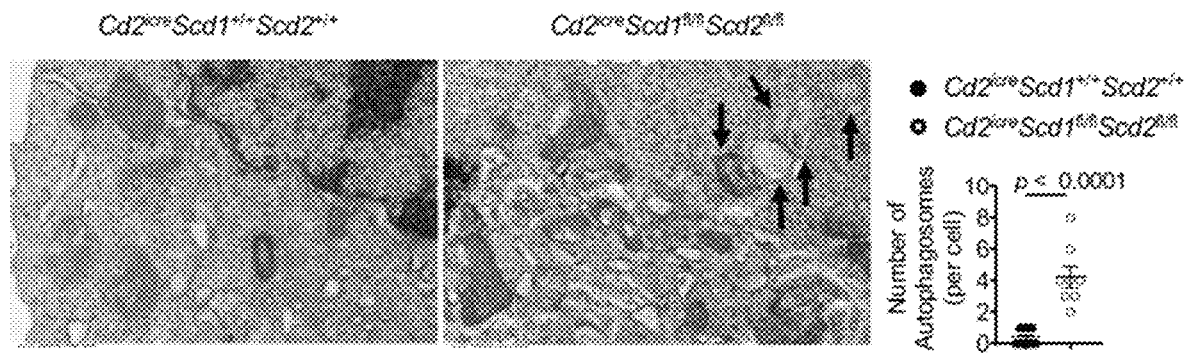
Figure 11B:
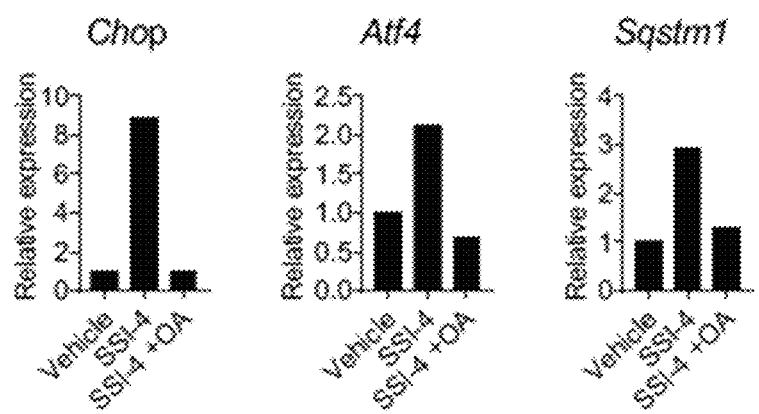

FIGS. 11A-11B. (FIG. 11A) B cells isolated from Cd2$^{iCre}$Scd1$^{+/+}$Scd2$^{+/+}$ and Cd2$^{iCre}$Scd1$^{fl/fl}$Scd2$^{fl/fl}$ mice were activated with LPS/IL-4 for 48 hours. They were imaged on transmission electron microscope. Right, numbers of autophagosomes found in B cells from Cd2$^{iCre}$Scd1$^{+/+}$Scd2$^{+/+}$ mouse (n=10) and those from Cd2$^{iCre}$Scd1$^{fl/fl}$Scd2$^{fl/fl}$ mouse (n=8). (FIG. 11B) Reverse transcription polymerase chain reaction (RT-PCR) analysis of Chop, Atf4, and Sqstm1 in activated B cells in the presence of vehicle, SSI-4, or SSI-4 plus OA.

FIGS. 12A-12E. (FIG. 12A) OA and PO concentration in sera from mice fed with control chow or SSI-4 chow for 2 weeks. OA and PO were detected by GC-MS. (FIG. 12B) Flow cytometry analysis of thymic CD4$^-$CD8$^-$ (DN), CD4$^+$CD8$^+$ (DP), CD4$^+$ single positive (SP) and CD8$^+$ SP T cells from mice fed with control chow or SSI-4 chow. Right, the frequencies of DP, DN, CD4$^+$ and CD8$^+$ SP T cells. (FIG. 12C) Flow cytometry analysis of IgM$^{lo}$IgD$^+$, IgM$^+$IgD$^+$, and IgM$^+$IgD$^{lo}$ B cells among splenic CD19$^+$ B cells. Right, the frequencies of each B cell subsets. (FIG. 12D-FIG. 12E) The frequencies of GC B cells (FIG. 12D) and IgA expression (FIG. 12E) among total B cells in Peyer's patches from mice fed with control or SSI-4 chow. p was calculated with Student's t-test. NS, not significant. Data were representative of 2 (FIG. 12A-FIG. 12E) independent experiments. Error bars represent SEM.

Figure 13:
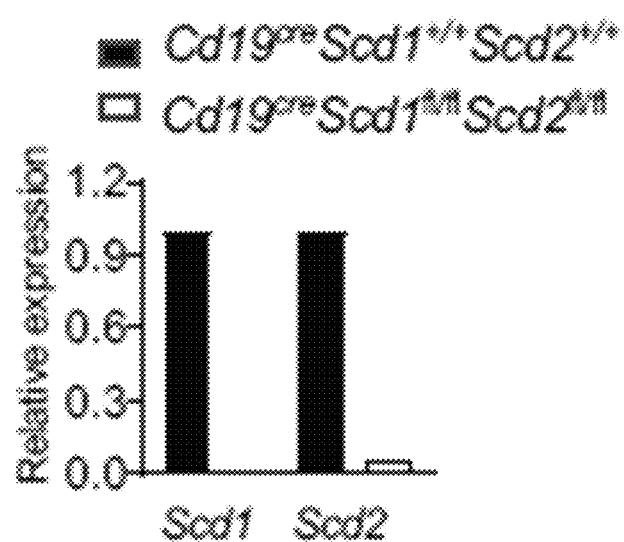

FIG. 13. RT-PCR analysis of Scd1, and Scd2 expression in murine B cells isolated from WT and Cd19$^{Cre}$Scd1$^{fl/fl}$Scd2$^{fl/fl}$ mice.

Figure 14A:
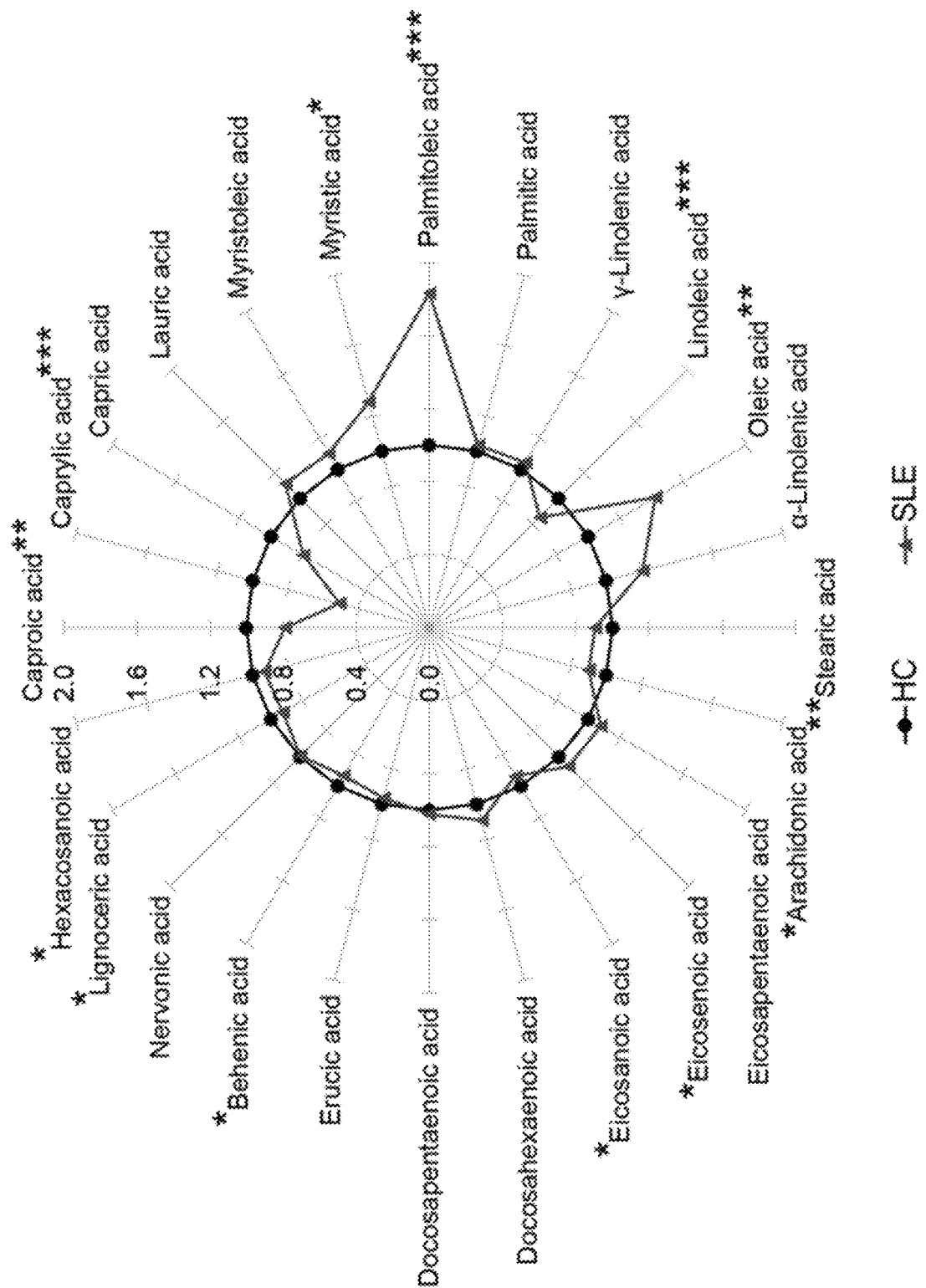

FIGS. 14A-14H. (FIG. 14A) Concentrations of free fatty acids in plasma from healthy donors (HC, dark circles) and lupus patient (SLE, red triangles). Data represents average level of each fatty acid relative to that in the HCs (see, Shin et al., *Metabolomics,* 14:14 (2018)). (FIG. 14B-FIG. 14E) Female MRL/MpJ-Faslpr mice, a classic lupus mouse model, were fed control chow or SSI-4-containing chow (60 mg/kg, on a two-week SSI-4 chow/control-chow alternating schedule) from 6-week old. Urine proteinuria score (FIG. 14B). Kidney histology (H&E staining, scale bar, 20 mm) (FIG. 14C). Ki67+ percentage in B cells (FIG. 14D). MFI of CD98 expression on B cells (FIG. 14E). (FIG. 14F-FIG. 14H) Lupus model was constructed by transferring splenocytes from B6 (C)-H2-Ab1bm12/KhEgJ (bm12) mice to B6.SJL-Ptprca Pepcb/BoyJ (CD45.1+) mice. (FIG. 14F) Serum anti-dsDNA level was measured by ELISA. CXCR5+PD-1+ follicular helper T cell frequency (FIG. 14G) and IgD−CD138+ plasma cell frequency (FIG. 14H) were examined by flow cytometry.

DETAILED DESCRIPTION

This document provides methods and materials for treating autoimmune diseases. For example, this document provides methods and materials for using one or more SCD1 polypeptide inhibitors to treat mammals (e.g., humans) having an autoimmune disease (e.g., a systemic autoimmune disease such as lupus). In some cases, a mammal (e.g., a human) having an autoimmune disease (e.g., a systemic autoimmune disease such as lupus), the mammal can be administered, or can be instructed to self-administer, any one or more (e.g., 1, 2, 3, 4, 5, 6, or more) SCD1 polypeptide inhibitors.

A SCD1 polypeptide inhibitor can be any appropriate type of molecule (e.g., small molecules, nucleic acid molecules designed to induce RNA interference (e.g., a siRNA molecule or a shRNA molecule), antisense molecules, miRNAs, and antibodies (e.g., antibodies (e.g., monoclonal antibodies)). A SCD1 polypeptide inhibitor can be an inhibitor of SCD1 polypeptide expression or an inhibitor of SCD1 polypeptide activity. Examples of SCD1 polypeptide inhibitors include, without limitation, MF438, A939572, CAY10566, MF-438, CVT-11127, CVT-12012, T-3764518, BZ36, SW208108, SW203668, MK-8245, and arachidyl amido cholanoic acid (e.g., Aramchol™). In some cases, a SCD1 polypeptide inhibitor can be readily designed based upon the nucleic acid and/or polypeptide sequences of SCD1. Examples of SCD1 nucleic acid and polypeptide sequences include, without limitation, those sequences set forth in the National Center for Biotechnology Information (NCBI) database under GenBank® accession no. NM 005063 (version NM 005063.5), accession no. XM_001723785, accession no. XM_001725202, NC_000010 (version NC_000010.11), accession no. AB032261 (version AB032261.1), and accession no. AB208982 (version AB208982.1). In some cases, a SCD1 polypeptide inhibitor can be as described elsewhere (see, e.g., WO 2016/022955).

In some cases, a SCD1 polypeptide inhibitor can have Formula (I):

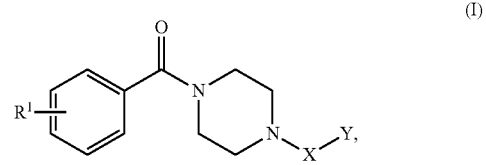

or a pharmaceutically acceptable salt thereof, where $R^1$ is an unsubstituted $C_{1-6}$alkyl or $C_{1-6}$haloalkyl; X is

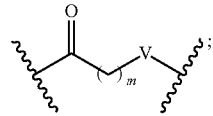

Y is selected from:

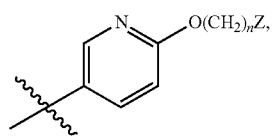 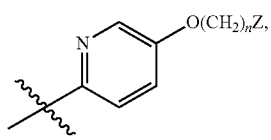

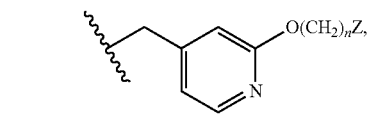

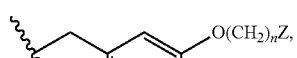

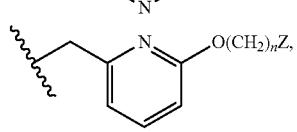

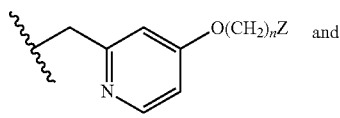 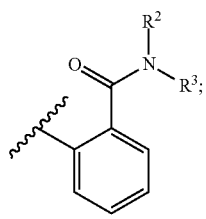

m is 0 or 1; n is 0, 1, or 2; V is $NR^4$ or O; $R^2$, $R^3$, and $R^4$ are each independently H or an unsubstituted $C_{1-6}$alkyl; and Z is an unsubstituted aryl. In some cases, a SCD1 polypeptide inhibitor according to Formula (I) can have the structure of Formula (Ia):

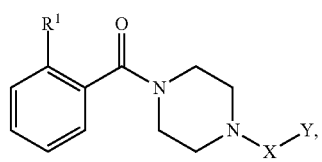

(Ia)

or a pharmaceutically acceptable salt thereof. Representative examples of SCD1 polypeptide inhibitors according to Formula (I) and/or Formula (Ia) include, without limitation:

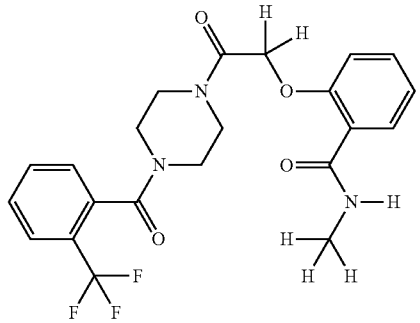

SSI-1

(N-Methyl-2-(2-oxo-2-{4-[2-(trifluoromethyl)benzoyl]piperazin-1-yl}ethoxy)benzamide) or a pharmaceutically acceptable salt thereof;

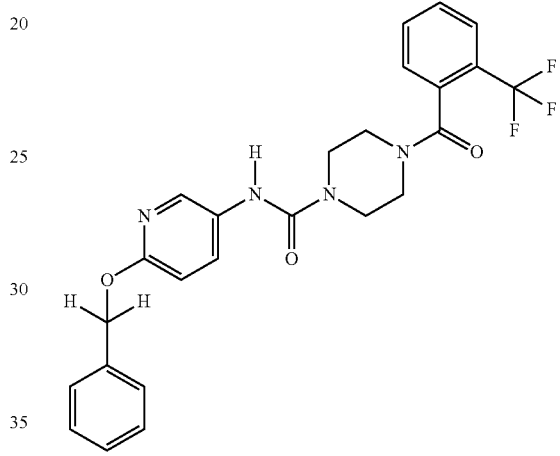

SSI-2

(2-(benzyloxy)-5-{[hydroxy({4-[2-(trifluoromethyl)benzoyl]piperazin-1-yl})methyl]amino}-1,2-dihydropyridin-2-ylium-1-ide) or a pharmaceutically acceptable salt thereof; and

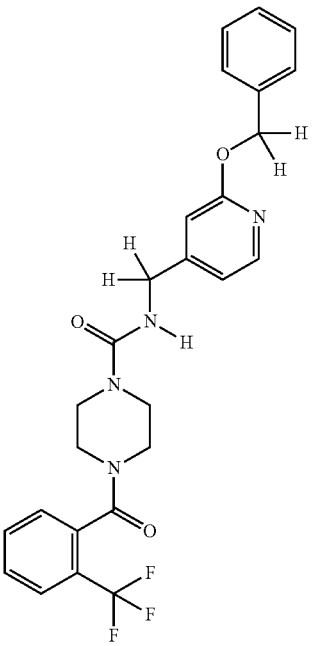

SSI-3

(2-(benzyloxy)-4-({[hydroxy({4-[2-(trifluoromethyl)benzoyl]piperazin-1-yl})methyl]azanidyl}methyl)-1,2-dihydropyridin-2-ylium-1-ide) or a pharmaceutically acceptable salt thereof.

In some cases, a SCD1 polypeptide inhibitor can have Formula (II):

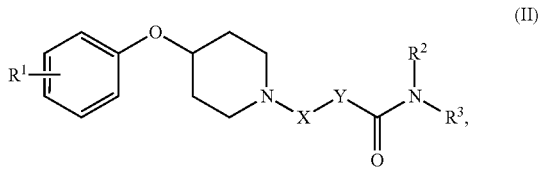

or pharmaceutically acceptable salt thereof, where $R^1$ is halo; X is —(C=O)NR$^4$—; Y is

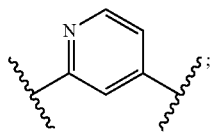 [SMILES: *c1ccnc(*)c1]

$R^2$, $R^3$, and $R^4$ are each independently H or an unsubstituted $C_{1-6}$alkyl. In some cases, a SCD1 polypeptide inhibitor according to Formula (II) can have the structure of Formula (IIa):

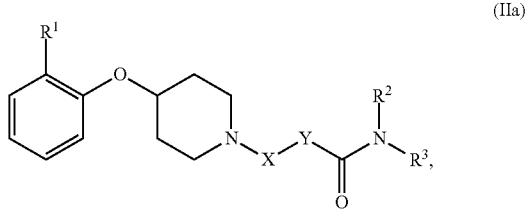

or pharmaceutically acceptable salt thereof. A representative example of a SCD1 polypeptide inhibitor according to Formula (II) and/or Formula (IIa) include:

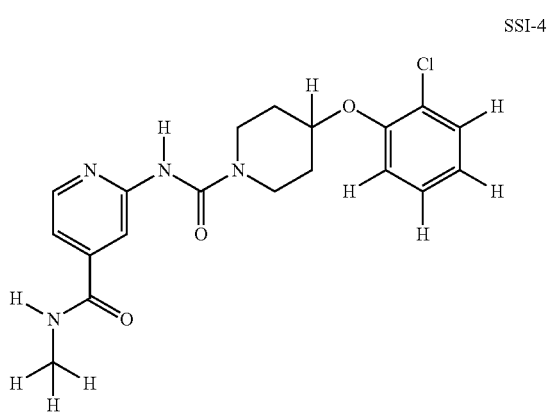 [SMILES: CNC(=O)c1ccnc(NC(=O)N2CCC(Oc3ccccc3Cl)CC2)c1]

SSI-4

(2-{[4-(2-Chlorophenoxy)piperidine-1-carbonyl]amino}-N-methylpyridine-4-carboxamide) or pharmaceutically acceptable salt thereof.

Any mammal having an autoimmune disease (e.g., a systemic autoimmune disease such as lupus) can be treated as described herein (e.g., by administering one or more SCD1 polypeptide inhibitors such as SSI-4). Examples of mammals that can have an autoimmune disease and can be treated as described herein include, without limitation, humans, non-human primates (e.g., monkeys), dogs, cats, horses, cows, pigs, sheep, mice, and rats. In some cases, a human having lupus (e.g., SLE) can be treated as described herein.

When treating a mammal (e.g., a human) having an autoimmune disease (e.g., a systemic autoimmune disease such as lupus) as described herein (e.g., by administering one or more SCD1 polypeptide inhibitors such as SSI-4), the autoimmune disease can be any type of autoimmune disease. In some cases, an autoimmune disease can be lupus. Examples of autoimmune diseases that can be treated as described herein include, without limitation, SLE, cutaneous lupus, drug-induced lupus, neonatal lupus, rheumatoid arthritis, spondyloarthropathy, Sjogren's syndrome, polymyositis, dermatomyositis, scleroderma, and multiple sclerosis. In some cases, an autoimmune disease treated as described herein can be lupus (e.g., SLE).

In some cases, the methods described herein can include identifying a mammal (e.g., a human) as having an autoimmune disease (e.g., a systemic autoimmune disease such as lupus). Any appropriate method can be used to identify a mammal as having an autoimmune disease (e.g., a systemic autoimmune disease such as lupus). For example, laboratory tests such as blood tests (e.g., antinuclear antibody (ANA) tests and/or blood tests to determine complete blood count, erythrocyte sedimentation rate, cytokine concentration, kidney function, and/or liver function) and/or urine tests (e.g., to evaluate protein level and/or red blood cells in the urine), and/or imaging tests (e.g., chest X-ray and/or echocardiogram) can be used to identify mammals (e.g., humans) having an autoimmune disease (e.g., a systemic autoimmune disease such as lupus).

In some cases, one or more SCD1 polypeptide inhibitors (e.g., SSI-4) can be administered to a mammal in need thereof (e.g., a mammal having an autoimmune disease such as lupus) to reduce or eliminate one or more symptoms of an autoimmune disease. For example, one or more SCD1 polypeptide inhibitors described herein can be administered to a mammal having an autoimmune disease as described herein to reduce of a symptom of an autoimmune disease within the mammal by, for example, at least 10, at least 20, at least 30, at least 40, at least 50, at least 60, at least 70, at least 80, at least 90, at least 95, or more percent. Examples of signs and symptoms of an autoimmune disease that can be reduced by one or more SCD1 polypeptide inhibitors include, without limitation, fatigue, fever, joint pain, joint stiffness, joint swelling, rash (e.g., butterfly-shaped rash (e.g., a rash on the face that covers the cheeks and bridge of the nose), or rash elsewhere on the body), skin lesions that appear or worsen with sun exposure (photosensitivity), fingers and toes that turn white or blue when exposed to cold or during stressful periods (Raynaud's phenomenon), shortness of breath, chest pain, dry eyes, headaches, confusion, and memory loss.

In some cases, one or more SCD1 polypeptide inhibitors (e.g., SSI-4) can be administered to a mammal in need thereof (e.g., a mammal having an autoimmune disease such as lupus) to reduce or eliminate proliferation of B cells within the mammal. For example, one or more SCD1 polypeptide inhibitors described herein can be administered to a mammal having an autoimmune disease as described herein to reduce proliferation of B cells within the mammal by, for example, at least 10, at least 20, at least 30, at least 40, at least 50, at least 60, at least 70, at least 80, at least 90, at least 95, or more percent. Any appropriate method can be used to identify proliferation of B cells within the mammal. For example, B cell count, B cell activation markers (e.g., CD27), proliferation markers (e.g., ki67), CellTrace Violet proliferation dye, and/or 3 [H]-thymidine incorporation can be used to identify proliferation of B cells within the mammal.

In some cases, one or more SCD1 polypeptide inhibitors (e.g., SSI-4) can be administered to a mammal in need thereof (e.g., a mammal having an autoimmune disease such as lupus) to reduce or eliminate antibody production by B cells within the mammal. For example, one or more SCD1 polypeptide inhibitors described herein can be administered to a mammal having an autoimmune disease as described herein to reduce antibody production by B cells within the mammal by, for example, 10, 20, 30, 40, 50, 60, 70, 80, 90, 95, or more percent. Any appropriate method can be used to identify antibody production by B cells within the mammal. For example, expression of immunoglobulin on B cells and/or levels of different immunoglobulin isotypes in plasma/serum can be used to identify antibody production by B cells within the mammal.

In some cases, one or more SCD1 polypeptide inhibitors (e.g., SSI-4) can be administered to a mammal in need thereof (e.g., a mammal having an autoimmune disease such as lupus) to reduce or eliminate biosynthesis of one or more (e.g., 1, 2, 3, 4, 5, 6, or more) fatty acids within the mammal. For example, one or more SCD1 polypeptide inhibitors described herein can be administered to a mammal having an autoimmune disease as described herein to biosynthesis of one or more fatty acids within the mammal. For example, one or more SCD1 polypeptide inhibitors described herein can be administered to a mammal having an autoimmune disease as described herein to reduce the serum concentration of one or more fatty acids within the mammal. For example, one or more SCD1 polypeptide inhibitors described herein can be administered to a mammal having an autoimmune disease as described herein to reduce a level of one or more fatty acids within the mammal by, for example, 10, 20, 30, 40, 50, 60, 70, 80, 90, 95, or more percent. One or more SCD1 polypeptide inhibitors can be effective to reduce or eliminate biosynthesis of any type of fatty acid(s) within the mammal. In some cases, a fatty acid can be a monounsaturated fatty acid (MUFA). In some cases, a fatty acid can be a polyunsaturated fatty acid (PUFA). In some cases, a fatty acid can be a saturated fatty acid. In some cases, a fatty acid can be a non-esterified free fatty acid (NEFA). Examples of fatty acids that the biosynthesis of can be reduced or eliminated by one or more SCD1 polypeptide inhibitors described herein include, without limitation, palmitoleic acid (PO), oleic acid (OA), and vaccenic acid. Any appropriate method can be used to determine a level of a fatty acid (e.g., a serum concentration of a fatty acid) within the mammal. For example, mass spectrometry (MS) techniques (e.g., liquid chromatography MS (LC/MS) and gas chromatography MS (GC/MS)) can be used to identify a level of a fatty acid within the mammal.

In some cases, one or more SCD1 polypeptide inhibitors (e.g., SSI-4) can be administered to a mammal (e.g., human) identified as having an autoimmune disease (e.g., a systemic autoimmune disease such as lupus) as the sole active agent for treating the autoimmune disease. For example, SSI-4 can be administered to a mammal identified as having an autoimmune disease (e.g., a systemic autoimmune disease such as lupus) as the sole active agent for treating the autoimmune disease.

In some cases, one or more SCD1 polypeptide inhibitors can be administered to a mammal (e.g., human) identified as having an autoimmune disease (e.g., a systemic autoimmune disease such as lupus) together with one or more additional treatments (e.g., therapeutic agents) used to treat an autoimmune disease. In some cases, a therapeutic agent that can be used to treat an autoimmune disease can be an anti-inflammatory (e.g., a nonsteroidal anti-inflammatory drug (NSAID)). In some cases, a therapeutic agent that can be used to treat an autoimmune disease can be an antimalarial drug. In some cases, a therapeutic agent that can be used to treat an autoimmune disease can be a steroid (e.g., a corticosteroid). In some cases, a therapeutic agent that can be used to treat an autoimmune disease can be an immunosuppressant. In some cases, a therapeutic agent that can be used to treat an autoimmune disease can be a biologic. Examples of therapeutic agents that can be used in combination with one or more SCD1 polypeptide inhibitors (e.g., SSI-4) to treat an autoimmune disease include, without limitation, naproxen sodium (e.g., Aleve®), ibuprofen (e.g., Advil®), hydroxychloroquine (Plaquenil®), prednisone, methylprednisolone, azathioprine (e.g., Imuran®, and Azasan®), mycophenolate mofetil (e.g., CellCept®), methotrexate (e.g., Trexall®), belimumab (e.g., Benlysta), rituximab (e.g., Rituxan), vitamin D, calcium, dehydroepiandrosterone (DHEA), omega-3 fatty acids, tocilizumab (Actemra), sirukumab, siltuximab (SYLVANT®), and anifrolumab. In cases where one or more SCD1 polypeptide inhibitors described herein are used in combination with one or more therapeutic agents to treat an autoimmune disease, the one or more SCD1 polypeptide inhibitors can be administered at the same time or independently of the administration of one or more therapeutic agents. For example, the composition including one or more SCD1 polypeptide inhibitors can be administered before, concurrent with, or after the one or more therapeutic agents are administered.

In some cases, one or more SCD1 polypeptide inhibitors described herein (e.g., SSI-4) can be administered to a mammal (e.g., a mammal identified as having an autoimmune disease such as lupus) once or multiple times over a period of time ranging from days to weeks.

In some cases, one or more SCD1 polypeptide inhibitors described herein (e.g., SSI-4) can be formulated into a pharmaceutically acceptable composition for administration to a mammal (e.g., a mammal identified as having an autoimmune disease such as lupus). For example, a therapeutically effective amount of one or more SCD1 polypeptide inhibitors can be formulated together with one or more pharmaceutically acceptable carriers (additives) and/or diluents. A pharmaceutical composition can be formulated for administration in solid or liquid form including, without limitation, sterile solutions, suspensions, sustained-release formulations, tablets, capsules, pills, powders, and granules. Pharmaceutically acceptable carriers, fillers, and vehicles that may be used in a pharmaceutical composition described herein include, without limitation, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A pharmaceutical composition containing one or more SCD1 polypeptide inhibitors described herein (e.g., SSI-4) can be designed for oral or parenteral (including subcutaneous, intramuscular, intravenous, and intradermal) administration. When being administered orally, a pharmaceutical composition can be in the form of a pill, tablet, or capsule. Compositions suitable for parenteral administration include aqueous and non-aqueous sterile injection solutions that can contain anti-oxidants, buffers, bacteriostats, and solutes that render the formulation isotonic with the blood of the intended recipient. The formulations can be presented in unit-dose or multi-dose containers, for example, sealed ampules and vials, and may be stored in a freeze dried (lyophilized) condition requiring only the addition of the sterile liquid carrier, for example, water for injections, immediately prior to use. Extemporaneous injection solutions and suspensions may be prepared from sterile powders, granules, and tablets.

A pharmaceutically acceptable composition including one or more SCD1 polypeptide inhibitors described herein (e.g., SSI-4) can be administered locally or systemically.

Effective doses can vary depending on the risk and/or the severity of the autoimmune disease, the route of administration, the age and general health condition of the mammal, excipient usage, the possibility of co-usage with other therapeutic treatments such as use of other agents, and the judgment of the treating physician.

An effective amount of a composition containing one or more SCD1 polypeptide inhibitors described herein (e.g., SSI-4) can be any amount that effectively treats the mammal (e.g., reduces or eliminates one or more symptoms of an autoimmune disease within the mammal) without producing significant toxicity to the mammal. In some cases, an effective amount of one or more SCD1 polypeptide inhibitors can be from about 10 to about 500 mg per kg body weight (mg/kg) of the mammal being treated. For example, an effective amount of one or more SCD1 polypeptide inhibitors can be from about 10 to about 400, from about 10 to about 300, from about 10 to about 200, from about 10 to about 100, from about 10 to about 75, from about 10 to about 50, from about 10 to about 30, from about 25 to about 500, from about 50 to about 500, from about 100 to about 500, from about 200 to about 500, from about 300 to about 500, from about 15 to about 400, from about 20 to about 300, from about 25 to about 250, from about 30 to about 200, from about 35 to about 150, from about 40 to about 100, or from about 45 to about 75 mg/kg of the mammal being treated. In some cases, about 30 mg/kg of one or more SCD1 polypeptide inhibitors can be administered (e.g., orally administered) to a human having an autoimmune disease (e.g., lupus). In some cases, about 60 mg/kg of one or more SCD1 polypeptide inhibitors can be administered (e.g., orally administered) to a human having an autoimmune disease (e.g., lupus).

If a particular mammal fails to respond to a particular amount, then the amount of one or more SCD1 polypeptide inhibitors described herein (e.g., SSI-4) can be increased by, for example, two fold. After receiving this higher amount, the mammal can be monitored for both responsiveness to the treatment and toxicity symptoms, and adjustments made accordingly. The effective amount can remain constant or can be adjusted as a sliding scale or variable dose depending on the mammal's response to treatment. Various factors can influence the actual effective amount used for a particular application. For example, the frequency of administration, duration of treatment, use of multiple treatment agents, route of administration, and severity of the condition (e.g., an autoimmune disease such as lupus) may require an increase or decrease in the actual effective amount administered.

The frequency of administration of one or more SCD1 polypeptide inhibitors described herein (e.g., SSI-4) can be any amount that effectively treats the mammal (e.g., reduces or eliminates one or more symptoms of an autoimmune disease within the mammal) without producing significant toxicity to the mammal. For example, the frequency of administration of one or more SCD1 polypeptide inhibitors can be from about two to about three times a week to about two to about three times a month. In some cases, a mammal identified as having a SCD1-associated cancer and/or identified as having a cancer that is likely to be responsive to one or more SCD1 polypeptide inhibitors can receive a single administration of one or more SCD1 polypeptide inhibitors described herein. The frequency of administration of one or more SCD1 polypeptide inhibitors described herein can remain constant or can be variable during the duration of treatment. A course of treatment with a composition containing one or more SCD1 polypeptide inhibitors described herein can include rest periods. For example, a composition containing one or more SCD1 polypeptide inhibitors described herein can be administered every other month over a two-year period followed by a six-month rest period, and such a regimen can be repeated multiple times. As with the effective amount, various factors can influence the actual frequency of administration used for a particular application. For example, the effective amount, duration of treatment, use of multiple treatment agents, route of administration, and severity of the condition (e.g., an autoimmune disease such as lupus) may require an increase or decrease in administration frequency.

An effective duration for administering a composition containing one or more SCD1 polypeptide inhibitors (e.g., SSI-4) can be any duration that effectively treats the mammal (e.g., reduces or eliminates one or more symptoms of an autoimmune disease within the mammal) without producing significant toxicity to the mammal. In some cases, the effective duration can vary from several months to several years to a lifelong treatment. Multiple factors can influence the actual effective duration used for a particular treatment. For example, an effective duration can vary with the frequency of administration, effective amount, use of multiple treatment agents, route of administration, and severity of the condition being treated.

The invention will be further described in the following examples, which do not limit the scope of the invention described in the claims.

EXAMPLES

Example 1: Stearoyl-CoA Desaturase Mediated Monounsaturated Fatty Acid Availability Supports Humoral Immunity This Example presents evidence that B cell development and activation require SCD generated MUFA, particularly OA, which maintains B cell metabolic fitness partly by supporting mitochondrial oxidative phosphorylation and mTORC1 activity, and preventing excessive autophagy and ER stress. In vivo, B cells mainly rely on B cell-extrinsic SCD activity to provide MUFAs. The immune response enhances MUFA availability, partly through SCD activity, which is required for sustaining antibody production. Suppression of SCD reduces humoral immune response to immunization, and weakens immune defense against influenza A virus. Together the results in this Example provide a link between metabolism of a specific FA specie to humoral immunity in immunization and anti-influenza immune defense.

SCD Mediated MUFA Biosynthesis is Activated During B Cell Activation

Figure 1A:
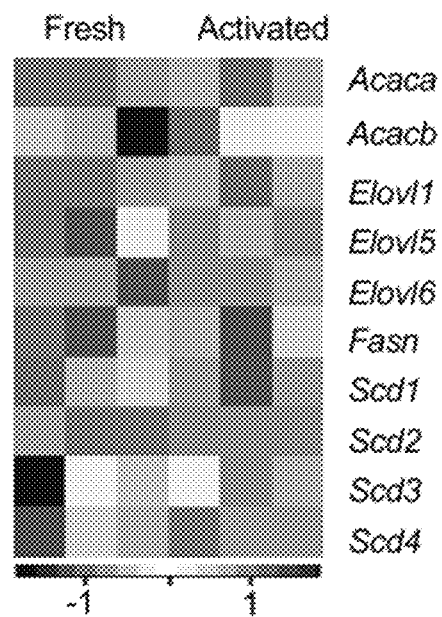
FIGS. 1A-1H. SCD mediated MUFA biosynthesis during B cell activation in vitro.
Figure 1B:
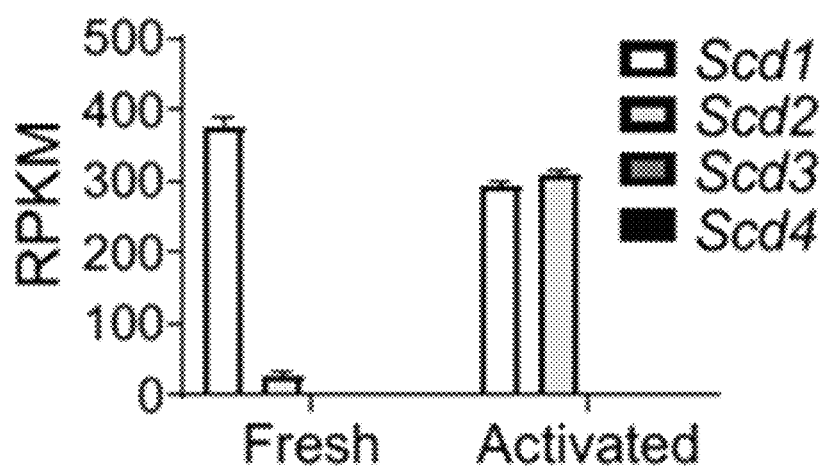
Figure 1C:
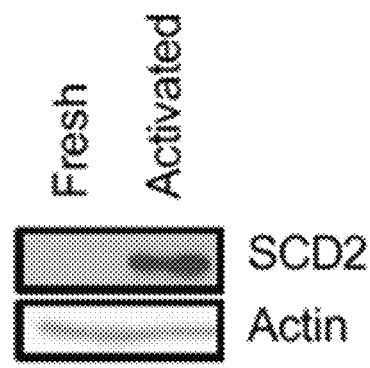
Figure 1D:
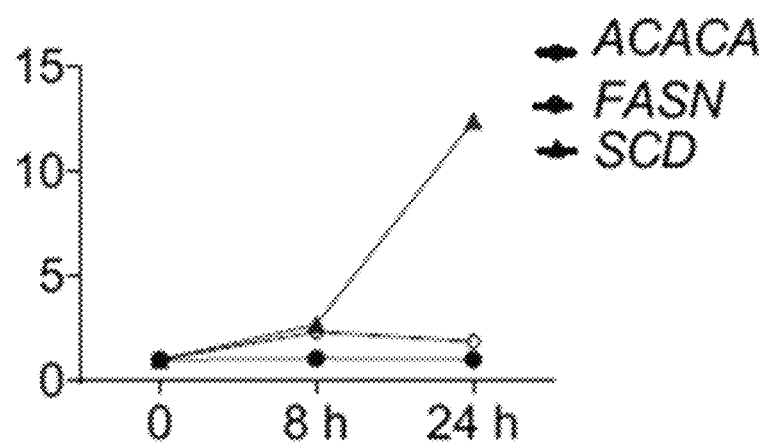
Figure 1E:
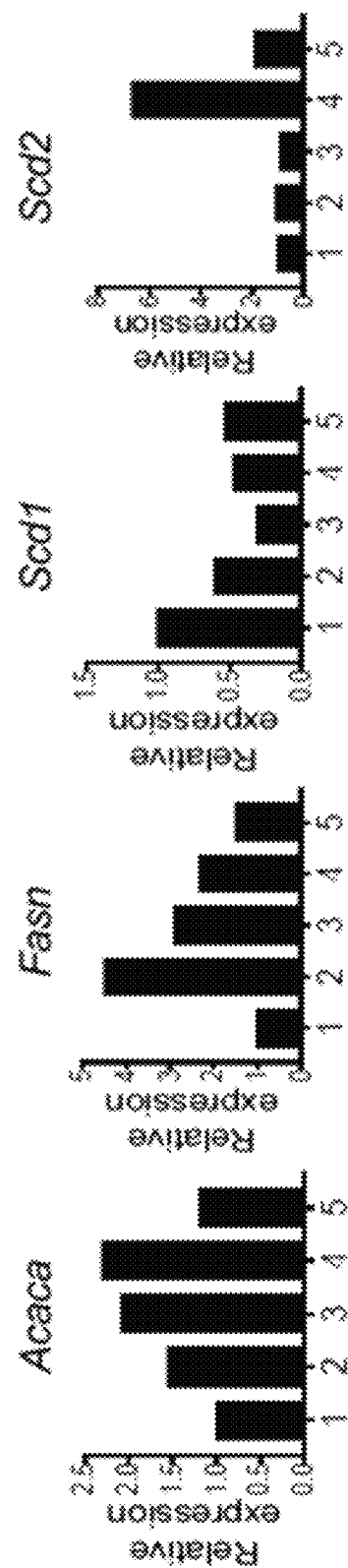

It was sought to determine the FA biosynthesis gene expression program during B cell activation. RNA sequencing was performed using fresh murine B cells and LPS/IL-4 activated B cells. Major genes involved in FA biosynthesis, including Acaca, Elovl1, Elovl5, Elovl6, Fasn and Scd2, were all increased (FIG. 1A). Among the 4 murine Scd genes, Scd3 and Scd4 were below detection limit. Scd1 expression was slightly reduced, while Scd2 expression was substantially increased (FIG. 1B). The increase of Scd2 expression was also confirmed by immunoblot (FIG. 1C). A similar dynamic occurred during the first 24 hours of activation, in which Scd2 expression showed the most upregulation after 24 hours stimulation (FIG. 8A). The induction of SCD2 was not specific to LPS/IL-4 stimulation, because anti-IgM, anti-CD40 and CpG, but not IL-4 alone, also induced SCD2 protein expression at 24 hours after activation (FIG. 8B). Furthermore, activation of human B cells also induced robust SCD expression (FIG. 1D). Finally, the upregulation of FA biosynthesis genes was dependent on mTORC1 signaling, as rapamycin treatment blocked their increased expression (FIG. 1E), consistent with the anabolic function of mTORC1 on lipid biosynthesis. Thus, antigenic stimulation of B cells activates FA biosynthetic pathway in an mTORC1 dependent manner.

Figure 1F:
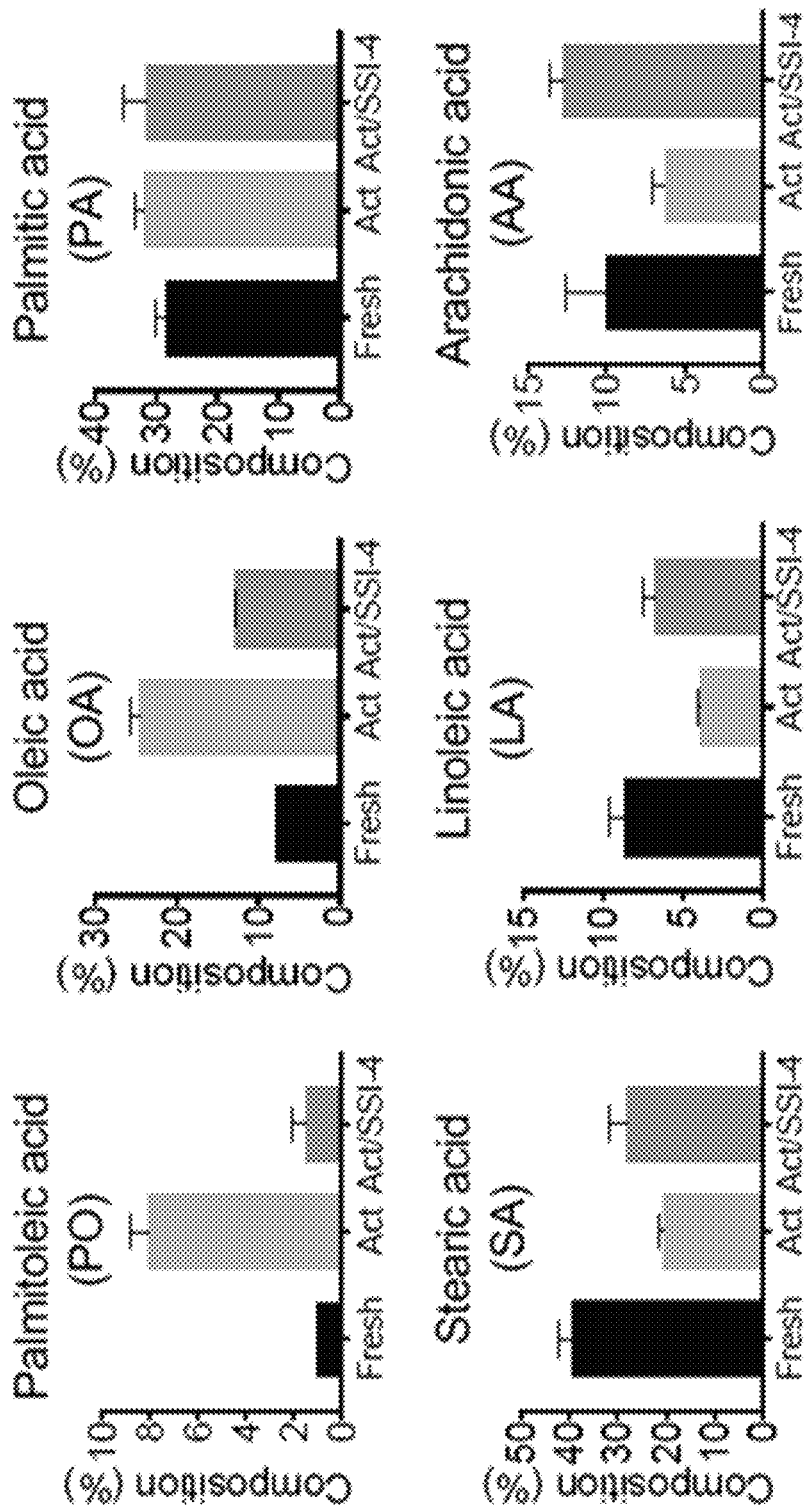
Figure 1G:
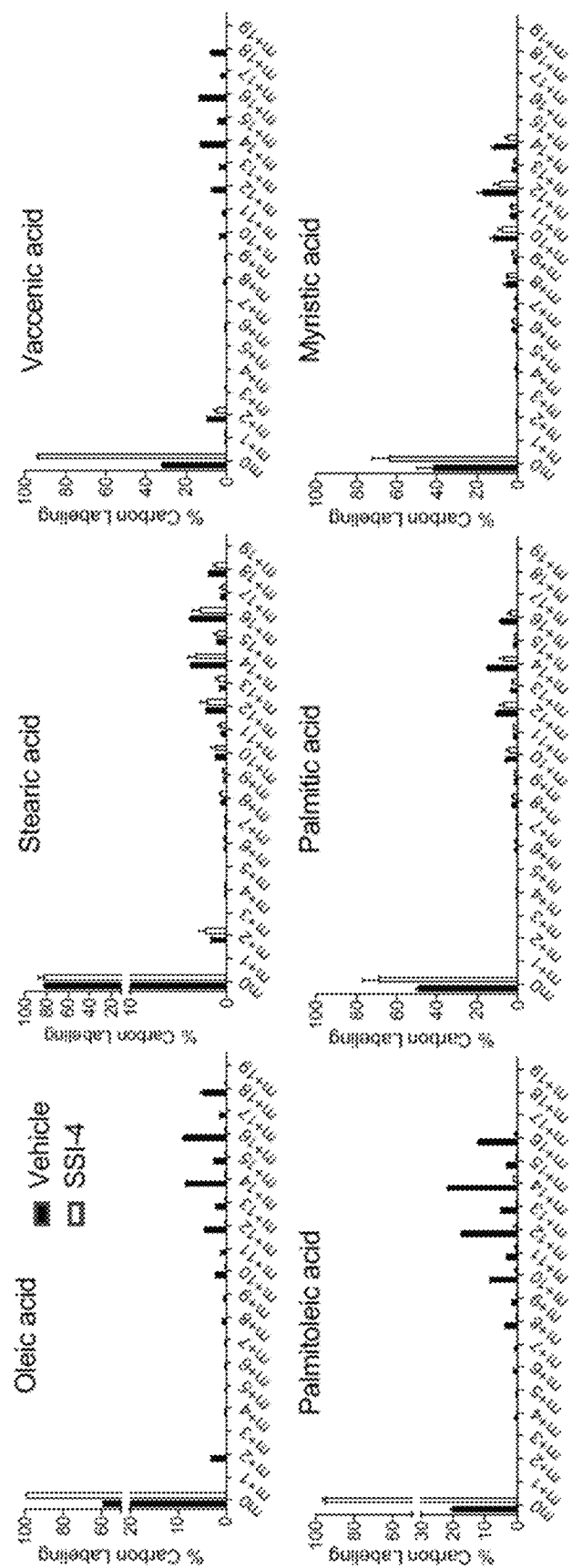
Figure 1H:
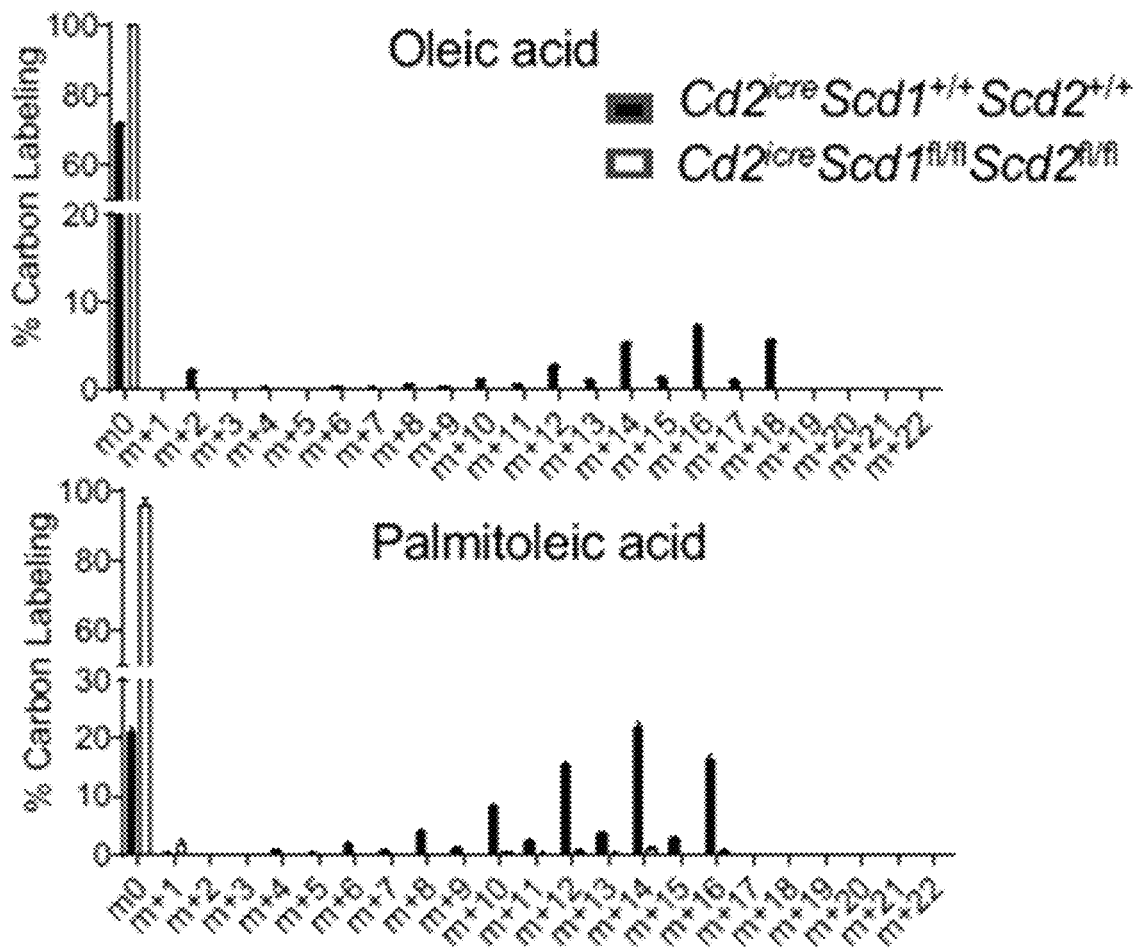

To further examine the functional outcome of increased FA biosynthesis gene expression, triple quadrupole liquid chromatography/tandem mass spectrometry (LC-MS/MS) was employed to examine specific FA content in fresh and activated B cells. The targeted metabolomics showed that PO and OA, the main MUFAs produced by SCD, exhibited the highest increase of their relative contents in activated B cells compared to unstimulated B cells. The composition of palmitic acid (PA), the precursor of PO, did not change substantially, while the composition of stearic acid (SA), the precursor of OA and the PUFAs, including linoleic acid (LA) and arachidonic acid (AA), modestly reduced after activation (FIG. 1F). This dramatic accumulation of MUFAs was dependent on SCD activity, because treatment with an SCD specific inhibitor, SSI-4, largely reversed it (FIG. 1F). Furthermore, the de novo biosynthesis of FAs from glucose was confirmed in a U-$^{13}$C-6-glucose tracing experiment. When B cells were activated in medium containing uniformly $^{13}$C labeled glucose, the LC-MS/MS assay detected substantial $^{13}$C incorporation in OA, PO and vaccenic acid (VA, another MUFA), which were all abolished when cells were treated with SSI-4. However, the incorporation of $^{13}$C into SA, PA and myristic acid (MA) was largely unaffected by SSI-4 treatment (FIG. 1G). These observations were further confirmed using a genetic model, in which Scd1 and Scd2 were deleted in B cells through Cd2iCre, an optimized variant of Cre recombinase under human CD2 promoter and locus control region that leads to efficient recombination in lymphocytes. SCD1 and SCD2 deficiency completely eliminated $^{13}$C-glucose incorporation into OA, PO and VA, but did not substantially affect $^{13}$C incorporation into PA, SA, or MA (FIG. 1H, and FIG. 8C). Incorporation of $^{13}$C into other PUFAs, including arachidonic acid, linoleic acid and α-linolenic acid, was not detected in the assays, suggesting that B cells do not have the capacity to generate these FAs from glucose de novo. Therefore, these results showed that B cell activation is associated with activation of SCD activity and increased proportion of SCD-generated MUFA content.

SCD-Generated MUFA Supports B Cell Proliferation and Class Switch In Vitro

Figure 2A:
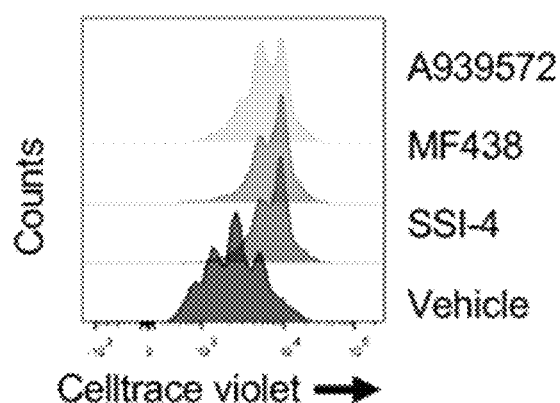
FIGS. 2A-2G. SCD-generated MUFA is required for B cell proliferation and class switch in vitro.
Figure 2B:
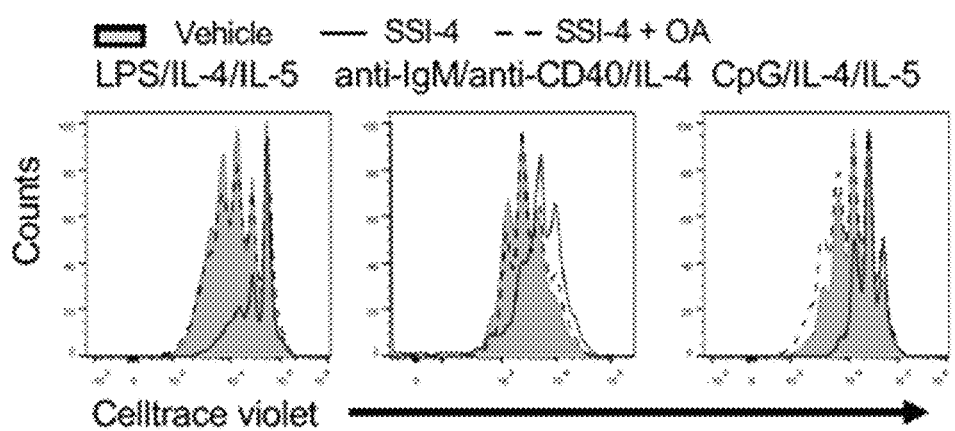
Figure 2C:
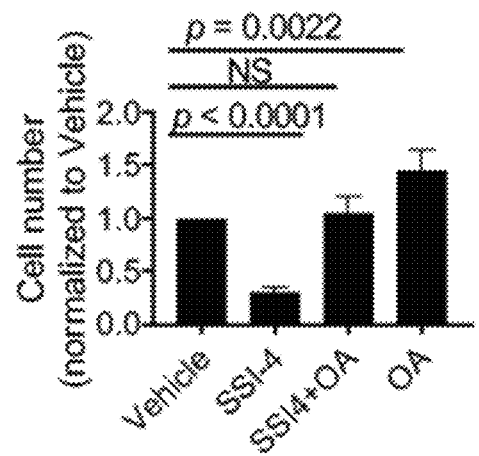
Figure 2D:
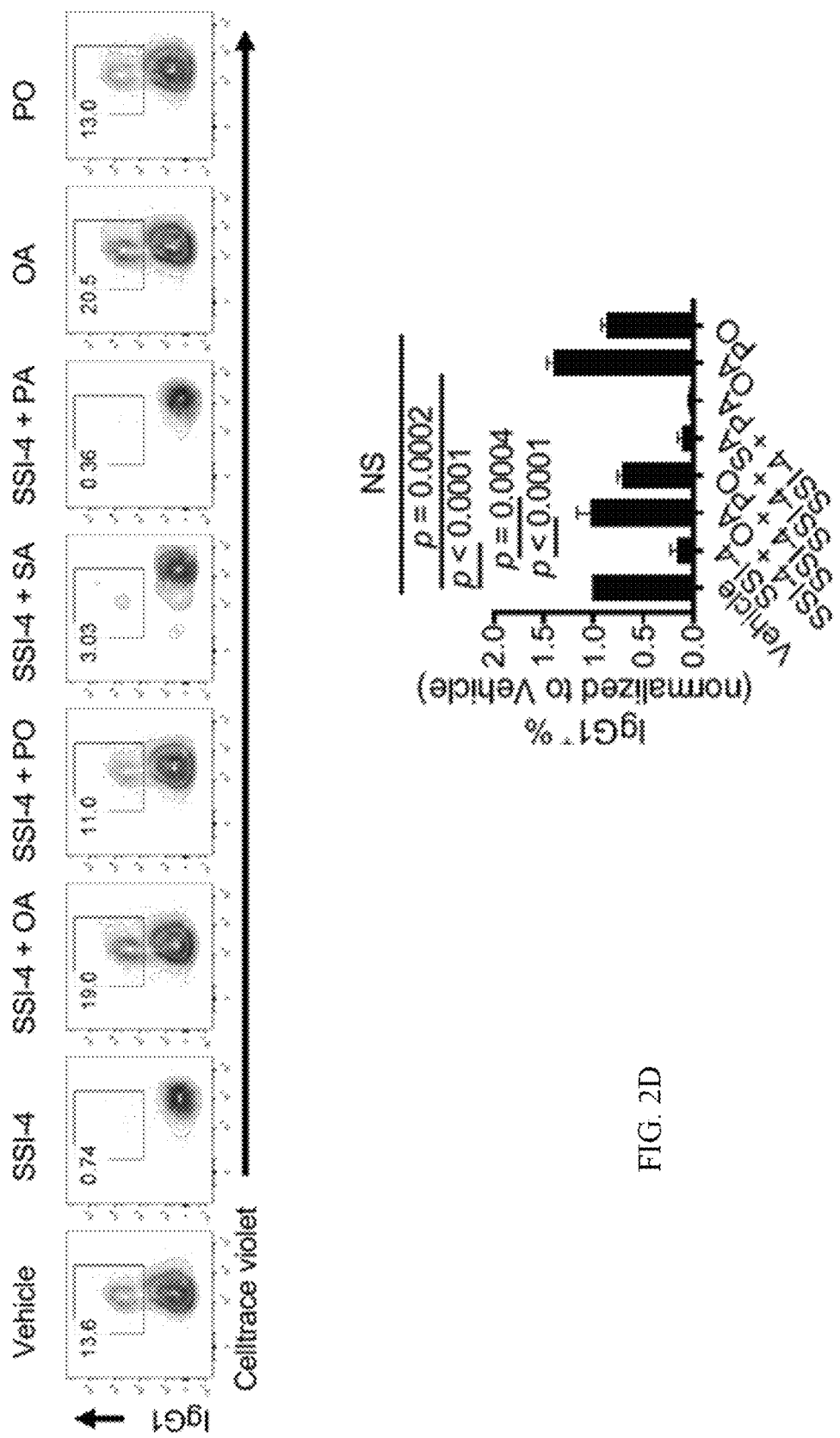
Figure 2E:
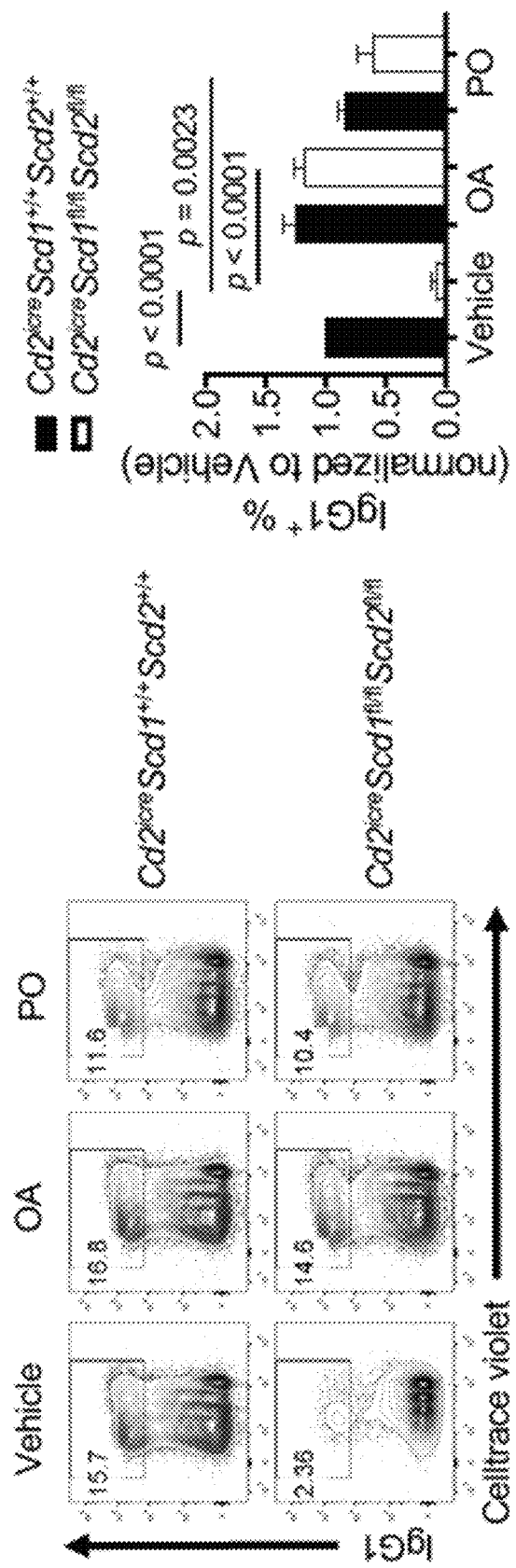
Figure 2F:
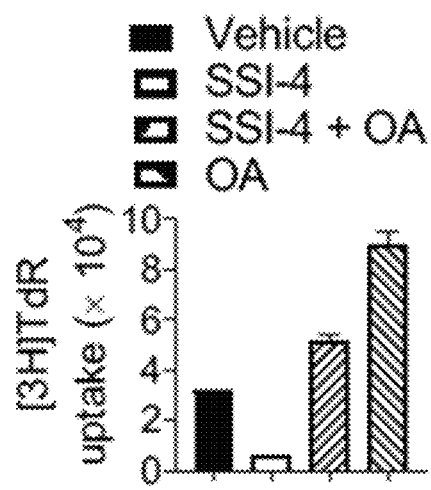
Figure 2G:
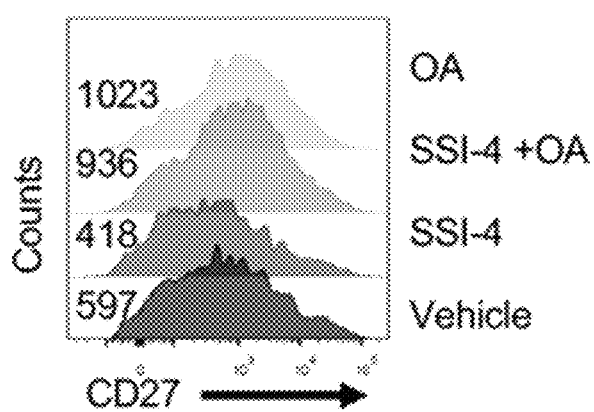

To further investigate the impact of SCD generated MUFA on B cell functions, the proliferation of mouse B cells activated with LPS/IL-4 was measured in the presence of different SCD inhibitors, including SSI-4, MF438, and A939572. All were capable of inhibiting B cell proliferation (FIG. 2A). Importantly, exogenous OA was able to rescue the proliferation defects caused by SCD inhibition, and promote cell number accumulation, demonstrating that the enzymatic activity of SCD is required for B cell proliferation (FIG. 2B, C). Similar phenotypes were observed when B cells were stimulated with anti-IgM/anti-CD40 or TLR9 ligand, CpG (FIG. 2B). LPS/IL-4 also stimulates class switch to IgG1. It was found that SCD inhibition strongly suppressed IgG1 class switch (FIG. 2D). Exogenous OA alone further enhanced B cell proliferation (measured by cell number (FIG. 2C)) and IgG1 class switch, and it could fully restore both parameters upon SSI-4 treatment (FIG. 2C, D). In contrast, PO alone did not improve class switch and had a substantial, but incomplete, rescue effects on proliferation and IgG1 class switch upon SSI-4 treatment. PA and SA showed no rescue effects upon SSI-4 treatment (FIG. 2D). Moreover, unlike OA, supply of exogenous PA and SA were unable to promote the proliferation and class switch (FIG. 9A). Of note, the concentration of exogenous FAs applied in these in vitro assays was based on the levels of serum non-esterified fatty acids (NEFAs) in WT mice (Table 1). These results suggest that proliferating B cells preferentially utilize MUFA, especially OA, rather than SFAs. Moreover, splenic B cells were isolated from Scd1 and Scd2 deficient mice and stimulated them with LPS/IL-4. SCD1/2 deficient B cells proliferated poorly, had highly reduced IgG1 class switch compared to those from control mice. Exogenous OA fully restored proliferation and IgG1 class switch, while PO had a partial rescue effect (FIG. 2E). Lastly, these observations were confirmed using human B cells isolated from peripheral blood mononuclear cells (PBMC) of healthy donors. Exogenous OA promoted human B cell proliferation (FIG. 2F) and activation measured by expression of activation marker CD27 (FIG. 2G), and it also restored B cell proliferation and CD27 expression upon SSI-4 treatment (FIGS. 2F and 2G). Thus, MUFAs, particularly OA, promote B cell proliferation and class switch in vitro.

TABLE 1

The concentrations of non-esterified free fatty acids (NEFA) were measured in female mice serum (8 weeks old, n = 8), including EPA, linolenic, DHA, myristic, palmitoleic, arachidonic, linoleic, palmitic, oleic, and stearic acids.

| Non-esterified free fatty acid (NEFA) | Concentration (μM, Mean ± SD) |
| --- | --- |
| EPA | 4.44 ± 0.56 |
| Linolenic acid | 44.6 ± 12.7 |
| DHA | 23 ± 3.5 |
| Myristic acid | 7.55 ± 2.17 |
| Palmitoleic acid | 31.7 ± 5.53 |
| Arachidonic acid | 14.8 ± 1.24 |
| Linoleic acid | 304 ± 74 |
| Palmitic acid | 239 ± 26.1 |
| Oleic acid | 184 ± 37.9 |
| Stearic acid | 53.8 ± 8.39 |

MUFA Maintains B Cell Metabolic Fitness

Figure 3A:
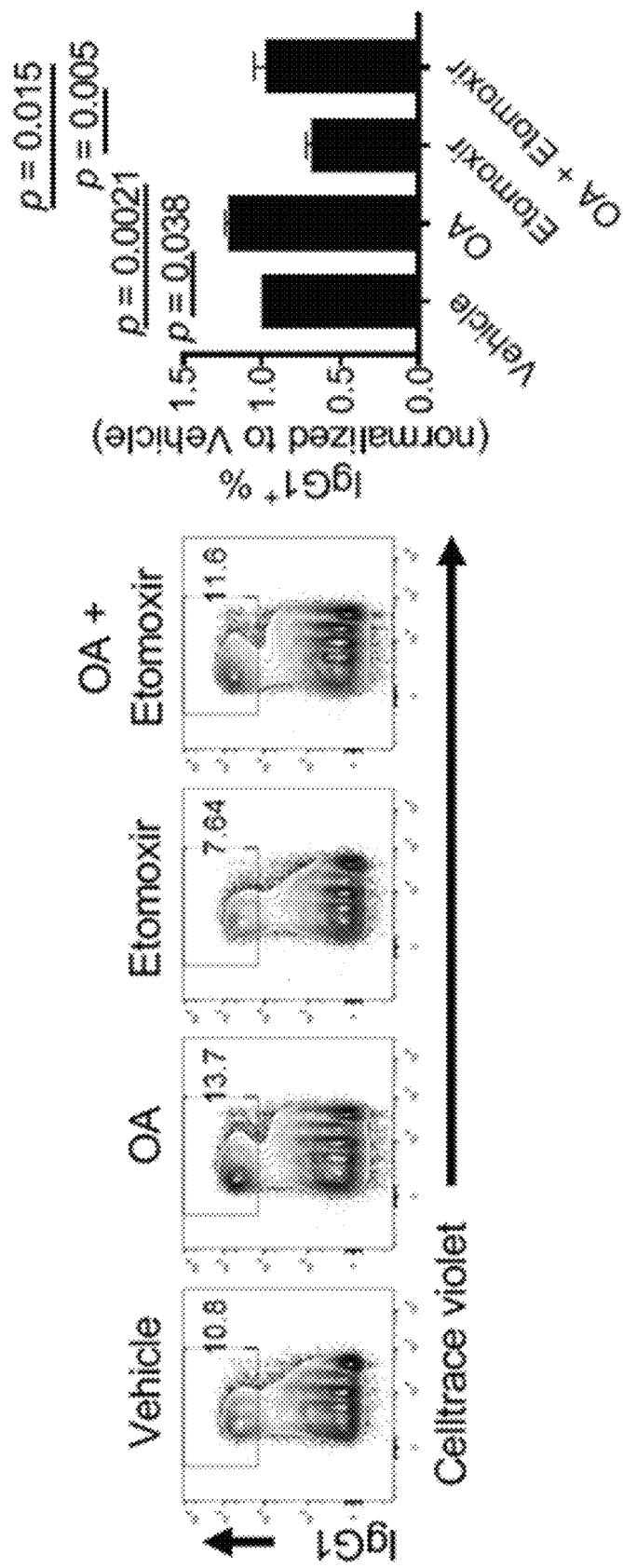
Figure 3B:
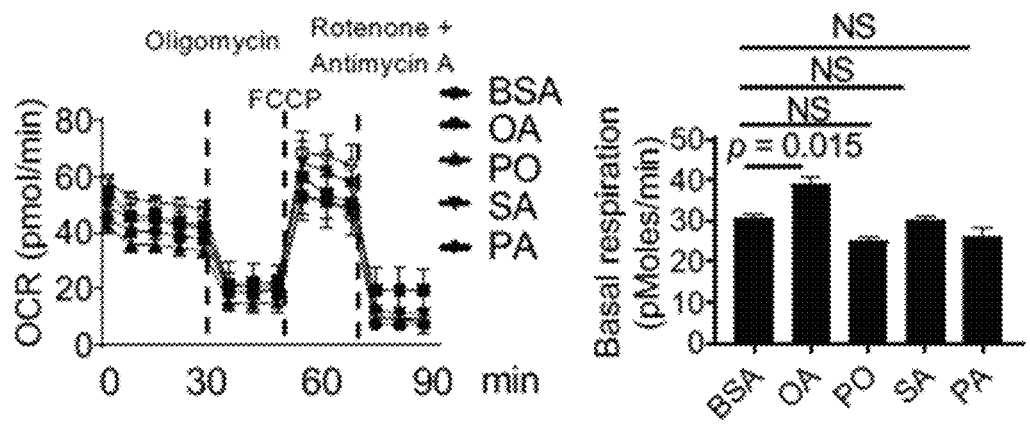
Figure 3C:
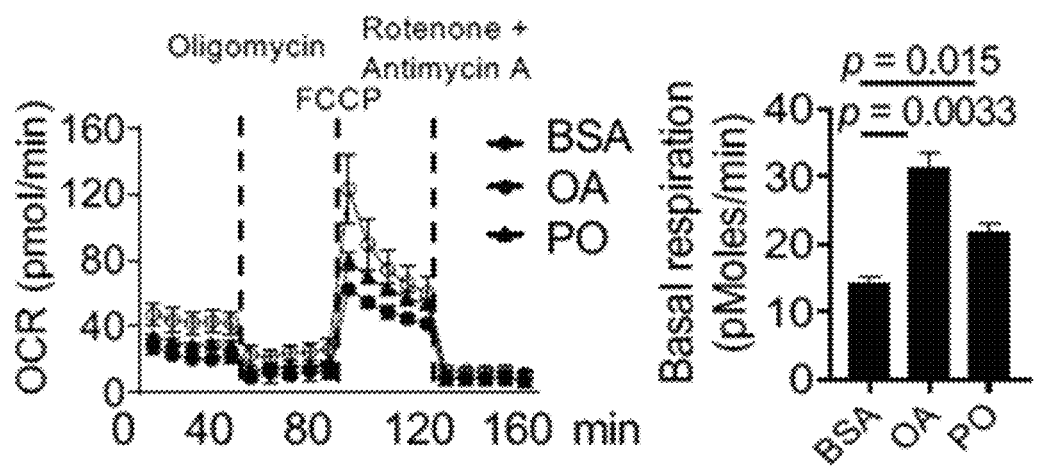
Figure 3G:
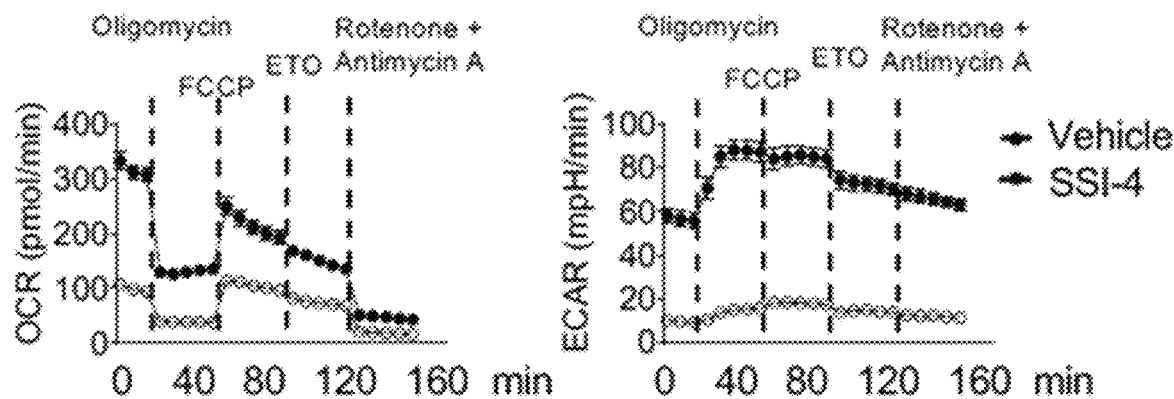
Figure 3H:
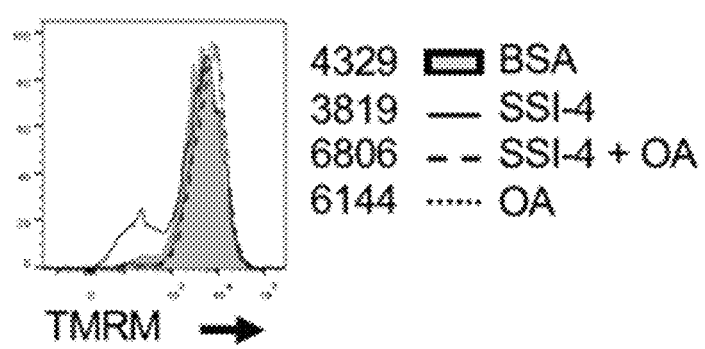

B cell activation is accompanied by increased oxygen consumption, which are important to support humoral immunity. FAs can be utilized to fuel mitochondrial oxidative phosphorylation (OXPHOS) and to provide energy, but it is unclear how different FAs contribute to B cell metabolism. Indeed, the inhibitor etomoxir, which blocks carnitine palmitoyltransferase I (CPT1)-mediated FA import to mitochondrial, reduced B cell class switch, and negated the effects of OA treatment at 40 μM, a dose selective to CPT1 inhibition (FIG. 3A). This data indicated that fatty acid oxidation (FAO) of OA supports B cell function. To analyze the metabolic function of SFAs and MUFAs on B cell OXPHOS, the oxygen consumption rate (OCR) was measured for B cells stimulated by CpG/IL-4/IL-5 in the presence of different exogenous FAs. Addition of OA, but not SFA, enhanced B cell respiration (FIG. 3B). Similar findings were observed using LPS/IL-4 and anti-IgM/IL-4 stimulation (FIG. 10A, 10B). The augmented respiration was also observed in activated human B cells supplied with OA (FIG. 3C). OA mediated increase of respiration was dose dependent (FIG. 3D). The effect of PO on B cell metabolism appeared to be highly variable. While it did not promote respiration upon CpG and anti-IgM/anti-CD40 stimulation (FIG. 3B, FIG. 10B), it did enhance OCR upon LPS/IL-4 stimulation in mouse B cells (FIG. 10A) and in human B cells (FIG. 3C). Moreover, OA and, to a less degree, PO, increased the glycolytic capacity of activated murine B cells while SFA had either negative or no effects on glycolysis (FIG. 3E). Consistent with murine data, OA improved human B cell glycolysis (FIG. 3F). Thus, the data indicate that OA promotes both mouse and human B cell OXPHOS and glucose metabolism. Conversely, inhibition of SCD activity via SSI-4 strongly suppressed B cell respiration and glycolysis (FIG. 3G). Consistent with defective energetic and anabolic metabolism, reduced mitochondrial membrane potential was observed as measured by staining of tetramethylrhodamine (TMRM) when SCD activity was inhibited, which was corrected with exogenous OA (FIG. 3H). OA alone was also able to increase mitochondrial membrane potential (FIG. 3H). These data suggest that provision of OA through SCD activity is critical for B cell metabolic fitness.

SCD-Mediated MUFA Supports mTORC1 Activity and Prevent Excessive Autophagy

Figure 4A:
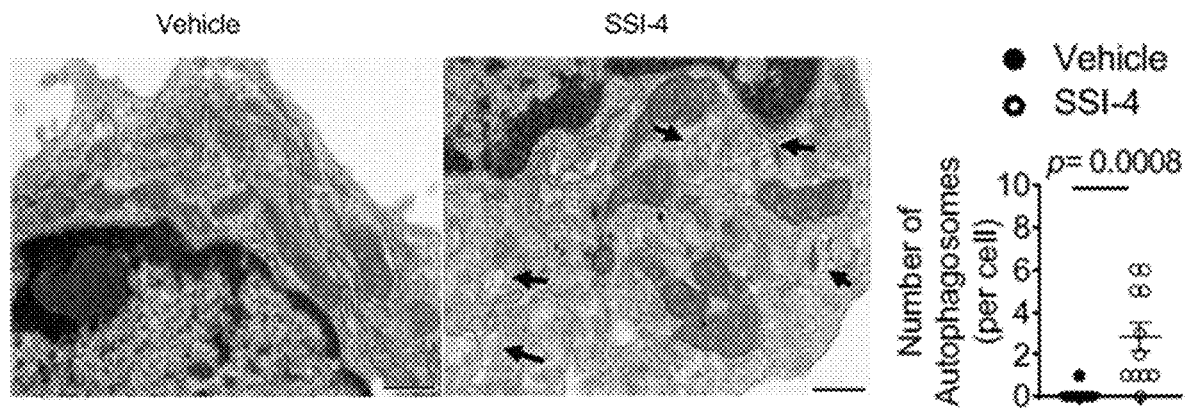
FIGS. 4A-4F. Inhibition of SCD activity induces the formation of autophagosomes and suppresses mTORC1 activity.
Figure 4B:
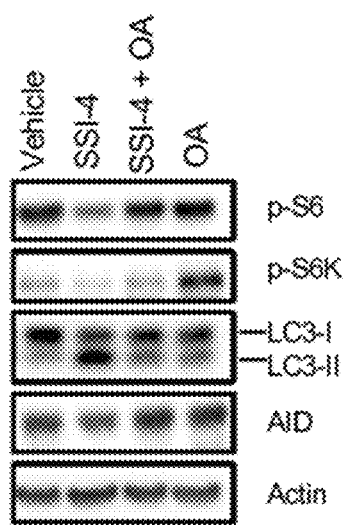
Figure 4C:
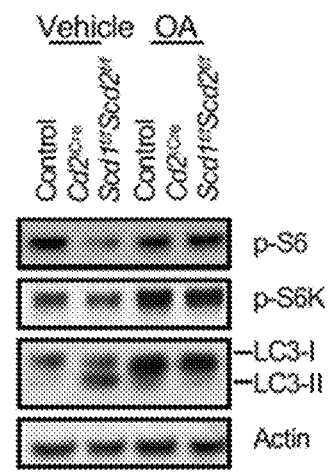
Figures 4D, 4E:
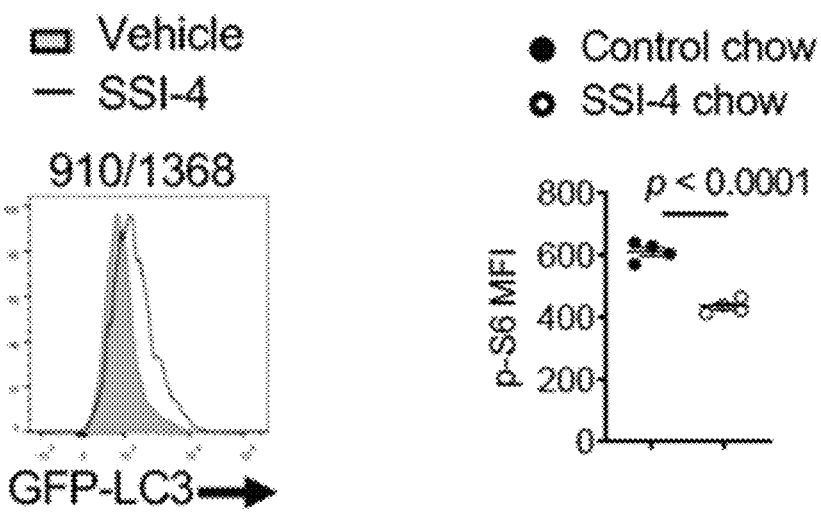
Figure 4F:
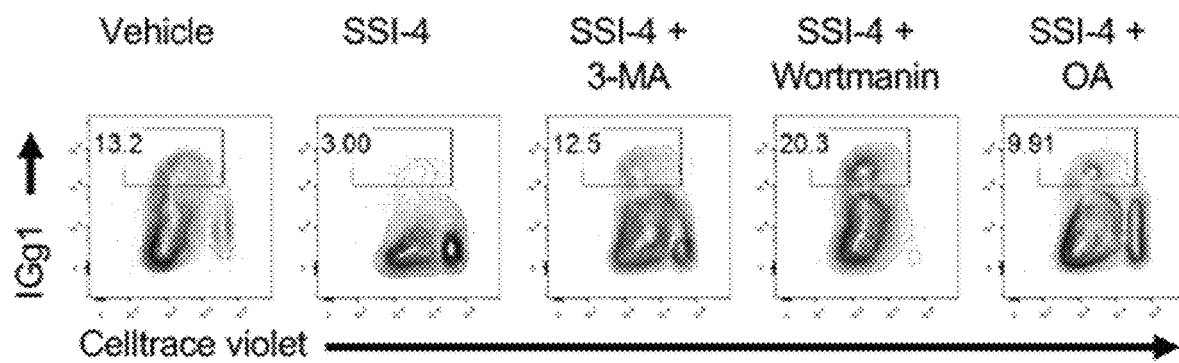

SCD mediated FA metabolism has been linked to autophagy induction in fibroblasts and cancer cells, but there are contradictory findings (Tan et al., *Autophagy* 10:226-242 (2014); Ogasawara et al., *The Journal of biological chemistry* 289:23938-23950 (2014); and Huang et al., *Cancer letters* 358:180-190 (2015)). It is unclear how FA metabolism may link to autophagy in lymphocytes. To examine how SCD inhibition affects subcellular organelles, transmission electron microscopy was performed on SSI-4 treated B cells, as well as SCD deficient B cells. increased structures with double layer membrane encompassing various organelles or multi-lamellar membrane structures, which are signatures of autophagosomes, were observed (FIG. 4A and FIG. 11A). The conversion of the soluble form of LC3 (LC3-I) to the autophagic vesicle-associated form (LC3-II) is a hallmark of autophagy. Immunoblot analysis showed that SSI-4 treated B cells (FIG. 4B) and SCD deficient B cells (FIG. 4C) had substantial increase of LC3-II/LC3-I ratio compared to control cells. Treatment with exogenous OA completely rescued the increased LC3-II/LC3-I ratio (FIG. 4B, 4C). Consistent with the immunoblot data, B cells isolated from GFP-LC3 reporter mouse had higher LC3 expression after inhibition of SCD activity by SSI-4 ex vivo (FIG. 4D). It is well established that mTORC1 controls autophagy and cell metabolism. To examine whether the inhibition of SCD activity induced autophagy, the phosphorylation levels of S6K, and S6, which are the direct downstream substrates of mTORC1 pathway, were analyzed. The results showed that the levels of p-S6K and p-S6 were decreased in SSI-4 treated B cells (FIG. 4B) or SCD1/2 deficient B cells (FIG. 4C), which were restored by exogenous OA (FIG. 4B, 4C). Reduced expression of activation-induced cytidine deaminase (AID) was also observed upon SSI-4 treatment, consistent with the positive effect of mTORC1 on AID induction (FIG. 4B). Furthermore, SCD inhibition also suppressed mTORC1 activity in B cells in vivo, when mice were fed with SSI-4 chow or control chow followed by immunization with hapten 4-hydroxy-3-nitrophenylacetyl conjugated with ovalbumin (NP-OVA) (FIG. 4E). Furthermore, it was tested whether suppression of autophagy can rectify the B cell defects in vitro. Treatment with classic autophagy inhibitors, 3-methyladenine (3-MA) and wortmannin, both targeting class III PI3K, successfully rescued the B cell proliferation and class switch to IgG1 in the presence of SSI-4 (FIG. 4F). Lastly, increased SFA content is associated with increased endoplasmic reticulum (ER) stress. Because SCD inhibition increases the SFA/MUFA ratio (FIG. 1F), it could also induce ER stress. Indeed, it was found that the ER stress-related genes, including Chop, Atf4, and Sqstm1, were increased after SSI-4 treatment, while exogenous OA reduced these genes upregulation (FIG. 11B). Taken together, these data showed that SCD-mediated MUFA availability is required for suppressing ER stress and maintenance of mTORC1 activity, which prevents overactivation of autophagy.

Figure 5A:
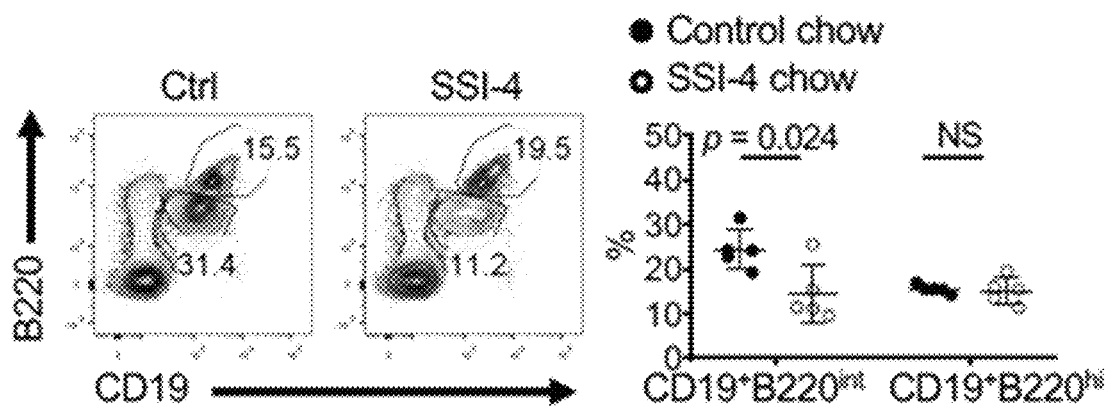
FIGS. 5A-5L. Systemic SCD activity is essential for humoral immune response in vivo.
Figure 5B:
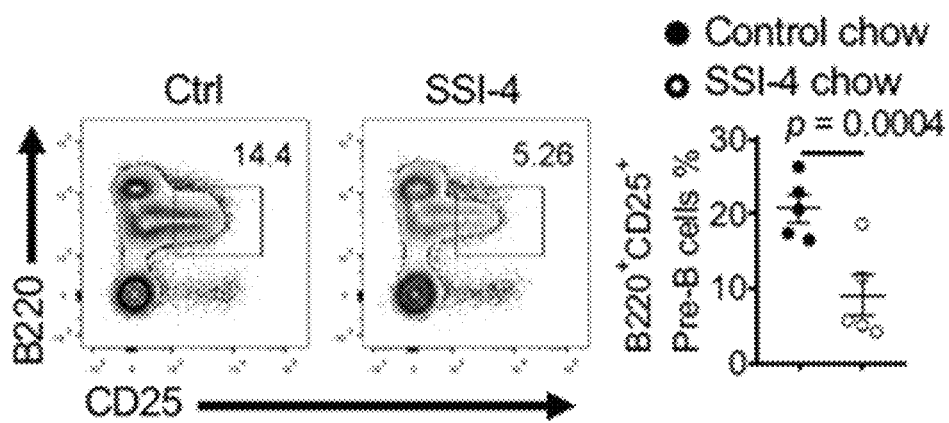
Figure 5C:
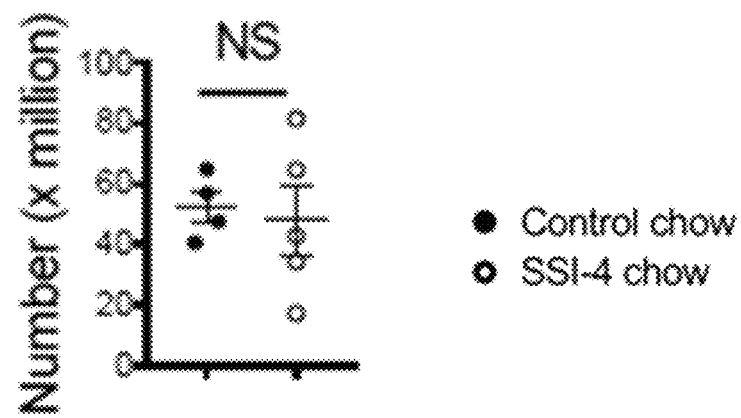
Figure 5D:
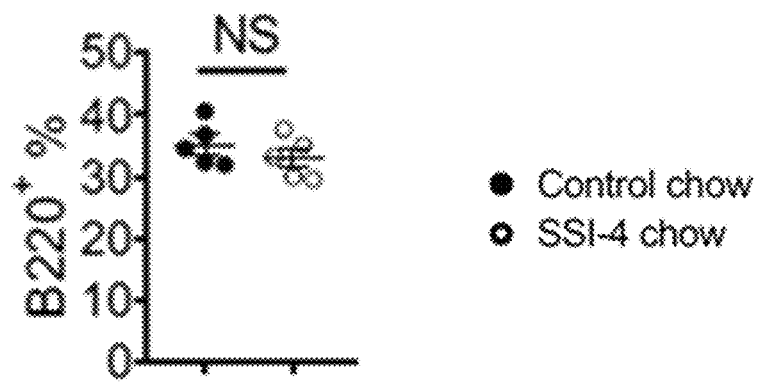
Figure 5E:
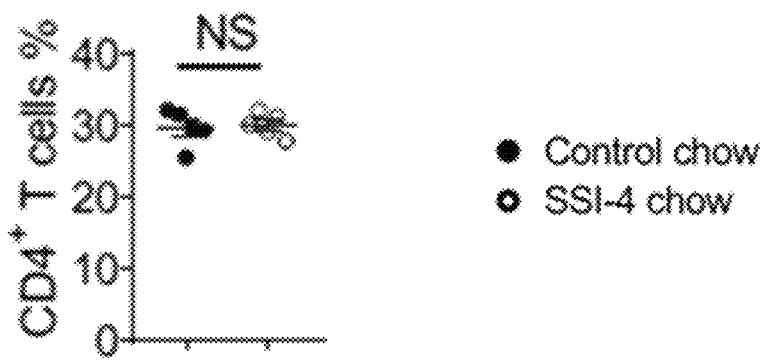
Figure 5F:
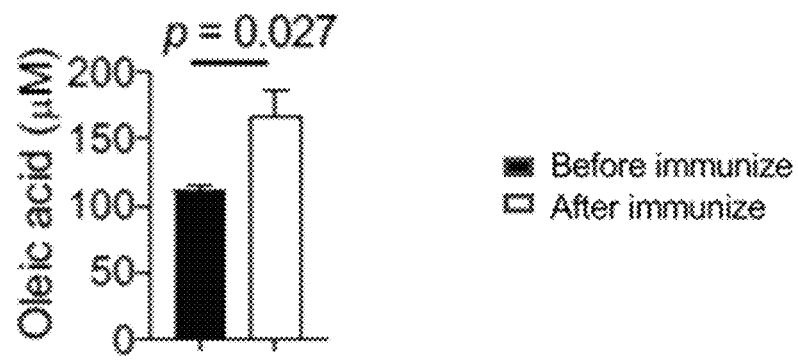
Figure 5G:
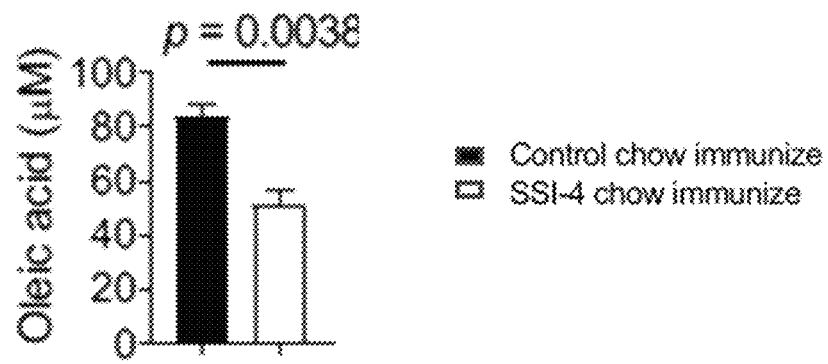
Figure 5H:
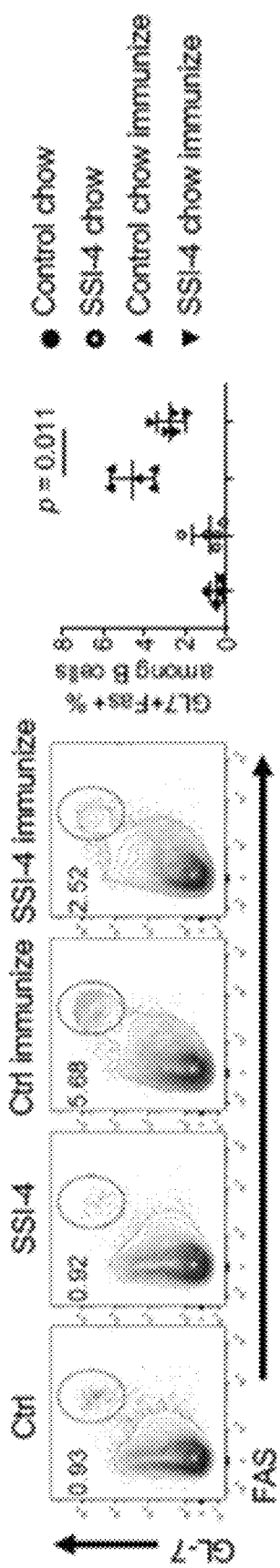
Figure 5I:
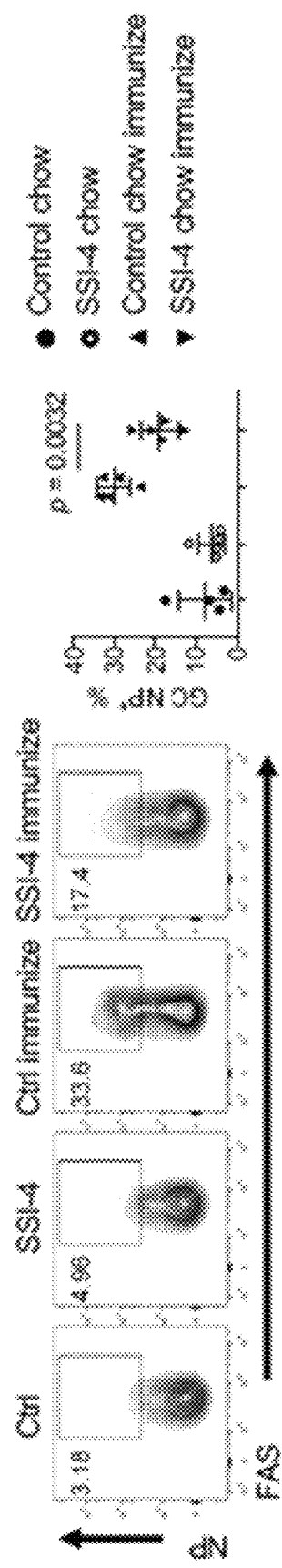
Figure 5J:
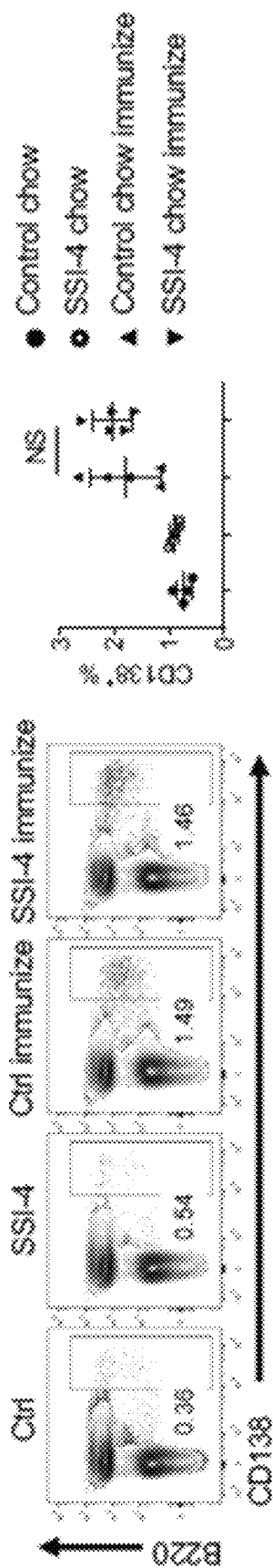
Figure 5K:
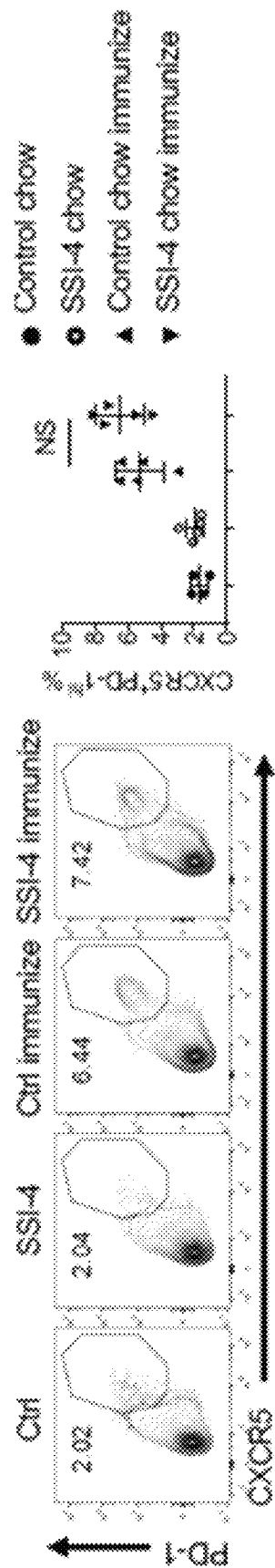
Figure 5L:
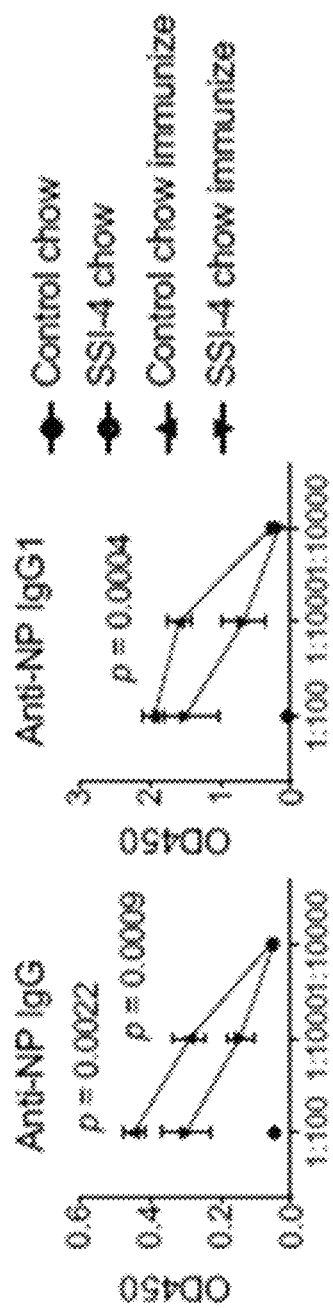
Figure 12A:
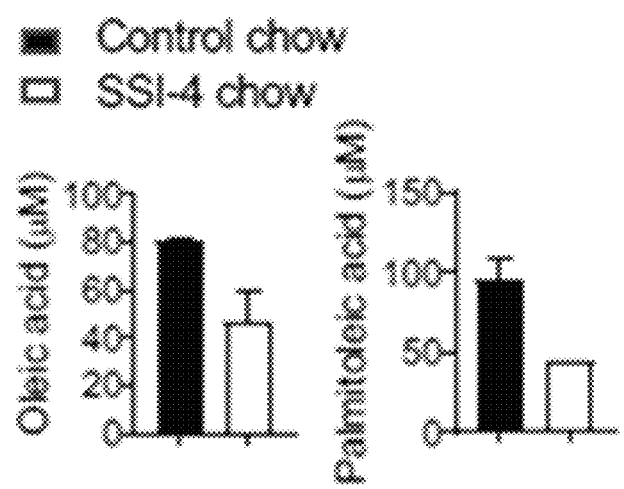
Figure 12B:
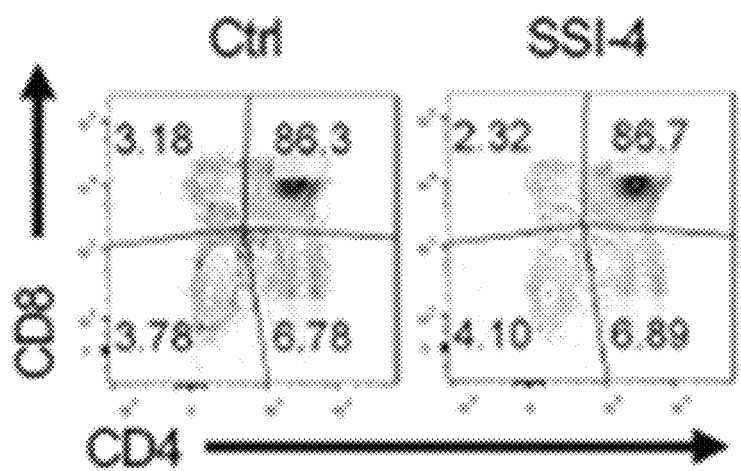

Systemic SCD Activity Supports Early B Cell Development and Humoral Immune Response In Vivo Next, it was investigated how SCD activity contributes to B cell development and function in vivo. Feeding mice with SSI-4 chow for 1 week markedly reduced serum OA and PO concentration, demonstrating the efficacy of SSI-4 in vivo (FIG. 12A). At this time, SSI-4 treatment resulted in significant reduction of the pool of immature B cells and B cell precursors (CD19$^+$ B220$^{int}$) in bone marrow (BM) (FIG. 5A) and CD25$^+$ pre-B cells (FIG. 5B). The composition of thymocytes were unaffected after SSI-4 treatment (FIG. 12B). In addition, the number of peripheral B cells and CD4$^+$ T cells were not affected by the reduced OA content (FIG. 5C-5E), although the frequency of mature B cells (CD19$^+$IGM$^{lo}$IgD$^+$) was slightly increased with SSI-4 chow treatment (FIG. 12C). Moreover, a modest reduction of GC percentage and IgA expression in Peyer's patches, where gut microbiota drives constitutive generation of GC and class switch to IgA, were observed (FIG. 12D, 12E), suggesting that SCD activity may be required for these processes. The impact of SCD inhibition on humoral immune response upon stimulation with foreign antigen, NP-OVA was next evaluated in vivo. Notably, it was observed that immunization increased OA concentration in sera (FIG. 5F), indicating that immune challenge is associated with increase of systemic MUFA content in vivo. SSI-4 treatment substantially reduced the OA level in immunized mice as expected (FIG. 5G). Importantly, SCD inhibition significantly suppressed splenic GC formation (FIG. 5H) and reduced antigen specific NP$^+$ GC B cells (FIG. 5I). However, B220$^{int}$CD138$^+$ plasmablast generation was not affected by inhibition of SCD activity, suggesting that GC formation, but not plasmablast differentiation, is particularly sensitive to MUFA availability (FIG. 5J). Furthermore, the percentage of Tfh cells after immunization was comparable between these two groups, suggesting that SCD activity preferentially supported B cell activation (FIG. 5K). Consequently, the production of anti-NP specific total IgG and IgG1, but not IgM, antibodies were significantly reduced in response to systemic inhibition of SCD activity (FIG. 5L). Therefore, SCD activity supports early B cell development in the BM, and promotes GC formation and antibody production upon immunization.

SCD Activity is Required for Humoral Immunity Against Influenza Infection

Figure 6A:
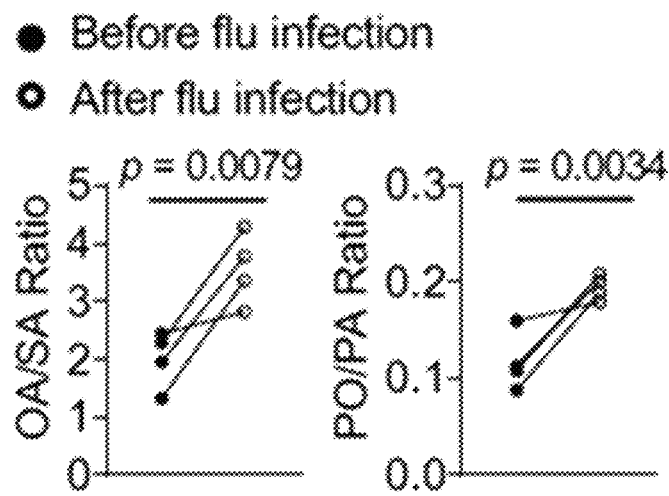
FIGS. 6A-6G. SCD activity is required for humoral immunity against influenza infection.
Figure 6B:
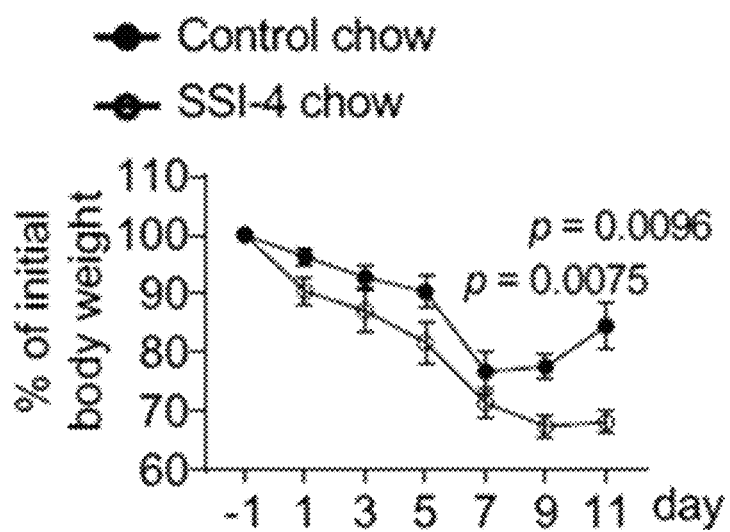
Figure 6C:
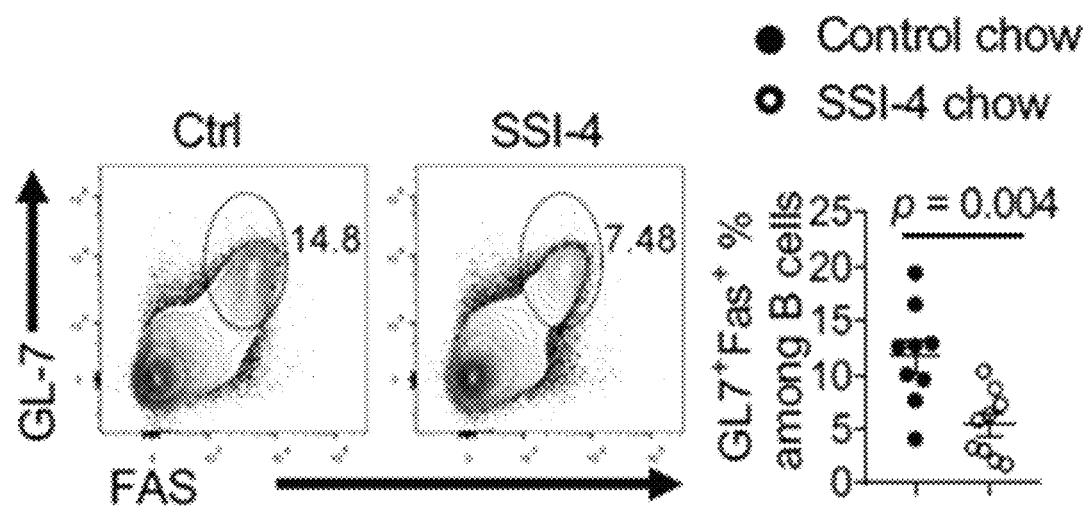
Figure 6D:
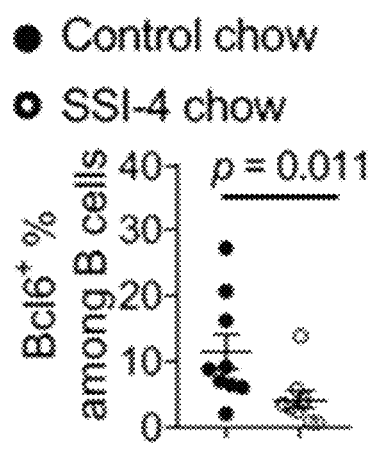
Figure 6E:
Figure 6F:
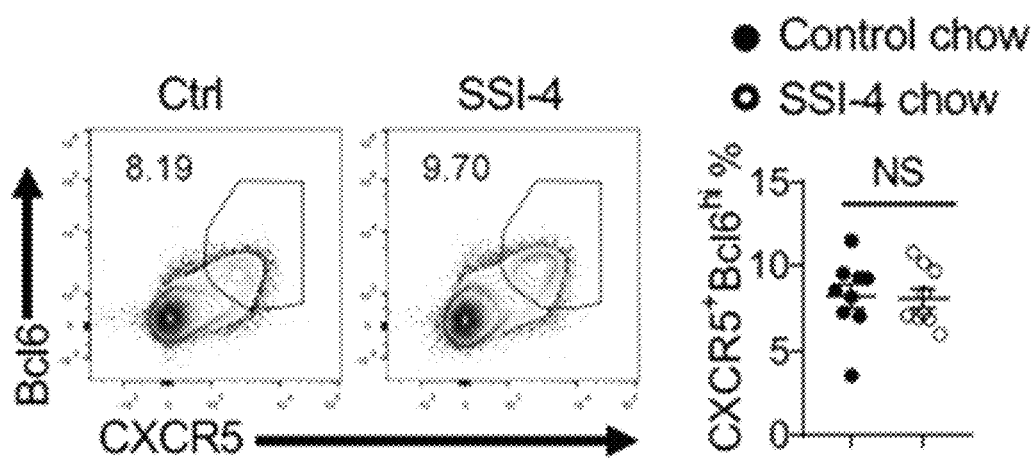
Figure 6G:
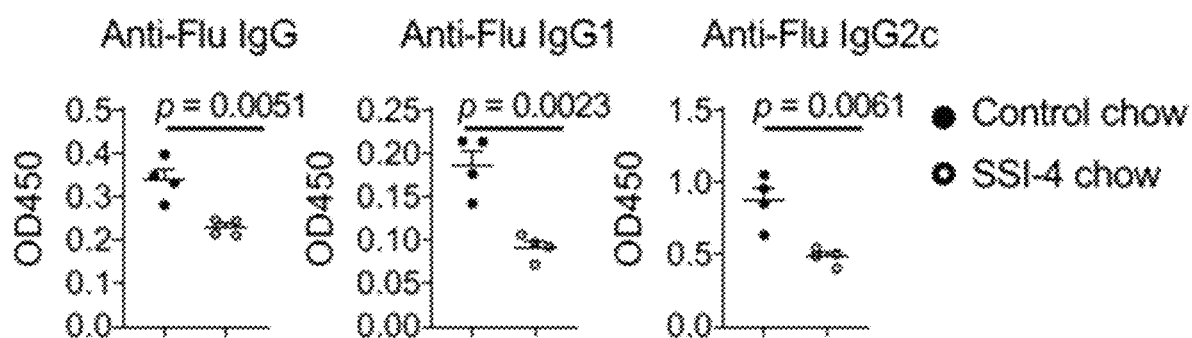

Increased serum OA and PO concentration, and OA/SA and PO/PA ratio after H1N1 influenza A infection were observed, suggesting that influenza infection might trigger SCD activity (FIG. 6A). Feeding with SSI-4 chow led to substantially more severe weight loss in influenza A infected mice compared to control chow (FIG. 6B). The systemic inhibition of SCD activity by feeding with SSI-4 chow significantly reduced the frequency of GC B cells (FIG. 6C), and the expression of Bcl6, key transcription factor for GC B cell differentiation, in B cells (FIG. 6D). However, it did not affect CD138$^+$ plasmablast formation (FIG. 6E), nor did it affect CXCR5$^+$ Bcl6$^{hi}$ Tfh cell differentiation (FIG. 6F). Consequently, SCD inhibition significantly dampened the production of anti-influenza total IgG, IgG1 and IgG2c, but not IgM, in sera (FIG. 6G). Altogether, these data suggested that SCD activity is essential for antigen specific GC B cell formation and antibody production upon immunization and respiratory viral infection in vivo.

Figure 7A:
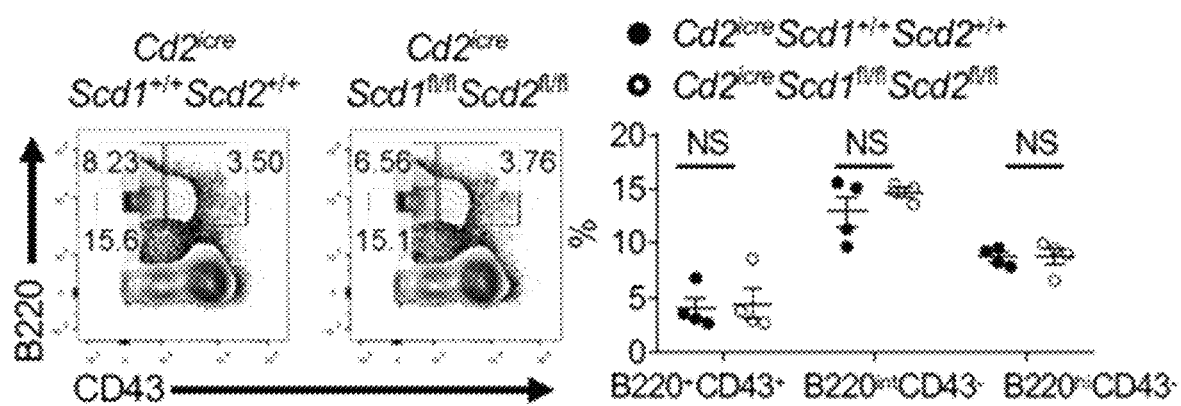
FIGS. 7A-7D. B cell intrinsic SCD activity is not required for B cell development and humoral response in vivo.
Figure 7B:
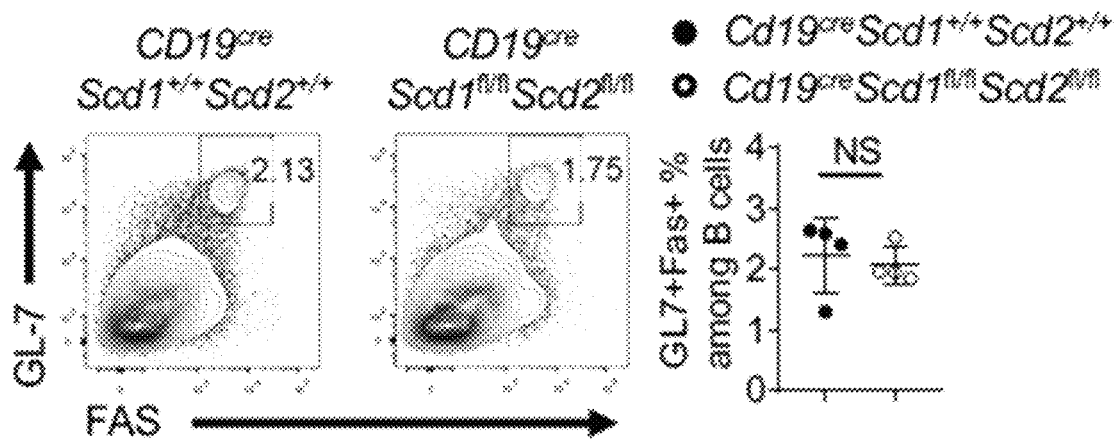
Figure 7C:
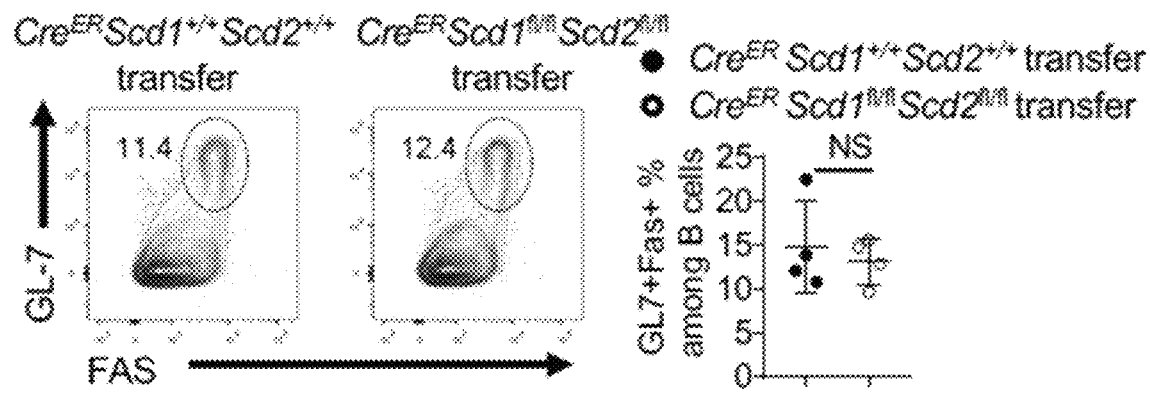
Figure 7D:
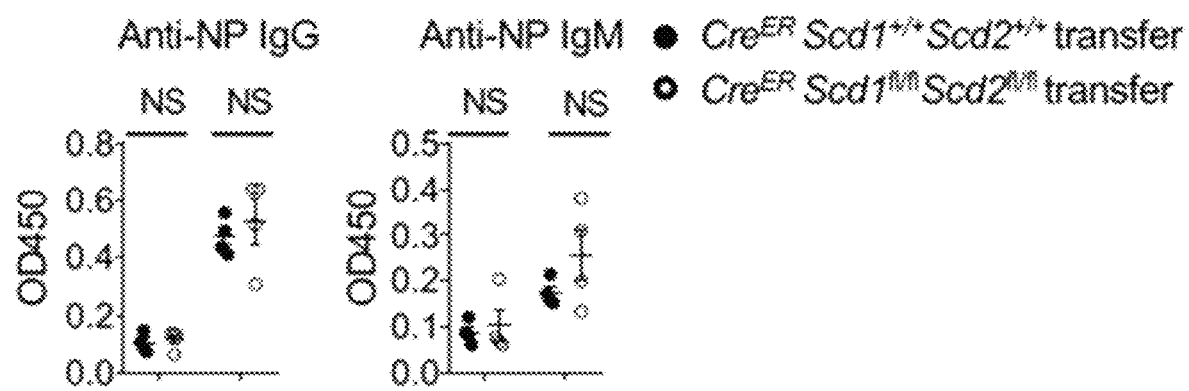

Intrinsic SCD Activity is not Required for B Cell Development and B Cell Response In Vivo Although the above data clearly demonstrated that SCD activity was critically required for B cell development and function, it was unclear whether B cell intrinsic or extrinsic SCD activity was responsible in vivo. Because the in vitro experiments demonstrated that exogenously supplemented OA was able to rescue the SCD deficient B cells, it is possible that B cell-extrinsic SCD activity could compensate the loss of SCD in B cells. To examine whether SCD activity in lymphocytes is required for humoral immunity, B cell development was examined in Cd2$^{iCre}$Scd1$^{fl/fl}$Scd2$^{fl/fl}$ mice, in which Scd1 and Scd2 were deleted in all lymphocytes from common lymphocyte precursors. Significant alteration in early B cell development was not observed, suggesting that B cell intrinsic SCD activity was dispensable for early B cell development (FIG. 7A). Moreover, Cd19$^{cre}$Scd1$^{fl/fl}$Scd2$^{fl/fl}$ mice were examined, in which Scd1 and Scd2 were deleted specifically and efficiently in B cells at a later stage (FIG. 13A). To examine whether B cell intrinsic SCD activity contributed to B cell activation in vivo, Cd19$^{cre}$Scd1$^{fl/fl}$Scd2$^{fl/fl}$ mice were immunized with NP-OVA. Significant defect in GC formation was not observed (FIG. 7B). To eliminate any possible secondary effects elicited by chronic SCD deficiency during B cell development, chimera mice were constructed by transferring purified SCD deficient B cells from tamoxifen treated Cre$^{ER}$Scd1$^{fl/fl}$Scd2$^{fl/fl}$ mice, together with CD4 T cells from OT-II transgenic mice and WT mice, into Rag1$^{-/-}$ mice, followed by immunization with NP-OVA. Again, differences were not observed in terms of GC formation (FIG. 7C) and antibody production (FIG. 7D). Altogether, these data indicate that B cell intrinsic SCD activity is not essential for B cell development and function, or alternatively, B cell extrinsic SCD activity can compensate for the loss of SCD activity in B cells to support humoral immunity.

Materials and Methods
Isolation of Human B Cells

PBMCs were isolated from the medical waste following apheresis collection of platelets. Briefly, blood was diluted 1:3 using PBS. The diluted blood was then overlaid with Ficoll-Paque PLUS density gradient medium (GE Healthcare). The gradient was centrifuged at 400 g with no brake for 25 minutes at room temperature. The PBMC interphase layer was collected, washed with PBS with 0.1% BSA/2 mM of EDTA. Naive B cells (CD19$^+$CD27$^-$IgD$^+$) were enriched using Human naive B cell negative selection kit (Stemcell Technologies).

Mice

Scd foxed mice were crossed with Cre-ERT2, Cd2-iCre or Cd19-Cre transgenic mice (Jackson Laboratory). C57BL/6 and Rag1$^{-/-}$ mice were purchased from the Jackson Laboratory. For SCD activity in vivo inhibition experiment, animals were maintained on chow containing SCD inhibitor SSI-4 (30 mg/kg) or control chow. The composition of other nutrients, vitamins, and minerals were equivalent between theses diets. After SSI-4 or control chow treatment for two weeks, mouse sera were collected, and the mice were sacrificed and the bone marrow, thymus, spleen and mesenteric lymph nodes were examined. One day prior to immunization, mice were fed with SSI-4 and control chow. Antigen for immunization was prepared by mixing NP-OVA (Biosearch Technologies), 10% KAL(SO$_4$)$_2$ dissolved in PBS at a ratio of 1:1, in the presence of LPS (*Escherichia coli* strain 055: B5; Sigma) at pH 7. Mice were immunized intraperitoneally (100 µg NP-OVA and 10 µg LPS precipitated in alum) for analysis of GC B cell generation in spleen and NP-specific antibody response in serum. Transfer model were generated by transferring 5×10$^6$ B cells isolated from Cre$^{ER}$Scd1$^{fl/fl}$Scd2$^{fl/fl}$ or Cre$^{ER}$Scd1$^{+/+}$Scd2$^{+/+}$ treated with tamoxifen for 4 consecutive days, mixing with 4×10$^6$ CD4 T and 1×10$^6$ OT-II transgenic T cells, into Rag1$^{-/-}$ mice. Three weeks after first immunization, mice were boosted with NP-OVA. One week after second immunization, the mice were sacrificed, and the spleens were examined.

For influenza virus infection, influenza A/PR8 strain (200 pfu/mouse) were diluted in FBS-free DMEM media on ice and inoculated in anesthetized mice through intranasal route. Sera were collected before and two weeks after infection for fatty acid component measurement. The mice were fed with control chow or SSI-4 chow for 1 week following influenza infection before switching to regular diet. The mediastinal lymph nodes were analyzed for GC B cell formation and Tfh differentiation. Mice were bred and maintained under specific pathogen-free conditions in Department of Comparative Medicine of Mayo Clinic with IACUC approval.

RNA-Seq

RNA from isolated fresh B cells and B cells activated with LPS/IL-4 was extracted using a RNeasy kit (Qiagen) following the manufacturer's instructions. After quality control, high quality total RNA was used to generate the RNA sequencing library. Paired-end RNA-seq reads were aligned to the mouse reference genome (mm10) using a spliced-aware reads mapper Tophat2 (v2.0.6). Pre- and post-alignment quality controls, gene level raw read count and normalized read count (i.e. FPKM) were performed using RSeQC package (v2.3.6) with NCBI mouse RefSeq gene model. Differential gene expression analyses were conducted using edgeR (version 3.6.8) and the built-in "TMM" (trimmed mean of M-values) normalization method were used. The criteria for selection of significant differentially expressed genes were: |log 2 fold change|>=1.0 and p value <=0.001.

Immune Cell Purification and Culture

Mouse B cells were isolated from pooled single cell suspensions of spleen and peripheral lymph nodes using CD19 Microbeads (Miltenyi) or Mouse B cell Isolation Kit (Stemcell Technologies). B cells were stimulated with LPS (10 µg/mL; Sigma-Aldrich) and recombinant IL-4 cytokine (10 ng/mL; Tonbo Bioscience) with or without SCD inhibitor SSI-4, and proliferation was measured by dilution of CellTrace Violet proliferation dye (Thermo Fisher Scientific). B cells were also stimulated with anti-IgM (10 µg/mL; Jackson ImmunoResearch), anti-CD40 (10 µg/mL; BioXcell) and IL-4 (10 ng/mL; Tonbo Bioscience), or TLR ligand CpG (2.5 µM; IDT), recombinant IL-4 and IL-5 (10 ng/mL; Tonbo Bioscience) cytokines. To test the function of monounsaturated and saturated fatty acids, B cells were activated in presence of exogenous fatty acid-BSA conjugate. Palmitoleic acid (NU-CHEK PREP, INC), palmitic acid (NU-CHEK PREP, INC), stearic acid (NU-CHEK PREP, INC) were conjugated with fatty acid free BSA (Sigma-Aldrich) as described elsewhere (Wang et al., *Immunity* 35:871-882 (2011)). Human B cells were activated with CpG OND2006 (2.5 µM; IDT), recombinant human cytokine IL-10 (50 µg/mL; Peprotech), IL-15 (10 ng/mL; Peprotech), IL-4 (10 ng/mL; Biolegend), IL-2 (10 unit/mL) and anti-human CD40 (1 µg/mL; BioXcell). Human B cell proliferation was measured by $^3$[H]-thymidine incorporation (1 µCi/mL) (American Radiolabeled Chemicals).

Non-Esterified Free Fatty Acids (NEFAs) and Total Fatty Acid Composition

Fatty acids and total fatty acid composition were measured against a standard curve on a triple quadrupole mass spectrometer coupled with an Ultra Pressure Liquid Chromatography system (LC/MS) as previously described. Briefly, the cell pellets were spiked with internal standard prior to extraction with tert-Butyl Methyl Ether (MTBE). Roughly 25% of the sample was dried down, hydrolyzed, re-extracted and brought up in running buffer for the analysis of total fatty acid composition. The remaining portion of the extract was dried down and brought up in running buffer prior to injecting on the LC/MS for the NEFA measurement. Data acquisition was performed under negative electrospray ionization condition.

Mass Spectrometer Measurement of Serum NEFA Using Liquid Chromatography System

Fatty acids were measured against a standard curve on a Thermo Quantum Ultra triple quadrupole connected to a Waters Acquity Ultra high-pressure liquid chromatography system (LC/MS) as previously described. Briefly, 50 µl of serum was spiked with internal standard prior to extraction. The extracts were dried down and brought up in running buffer prior to injecting on the LC/MS. Data acquisition was performed under negative electrospray ionization condition.

NEFA Isotopomer Analysis

Briefly, $5 \times 10^6$ activated B cells were washed with PBS and re-cultured in glucose-free medium RPMI medium containing 10% dialyzed FBS and uniformly labeled [$^{13}$C]-glucose (2 g/L; Sigma-Aldrich) for 24 and 48 hours. Cell pellets were lysed in 1×PBS prior to lipid extraction. The extract was dried down and brought up in running buffer before underwent analysis on an Agilent 6550 iFunnel Q-TOF mass spectrometer/1290 Infinity liquid chromatographic system. A mixed standard containing 14 fatty acids was also run at the beginning and at the end of the sequence to generate retention time lock as well as unlabeled mass spectrum for each fatty acid. The mass spec was operating in negative electrospray ionization. Data was acquired in scan mode from 50-1700 m/z range. Data analysis was performed on Agilent Technologies software including Profinder, Mass Profiler Professional (MPP) and Vista Flux. Briefly, the features extracted from the data files were aligned using Profinder and converted to a compound exchange file (CEF) format to import in the MPP. The list was filtered for frequency and abundance to identify features that are present in all samples and with high abundance. A library was created using mass, molecular formula, and retention time of these features and used in conjunction with the Vista Flux software to determine the presence of isotopologue in individual feature. Fatty acids displaying a presence of isotopic pattern were annotated using retention time lock, accurate mass, and the METLIN database with an error of 5 ppm.

GC-MS Analysis of Oleic Acid and Palmitoleic Acid

Fatty acids were extracted from mouse serum samples using Lipid Extraction Kit (Biovison: K216). In brief, 25 µl of serum and 0.5 ml of Lipid Extraction Buffer containing 1 µg of D2-oleic acid (Cambridge isotope: DLM-689-0.1) and 1 µg of D14-palmitoleic acid (Cayman: 9000431) were mixed, vortexed for 1 minute, and agitated for 15-20 minutes on an orbital shaker at room temperature. The samples were then centrifuged at 10,000×g for 5 minute and the supernatants containing lipids were dried under $N_2$ gas. Dried metabolite samples were dissolved in 75 µL methoxyamine (20 mg/mL in pyridine) and incubated at 70° C. for 30 minutes. Samples were then further derivatized with 75 µL N-Methyl-N-(tert-butyldimethylsilyl) trifluoroacetamide (MTBSTFA)+1% tertbutyldimetheylchlorosilane (TBDMCS) and incubated again at 70° C. for 30 minutes. Samples were analyzed using an Agilent 7890B GC coupled to a 5977A mass detector. 3 µL of derivatized sample were injected into an Agilent HP-5 ms Ultra Inert column, and the GC oven temperature increased at 15° C./minute up to 215° C., followed by 5° C./minute up to 260° C., and finally at 25° C./minute up to 325° C. The MS was operated in split-less mode with electron impact mode at 70 eV. Mass range of 50-700 was analyzed, recorded at 1,562 mass units/second. The following fatty acids were detected as TBDMS derivatives: oleic acid (m/z 339), D2-oleic acid (m/z 341), palmitoleic acid (m/z 311), and D14-palmitoleic acid (m/z 325). Data was analyzed using Agilent MassHunter Workstation Analysis and Agilent MSD ChemStation Data Analysis softwares. IsoPat$^2$ software was used to adjust for natural abundance as described elsewhere (Kurmi et al., *Cell Rep* 22:1365-1373 (2018)).

Electron Microscopy

Cells were fixed in Trumps fixative (pH 7.2) at 4° C. overnight, spun down and the supernatant removed. They were re-suspended in 2% agarose which was allowed to cool and solidify. The cells in agarose were then post-fixed in 1% $OsO_4$, dehydrated through a graded series of ethanols and embedded in Spurr resin. One hundred nm (or 0.1 mm) ultra-thin sections were mounted on 200-mesh copper grids, post-stained with lead citrate, and observed under a JEOL JEM-1400 transmission electron microscope at 80 kV.

Metabolic Assays

The bioenergetic activities of the OCR and ECAR were measured using a Seahorse XFe96 Extracellular Flux Analyzed following established protocols (Agilent). Briefly, B cells were seeded at 200,000 cells/well on Cell-Tak (Corning) coated XFe96 plate with fresh XF media (Seahorse XF RPMI medium containing 10 mM glucose, 2 mM L-glutamine, and 1 mM sodium pyruvate, PH 7.4; all reagents from Agilent). OCR was measured in the presence of Oligomycin (1.5 µM; Sigma-Aldrich), FCCP (1.5 µM; Sigma-Aldrich), and Rotenone (1 µM; Sigma-Aldrich)/Antimycin A (1 µM;

Sigma-Aldrich) in Mito Stress assay. For ECAR measurement, B cells were seeded in XFe96 plate with fresh Seahorse XF RPMI medium with 2 mM L-glutamine (PH 7.4), and treated with glucose (10 mM; Agilent), Oligomycin (1.5 and 2-DG (50 mM; Sigma-Aldrich) orderly in Glycolysis Stress assay.

Immunoblotting

For immunoblotting, cells were lysed in lysis buffer with protease and phosphatase inhibitors (Sigma-Aldrich). Protein concentration in samples were quantified by BCA assay (Thermo Fisher Scientific) before loading the samples for electrophoresis and membrane transfer. The transferred membrane was blocked with TBST (0.1% Tween 20) containing 5% BSA for 1 hour at room temperature. The membrane was incubated with primary antibodies overnight including anti-p-S6 (Ser235/Ser236, D57.2.2E; Cell Signaling), anti-p-p70 S6 kinase (Thr389, 108D2; Cell Signaling), anti-p-4E-BP1 (Thr37/46, 236B4; Cell Signaling), anti-LC3α/β (G-4; Santa Cruz); anti-p-ULK1 (Ser757, D706U; Cell Signaling), anti-AID (EK2 5G9; Cell Signaling), anti-β-actin (13E5; Sigma-Aldrich), and anti-SCD2 (H-12; Santa Cruz). Then, the membrane was washed and incubated with the corresponding secondary antibody for subsequent enhanced chemiluminescence (ECL; Thermo Fisher) exposure. The band intensity of all the immunoblot was analyzed by ImageJ software.

Quantitative Real-Time PCR

For mRNA analysis, total mRNA was isolated from mouse and human B cells by RNeasy Micro kit (Qiagen), reverse transcribed from mRNA to cDNA for subsequent real-time PCR analysis. Scd1, Scd2, Fasn, Acaca, Chop, Atf4, Sqstm1 in mouse B cells and Scd, Fasn, Acaca expression in human B cells were measured by real-time PCR with a Bio-Rad Realtime PCR system. β-actin expression was used as control. The primers information was provided in the following table.

TABLE 2

Real-time PCR primers.

| Primer | Species | Sequence | SEQ ID NO: |
|---|---|---|---|
| Scd1 | Murine | F 5'-TTCTTGCGATACACTCTGGTGC-3' | 1 |
|  |  | R 5'-CGGGATTGAATGTTCTTGTCGT-3' | 2 |
| Scd2 | Murine | F 5'-GCATTTGGGAGCCTTGTACG-3' | 3 |
|  |  | R 5'-AGCCGTGCCTTGTATGTTCTG-3' | 4 |
| Fasn | Murine | F 5'-GGAGGTGGTGATAGCCGGTAT-3' | 5 |
|  |  | R 5'-TGGGTAATCCATAGAGCCCAG-3' | 6 |
| Acaca | Murine | F 5'-GTCCCCAGGGATGAACCAATA-3' | 7 |
|  |  | R 5'-GCCATGCTCAACCAAAGTAGC-3' | 8 |
| Chop | Murine | F 5'-CTGGAAGCCTGGTATGAGGAT-3' | 9 |
|  |  | R 5'-CAGGGTCAAGAGTAGTGAAGGT-3' | 10 |
| Atf4 | Murine | F 5'-GGGTTCTGTCTTCCACTCCA-3' | 11 |
|  |  | R 5'-AAGCAGCAGAGTCAGGCTT-3' | 12 |
| Sqstm1 | Murine | F 5'-AGGATGGGGACTTGGTTGC-3' | 13 |
|  |  | R 5'-TCACAGATCACATTGGGGTGC-3' | 14 |
| SCD | Human | F 5'-AGTTCTACACCTGGCTTTGG-3' | 15 |
|  |  | R 5'-GTTGGCAATGATCAGAAAGAGC-3' | 16 |
| ACACA | Human | F 5'-GATATCCCAGAGATGTTTCGGC-3' | 17 |
|  |  | R 5'-GTCAGCATGTCAGAAGGCAGAG-3' | 18 |
| FASN | Human | F 5'-AGAACTTGCAGGAGTTCTGGGACA-3' | 19 |
|  |  | R 5'-TCCGAAGAAGGAGGCATCAAACCT-3' | 20 |

Flow Cytometry

For analysis of surface markers, cells were stained in PBS containing 1% (w/v) bovine serum albumin on ice for 30 minutes, with anti-IgG1 (RMG1-1, Biolegend), anti-CD19 (ID3, Biolegend) anti-B220 (RA3-6B2, Biolegend), anti-CD4 (GK1.5, Biolegend), anti-CD8 (53-6.7, Biolegend), anti-CD25 (PC16, Biolegend), anti-GL7 (GL-7, Biolegend), anti-CD95 (Jo2, BD Biosciences), anti-CD138 (281-2, Biolegend), anti-IgD (11-26c.2a, Biolegend), anti-PD-1 (J43, ThermoFisher), anti-IgM (II/41, ThermoFisher). Antigen specific GC response was detected with tetramer NP-phycoerythrin conjugated with PE (Biosearch Technologies). CXCR5 was stained with biotinylated anti-CXCR5 (2G8) followed by staining with streptavidin-conjugated PE (both from BD Biosciences). Cell viability was assessed using the Fixable Dye Ghost 510 (Tonbo Bioscience) or Annexin V cell apoptosis kit with 7-AAD (ThermoFisher) following the manufacturer's protocol. Phosflow staining for phospho-S6 (S235/236) was performed using Phosflow Fix/Perm kit (BD Biosciences). Mitochondrial potential was measured by staining with 20 nM TMRM (ThermoFisher) following manufacturer's instructions. Flow cytometry was performed on the LSR II, LSR Fortessa (BD Biosciences) or Attune NxT (ThermoFisher) cytometers, and analysis was performed using FlowJo software (Tree Star).

ELISA

For NP specific antibodies detection in sera, 96-well plates (2596; Costar) were coated with 2 μg/mL $NP_{23}$-BSA in PBS overnight. Plates were washed twice (0.05% Tween 20 in PBS), blocked with 5% blocking protein (Bio-Rad) for 1 hour, and washed twice, and serially diluted serum samples were added for 1.5 hours at 37° C. Plates were washed four times and horseradish peroxidase (HRP)-conjugated detection Abs for IgG (Bethyl Laboratories) and IgG1 (Bethyl Laboratories) were added for 1 hour at RT, washed four times, and tetramethylbenzidine (TMB) substrate was added. Reaction was stopped using 2N $H_2SO_4$ and read at 450 nm. Similarly, antibodies IgG, IgG1 and IgG2c specific to influenza A/PR8 strain in sera were measured with influenza virus coated plate.

Statistical Analysis

Statistical analysis was performed using GraphPad Prism (version 8). P values were calculated with Student's t test, or one-way ANOVA. $P<0.05$ was considered significant.

Example 2: Role of SCD1 in SLE

A recent study found that plasma from lupus patients have greatly increased levels of palmitoleic acid and oleic acid, two products of SCD, compared to healthy donors (Shin et al., *Metabolomics*, 14:14 (2018), suggesting that lupus disease could be associated with higher SCD activity in human (FIG. 14A)).

To test whether suppression of SCD activity may benefit lupus, a classic lupus mouse model, MRL/MpJ-Fas$^{lpr}$, was utilized. Female MRL/MpJ-Fas$^{lpr}$ mice were fed with control chow or SSI-4 chow from 6 weeks old. Proteinuria was measured from 8 weeks old, and mice fed with SSI-4 chow had no increase of proteinuria while most of mice fed with control chow gradually increase proteinuria level (FIG. 14B). Kidney histology showed that mice fed with SSI-4 chow had reduced immune cell infiltration and inflammation (FIG. 14C). Flow cytometry analyses of B cells showed that SSI-4 treatment significantly reduced B cell proliferation measured by Ki-67 expression (FIG. 14D) and metabolic activity, measured by expression of CD98, an amino acid transporter whose expression is associated with metabolic status (FIG. 14E).

SCD inhibition was tested in a different lupus model. Splenocytes from B6 (C)-H2-Ab1$^{bm12}$/KhEgJ (bm12) mice, a congenic mouse strain that is identical to C57BL/6 mice except 3 amino acids on MHC class II, were transferred to C57BL/6 mice. Alloactivation of donor CD4+ T cells by recipient antigen presenting cells led to chronic graft vs host disease (cGvHD) with immunopathologies similar to lupus, including increased autoantibody production due to follicular helper T cell driven germinal center formation and plasma cell generation. The recipient mice were treated with control chow or SSI-4 chow immediately after cell transfer. Serum anti-dsDNA autoantibody levels were measured. SSI-4 treatment reduced dsDNA production (FIG. 14F), generation of CXCR5+PD-1+ follicular helper T cells (FIG. 14G) and IgD−CD138+ plasma cells (FIG. 14H).

Altogether, these data indicate that lupus is associated with increased levels of SCD products, palmitoleic acid and oleic acid, and suppression of SCD activity can ameliorate lupus development in mouse models.

Materials and Methods

Mice

MRL/MpJ-Fas$^{lpr}$ mice and B6 (C)-H2-Ab1$^{bm12}$/KhEgJ (bm12) mice were purchased from the Jackson Laboratory. Six weeks old female MRL/MpJ-Fas$^{lpr}$ mice were treated with control chow or SSI-4 chow (60 mg/kg, on a two-week SSI-4 chow/control-chow alternating schedule) ad libitum for 15 weeks. Proteinuria was measured using Albustix strips (Siemens). Kidney histology was done using routine H&E staining. Thirty million splenocytes from 8 weeks old B6 (C)-H2-Ab1$^{bm12}$/KhEgJ (bm12) mice were transferred into C57BL/6 mice intraperitoneally. Mice were fed with control chow or SSI-4 chow (30 mg/kg, on an one-week SSI-4 chow/control-chow alternating schedule) ad libitum for 8 weeks.

Flow Cytometry

For analysis of surface markers, cells were stained in PBS containing 1% (w/v) bovine serum albumin on ice for 30 minutes, with anti-B220 (RA3-6B2, Biolegend), anti-CD4 (GK1.5, Biolegend), anti-CD138 (281-2, Biolegend), anti-PD-1 (J43, ThermoFisher). CXCR5 was stained with biotinylated anti-CXCR5 (2G8) followed by staining with streptavidin-conjugated PE (both from BD Biosciences). Cell viability was assessed using the Fixable Dye Ghost 510 (Tonbo Bioscience) following the manufacturer's protocol. Flow cytometry was performed on the LSR II, LSR Fortessa (BD Biosciences) or Attune NxT (ThermoFisher) cytometers, and analysis was performed using FlowJo software (Tree Star).

Example 3: Treating SLE

A human identified as having SLE is administered one or more SCD1 polypeptide inhibitors. For example, a human identified as having SLE is administered SSI-4. The administered inhibitor(s) can reduce the severity of one or more symptoms of SLE in the human.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating a mammal having an autoimmune disease, wherein said method comprises administering a SCD1 polypeptide inhibitor to said mammal, wherein said SCD1 polypeptide inhibitor is a compound having Formula (II):

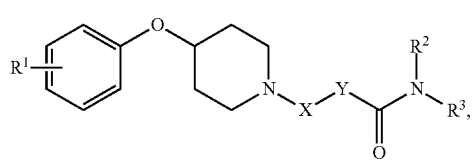

or pharmaceutically acceptable salt thereof;

wherein:
R$^1$ is halo;
X is —(C=O)NR$^4$—,
Y is

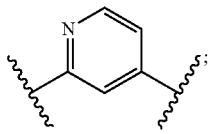 [SMILES: *c1ccnc(*)c1]

and
R$^2$, R$^3$, and R$^4$ are each independently H or an unsubstituted C$_{1-6}$alkyl.

2. The method of claim 1, wherein said mammal is a human.

3. The method of claim 1, wherein said autoimmune disease is selected from the group consisting of lupus, rheumatoid arthritis, spondyloarthropathy, Sjogren's syndrome, polymyositis, dermatomyositis, scleroderma, and multiple sclerosis.

4. The method of claim 1, wherein said autoimmune disease is systemic lupus erythematosus, cutaneous lupus, drug-induced lupus, or neonatal lupus.

5. A method for treating a mammal having an autoimmune disease, wherein said method comprises administering a SCD1 polypeptide inhibitor to said mammal, wherein said SCD1 polypeptide inhibitor is a compound having Formula (IIa):

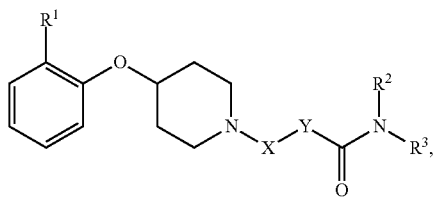

or a pharmaceutically acceptable salt thereof;
wherein:
$R^1$ is halo;
X is —(C=O)$NR^4$—;
Y is

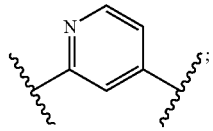 [SMILES: *c1ccnc(*)c1]

and
R2, R3, and R4 are each independently H or an unsubstituted alkyl.

6. The method of claim 1, wherein said SCD1 polypeptide inhibitor is 2-{[4-(2-chlorophenoxy)piperidine-1-carbonyl]amino}-N-methylpyridine-4-carboxamide:

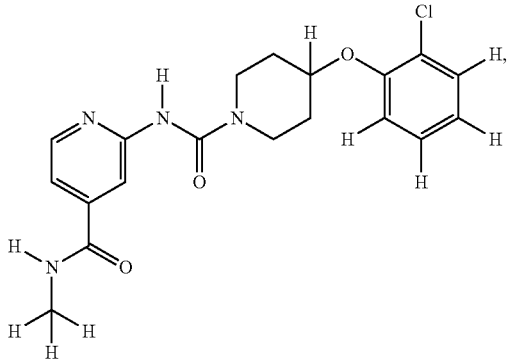

or a pharmaceutically acceptable salt thereof.

7. A method for treating a mammal having an autoimmune disease, wherein said method comprises administering a SCD1 polypeptide inhibitor to said mammal, wherein said SCD1 polypeptide inhibitor is a compound having Formula (I):

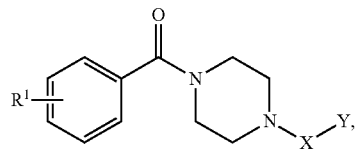

or a pharmaceutically acceptable salt thereof;
wherein:
$R^1$ is an unsubstituted $C_{1-6}$alkyl or $C_{1-6}$haloalkyl;
X is

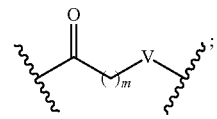

Y is selected from:

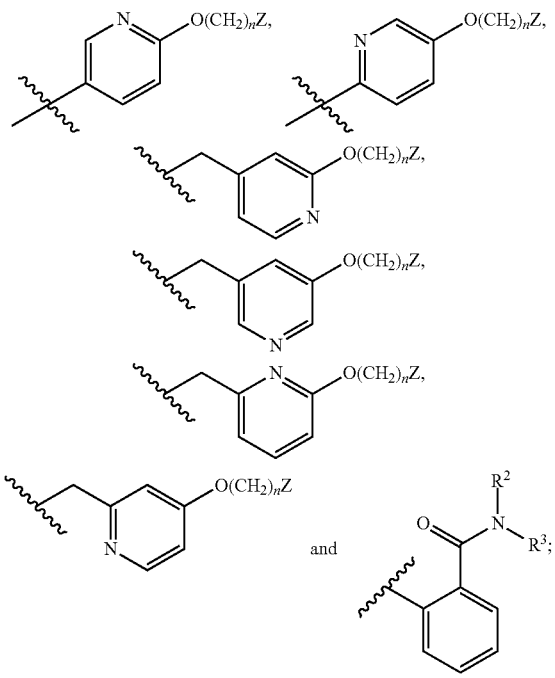

m is 0 or 1;
n is 0, 1, or 2;
V is $NR^4$ or O;
$R^2$, $R^3$, and $R^4$ are each independently H or an unsubstituted $C_{1-6}$alkyl; and
Z is an unsubstituted aryl.

8. The method of claim 7, wherein said SCD1 polypeptide inhibitor is a compound having Formula (Ia):

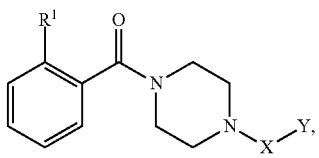

(Ia)

or a pharmaceutically acceptable salt thereof.

9. The method of claim 7, wherein said SCD1 polypeptide inhibitor is 2-(benzyloxy)-5-{[hydroxy({4-[2-(trifluoromethyl)benzoyl]piperazin-1-yl})methyl]amino}-1,2-dihydropyridin-2-ylium-1-ide:

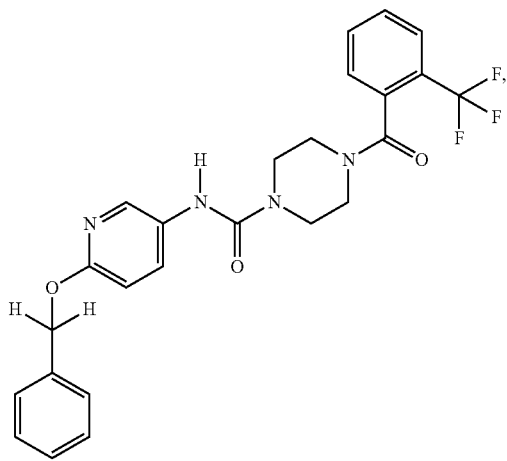 [SMILES: O=C(Nc1ccc(OCc2ccccc2)nc1)N1CCN(C(=O)c2ccccc2C(F)(F)F)CC1]

or a pharmaceutically acceptable salt thereof.

10. The method of claim 1, said method further comprising identifying the mammal as having said autoimmune disease.

11. The method of claim 5, wherein said method further comprises identifying the mammal as having said autoimmune disease.

12. The method of claim 5, wherein said mammal is a human.

13. The method of claim 5, wherein said autoimmune disease is selected from the group consisting of lupus, rheumatoid arthritis, spondyloarthropathy, Sjogren's syndrome, polymyositis, dermatomyositis, scleroderma, and multiple sclerosis.

14. The method of claim 5, wherein said autoimmune disease is systemic lupus erythematosus, cutaneous lupus, drug-induced lupus, or neonatal lupus.

15. The method of claim 7, wherein said method further comprises identifying the mammal as having said autoimmune disease.

16. The method of claim 7, wherein said mammal is a human.

17. The method of claim 7, wherein said autoimmune disease is selected from the group consisting of lupus, rheumatoid arthritis, spondyloarthropathy, Sjogren's syndrome, polymyositis, dermatomyositis, scleroderma, and multiple sclerosis.

18. The method of claim 7, wherein said autoimmune disease is systemic lupus erythematosus, cutaneous lupus, drug-induced lupus, or neonatal lupus.

* * * * *